US005846821A

United States Patent [19]
Guerinot et al.

[11] Patent Number: 5,846,821
[45] Date of Patent: Dec. 8, 1998

[54] METAL-REGULATED TRANSPORTERS AND USES THEREFOR

[75] Inventors: Mary Lou Guerinot, Etna, N.H.; David J. Eide, Columbia, Miss.

[73] Assignees: Trustees of Dartmouth College, Hanover, N.H.; Regents of the University of Minnesota, Minneapolis, Minn.

[21] Appl. No.: 758,621

[22] Filed: Nov. 27, 1996

Related U.S. Application Data

[60] Provisional application No. 60/018,578 May 29, 1996.

[51] Int. Cl.[6] .................................................. C07H 21/04
[52] U.S. Cl. .......................... 435/320.1; 435/6; 435/69.1; 435/172.3; 435/325; 436/501; 536/23.1; 536/24.1; 536/24.3; 536/24.31; 536/24.32; 536/24.33; 935/77; 935/78
[58] Field of Search .......................... 435/6, 69.1, 172.3, 435/320.1, 325; 436/501; 536/23.1, 24.1, 24.3–24.33; 935/77, 78

[56] References Cited

U.S. PATENT DOCUMENTS 5,364,451  11/1994  Raskin et al. .............................. 75/710

OTHER PUBLICATIONS

New England Biolabs Catalog [New England Biolabs, Beverly, Massachusetts, USA (1986/87)], pp. 60–62.

Dancis, A. et al., "Molecular Characterization of a Copper Transport Protein in S. cerevisiae: An Unexpected Role for Copper in Iron Transport," *Cell*, vol. 76, 393–402 (1994).

Dix, D. et al., "The FET4 Gene Encodes the Low Affinity Fe(II) Transport Protein of *Saccharomyces cerevisiae*," *The Journal of Biological Chemistry*, vol. 269, No. 42, 26092–26099 (1994).

Evans, K. et al., "expression of the Pea Metallothionein–like Gene P*s*MT*a* in *Escherichia coli* and *Arabidopsis thaliana* and Analysis oF Trace Metal Ion Accumulation: Implications for P*s*MT*a* Function," *Plant Molecular Biology*, vol. 20, 1019–1028 (1992).

Karin, M. and Richards, R., "Human Metallothionein Genes—Primary Structure of the Metallothionein–II Gene and a Related Processed Gene," *Nature*, vol. 299, 797–802 (1982).

Eide, D. et al., "A Novel Iron–Regulated Metal Transporter from Plants Identified by Functional Expression in Yeast," *Proc. Natl. Acad. Sci. USA*, vol. 93, 5624–5628 (1996).

(List continued on next page.)

*Primary Examiner*—Ardin H. Marschel
*Attorney, Agent, or Firm*—Ralph A. Loren, Esq.; Lahive & Cockfield, LLP

[57] ABSTRACT

Isolated nucleic acid molecules encoding novel members of the MRT family of polypeptides which include, in a preferred embodiment, at least one transmembrane domain having at least about 30%, more preferably at least about 50%, 55%, 60%, 70%, 80% or 90% amino acid sequence identity with SEQ ID NO:2, SEQ ID NO:4, SEQ ID NO:6, SEQ ID NO:8 or SEQ ID NO:14 and/or at least one histidine rich domain, are described. The MRT polypeptides of the invention are capable of transporting metals such as Fe(II), Cd, Co, Mn, Pb, Hg and Zn. Transgenic plants in which expression of an MRT polypeptide of the invention is altered are also described. These transgenic plants can be used to remove pollutants from soil or as nutritional supplements to treat iron- or zinc-deficiency. Antisense nucleic acid molecules, recombinant expression vectors containing nucleic acid molecules of the invention, and host cells into which the expression vectors have been introduced are also described. The invention further provides isolated MRT polypeptides, fusion polypeptides and active fragments thereof. Therapeutic methods utilizing compositions of the invention are also provided.

24 Claims, 26 Drawing Sheets

OTHER PUBLICATIONS

Fawaz, F., "Zinc Deficiency in Surgical Patients: A Clinical Study," *Journal of Parenteral and Enteral Nutrition*, vol. 9, No. 3, 364–369 (1985).

Levander, O., "Nutritional Factors in Relation to Heavy Metal Toxicants," *Federation Proceedings*, vol. 36, No. 5, 1683–1687 (1977).

Odne, M. et al., "Rationale for Adding Trace Elements to Total Parenteral Nutrient Solutions—A Brief Review," *Am J Hosp Pharm*, vol. 35, 1057–1059 (1978).

Repke, J., "Calcium, Magnesium, and Zinc Supplementation and Perinatal Outcome," *Clinical Obstetrics and Gynecology*, vol. 34, No. 2, 262–267 (1991).

Rugh, C. et al., "Mercuric Ion Reduction and Resistance in Transgenic *Arabidopsis Thaliana* Plants Expressing a Modified Bacterial merA Gene," *Proc. Natl. Acad. Sci. USA*, vol. 93, 3182–3187 (1996).

Shakman, R., "Nutritional Influences on the Toxicity of Environmental Pollutants," *Arch Environ Health*, vol. 28, 105–113 (1974).

Strobel, C. et al., "A Zinc–Deficiency Dermatitis in Patients on Total Parenteral Nutrition," *International Journal of Dermatology*, vol. 1, 575–581 (1978).

Valdes–Ramos, R., "Zinc: A Perinatal Point of View," *Progress in Food and Nutrition Science*, vol. 16, 279–306 (1992).

Walsh, C. et al., "Zinc: Health Effects and Research Priorities for the 1990s," *Environ Health Perspect*, vol. 102, suppl. 2, 5–46 (1994).

Yip, R., "Iron Deficiency: Contemporary Scientific Issues and International Programmatic Approaches," *J Nutr.*, vol. 124, 1479S–1490S (1994).

Zhao, H. and Eide, D., "The Yeast ZRT1 Gene Encodes the Zinc Transporter Protein of a High–Affinity Uptake System Induces by Zinc Limitation," *Proc. Natl. Acad. Sci. USA*, vol. 93, 2454–2458 (1996).

Zhao, H. and Eide, D., "The ZRT2 Gene Encodes the Low Affinity Zinc Transporter in *Saccharomyces Cerevisiae*," *The Journal of Biological Chemistry*, vol. 271, No. 38, 23203–23210 (1996).

FIG. 1A

```
1    MKTIFLVLIFVSFAISPATSTAPEECGSESANPCVNKAKALPLKVIAIFV
     ‾‾‾‾‾‾‾‾‾‾‾‾‾‾‾‾‾‾‾‾‾‾‾‾‾‾‾‾‾‾‾‾‾‾
     Signal Sequence 51   ILIASMIGVGAPLFSRNVSFLQPDGNFTIIKCFASGIILGTGFMHVLPD
     ‾‾‾‾‾‾‾‾‾‾‾                 ‾‾‾‾‾‾‾‾‾‾‾‾‾‾‾‾‾‾
         I                                II 101  SFEMLSSICLEENPWHKFPFSGFLAMLSGLITLAIDSMATSLYTSKNAVG
                     ‾‾‾‾‾‾‾‾‾‾‾‾‾‾‾‾‾‾
                           III 151  IMPHGHGHGHGPANDVTLPIKEDDSSNAQLLRYRVIAMVLELGIIVHS
                                         ‾‾‾‾‾‾‾‾‾‾‾‾‾‾‾‾
                                                IV 199  VVIGLSLGATSDTCTIKGLIAALCFHQMFEGMGLGGCILQAEYTNMKKFV
     ‾‾‾‾‾‾‾‾‾‾  ‾‾‾‾‾‾‾‾‾‾‾‾‾‾‾‾‾‾‾‾‾‾‾‾‾‾
                           V 249  MAFFFAVTTPFGIALGIALSTVYQDNSPKALITVGLLNACSAGLLIYMAL
     ‾‾‾‾‾‾‾‾‾‾‾‾‾‾‾‾‾‾‾‾‾  ‾‾‾‾‾‾‾‾‾‾‾‾‾‾‾‾‾‾‾‾‾‾
                VI                      VII 299  VDLLAAEFMGPKLQGSIKMQFKCLIAALLGCGGMSIIAKWA
                     ‾‾‾‾‾‾‾‾‾‾‾‾‾‾‾‾‾‾‾‾‾‾‾
                            VIII
```

FIG. 1B

```
IRT1    8  LIFVSFAISPATSTAPEECGSESANPCVNKAKALPLKVIAIFVILIASMIGVGAPLFSRN  67
           ||  :|::||  |||| |  |        |||||||||::||   || :|||::|||||
IRT2       LILFTFTVSPAISTAPEHCDSGFDNPCINKAKALPLKIVAIVAILTTSLIGVTSPLFSRY

IRT1   68  VSFLQPDGNIFTIIKCFASGIILGTGFMHVLPDSFEMLSSICLEENPWHKFPFSGFLAML  127
           :|||  |||:|| |  |:|||||||||||||||||||||| ||  :|||||||||:|::
IRT2       ISFLRPDGNGFMIVKCFSSGIILGTGFMHVLPDSFEMLSSKCLSDNPWHKFPFAGFVAMM

IRT1  292  LLIYMALVDLLAAEFMGPKLQGSIKMQFKCLIAALLGCGGMSIIAKWA  339
           :|:||||||||:|  :||:      ::|    ||   ||::|  :|:
IRT3       ILVYMALVDLIAADFLSTKMRCNFRLQIVSYVMLFLGAGLMSSLAIWA

IRT1  191  ELGIIVHSVVIGLSLGATSDTCTIKGLIAALCFHQMFEGMGLGGCILQAEYTNMKKFVMA  250
           ::|||||||||||::||| :  |:| |||||||| ?|||||||||||| : |:||||:
Rice       KMGIVVHSVVIGLMGASQNVCTIRPLVAALCFH?MFEGMGLGGCILQAGYGGRTRSALV IRT1  251  FFFAVTTPFGIALGIALSTVYQDNS  275
           |||: ||||||||||||| ||: :
Rice       FFFSTTTPFGIALGLALTRVYSDTA
```

FIG.4

Nucleotide sequence of IRT1:

```
   1 caaattcagc acttctcatg aaaacaatct tcctcgtact cattttttgtc tcttttgcaa
  61 tctctccagc aacttcaact gcgccggaag aatgtggaag cgagtcagcg aacccgtgcg
 121 tcaacaaagc taaagctttg cctctcaaag tcatagcaat cttcgtaatc ctcattgcaa
 181 gcatgattgg tgttggagct cctctctttta gccgtaacgt ttcgttcctc caaccagacg
 241 gaaacatctt cactatcatt aagtgtttcg cctccgggat catccttgga accggttta
 301 tgcacgtttt acctgattct ttcgaaatgt tgtcatctat atgtcttgaa gagaacccgt
 361 ggcataaatt tccttctcc ggatttctcg ctatgttatc gggtctaatc actctagcca
 421 ttgactccat ggccacgagc ctatacacca gcaagaacgc agttggtatc atgccccatg
 481 gtcatggtca tggtcacggc cccgcaaatg atgttacctt accaataaaa gaagatgatt
 541 cgtcaaatgc acagctcttg cgataccgag tcattgccat ggtcttggaa cttgggatca
 601 tagttcactc ggtggtcatt ggattatctc taggagcaac tagtgacact tgcaccatta
 661 aaggacttat agcagctctt tgcttccatc aaatgttcga aggcatgggt cttggcggtt
 721 gtatcctcca ggctgagtat acaaatatga agaaatttgt tatggcgttc tttttcgcgg
 781 taacaacacc attcggaata gcgttaggga tcgctctatc aactgtttac caagataata
 841 gcccaaaagc tttgatcacg gttggacttc taaatgcatg ctccgctgga ttgctcattt
 901 acatggcact cgtggatctt ctagctgcgg agttcatggg acctaagctt caaggtagca
 961 tcaaaatgca gttcaagtgt ttaatcgcgg ctcttctcgg gtgcggtgga atgtcgatta
1021 tcgccaaatg ggcttaacta atactccaga tattgcggaa ttgaaatcat gtggatttca
1081 ttatcgaact aaaaccgttt taggtttacg tctcgattct ctatcggttt tttatcttct
1141 cttacaaaag atttgcgtgg atctatcaca ttttaaggaa catgtctttt ggtagatatg
1201 taaatgtgat aggccccacg attcatagtt ttcttttgta tcttccttta ttttgtcaag
1261 gcagtatagt tcatatcgtg taatgttttt gcatctcata taaataaata aaacttttgc
1321 tgcttttttc
```

FIG. 5

Protein sequence:

MKTIFLVLIFVSFAISPATSTAPEECGSESANPCVNKAKALPLK
VIAIFVILIASMIGVGAPLFSRNVSFLQPDGNIFTIKCFASGIILGTGFMHVLPDSF
EMLSSICLEENPWHKFPFSGFLAMLSGLITLAIDSMATSLYTSKNAVGIMPHGHGHGH
GPANDVTLPIKEDDSSNAQLLRYRVIAMVLELGIIVHSVVIGLSLGATSDTCTIKGLI
AALCFHQMFEGMGLGGCILQAEYTNMKKFVMAFFFAVTTPFGIALGIALSTVYQDNSP
KALITVGLLNACSAGLLIYMALVDLLAAEFMGPKLQGSIKMQFKCLIAALLGCGGMSI
IAKWA

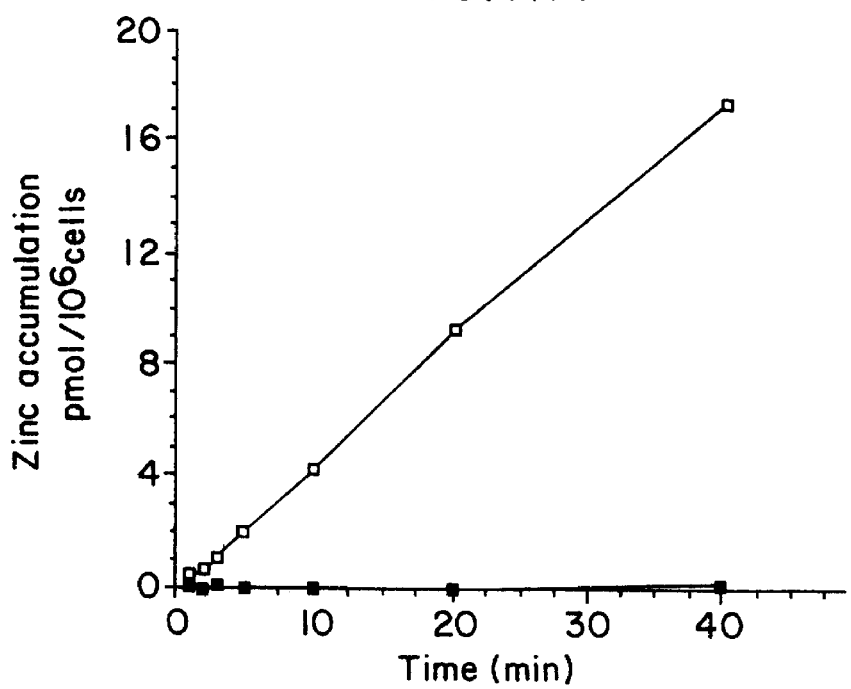
FIG.IIA
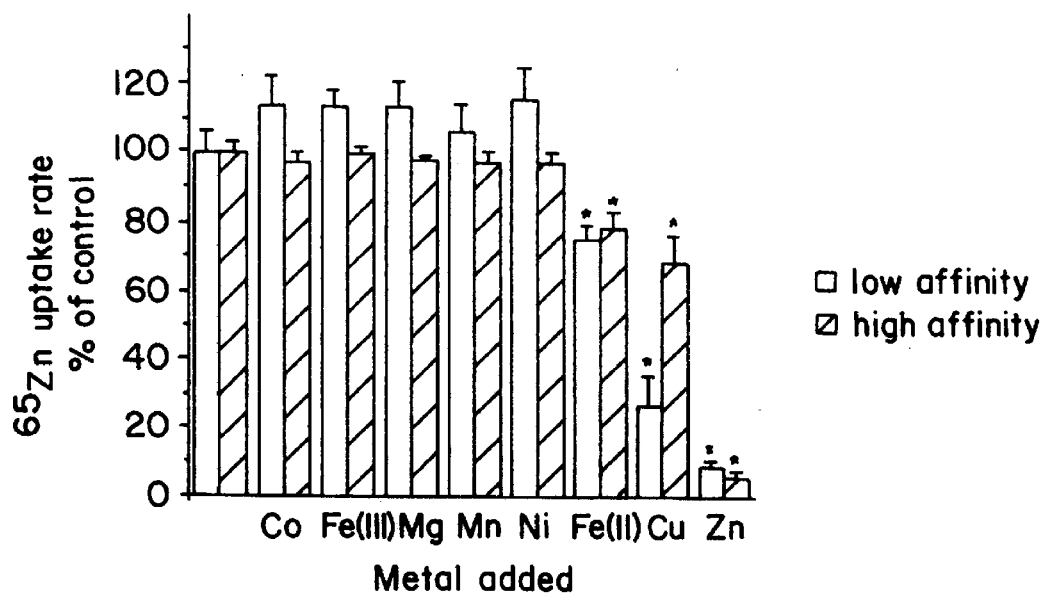
FIG.IIB

ZIP1 protein sequence

MSECGCFSATTMLRICVVLIICLHMCCASSDCTSHDDPVSQDEAEKATKLKLGSIALLV
AGGVGVSLPLIGKRIPALQPENDIFFMVKAFAAGVILCTGFVHILPDAFERLSSPCLEDT
TAGKFPFAGFVAMLSAMGTLMIDTFATGYYKRQHFSNNHGSKQVNVVVDEEEHAGHVHIH
THASHGHTHGSTELIRRRIVSQVLEIGIVVHSVIIGISLGASQSIDTIKPLMAALSFHQF
FEGLGLGGCISLADMKSKSTVLMATFFSVTAPLGIGIGLGMSSGLGYRKESKEAIMVEGM
LNAASAGILIYMSLVDLLATDFMNPRLQSNLVWLHLAAYLSLVLGAGSMSLLAIWA

ZIP1 nucleotide sequence

CAGTGTGAGTAATTTAGCAAGAACATAAATATCTTAAACTCATGTCTGAATGTGGATGTT
TTTCGGCAACAACTATGTTGAGAATTGTGTAGTATTGATAATATGTTGCATATGTGTT
GTGCCTCGAGTGTGATTGTACAAGTTCACGATGTCTGTGTCTTGTAGCCGAAGCAGAGAAAG
CGACGAAGCTAAAGCTTGGTTCGATAGCTTACTTCTTGTAGCCGGAGGAGTCGGCGTGA
GTCTACCGTTGATCGGGAAAAGGATTCCGGGCGTTACAACCAGGTTCGTTCATATCTTCA
TGGTGAAAGCTTTGCTGCAGGAGTTGAGCTCTCCATGTCCTCTGAGGACACTCTTATGATGTCGGAAGTTCCCGT
ACGCGTTCGAGAGATTGAGCGATGCTCGGCGAACATTTAGCAATAACCATGGGAGCAAGCAAGCACGCTAGTCACGGAC
CAGGGTATTACAAGAGGAAGAGCATGCGGGTCATGTCAGAAGACGTATAGTGTCGCAGGTGCTTGAGATTG
TAGTAGATGAAGAAGAGACATGGTTCGACCGAGTTGATCAGAAGACGTATAGTCACTTGGAGCTTCACAGAGCATAGACA
ACACACATGGTTGTGCATTCGGTTATTATAGGGGATATCTTCCATCAGTTCTTTGAAGGTTCTTGCCTCG
CCATAAAGCCACTCATGCCTGGGCGCCACTTGGGATTGGGATAGGAGGCAATAATGTTGGAAGGAATGTTGAATGCTGCATCTGCTG
GTGGATGCATCTCCCTGGGCCCTGATCTGGGCCTCATTCTTGATCTTGAACTAACAACAAAACAAAC
TCTCGGTGACGCGCCAGAGAAAGAGGAGACATGTCTGGCCTTCACTCTCTCTGCTACTTATGTATGAATGCAAGAT
ACAGGAAAGAGAGGAACAAAAGAGGCAAAGAGGTCAAGCAATAATGTTGGAAGGAATGTTGAATGCTGCATCTGCTG
GGATACTCATATACATCTCTGGCTTCACTTGGCCTTGGCCCTGATCTCTGCTTATCTCTCTGCTACTTATGTATGAATGCAAGAT
TGCAATCCAATCTCTGGCTTCACTTGGGCCCTGATCTCGGCCCATCTGGGCCTCATTCTTGATCTTGAACTAACAACAAAACAAAC
CCATGTCTCCTCCGCCATCTGGGCCTCTTTTTCTCAAATCTGTAATGGTGTTTCTAATCTCAGAATCAATACTA
CAAATGCCGCTCTTTTTCTCAAATCTGTAATGGTGTTTCTAATCTCAGAATCAATACTA
TTCTATCTTGAACAC

FIG. 19

ZIP2 protein sequence

```
  1 MALSSKTLKS TLVFLSIIFL CFSLILAHGG IDDGDEEEET NQPPPATGTT
 51 TVVNLRSKGL VLVKIYCIII LFFSTFLAGI SPYFYRWNES FLLLGTQFSG
101 GIFLATALIH FLSDANETFR GLKHKEYPYA FMLAAAGYCL TMLADVAVAF
151 VAAGSNNNHV GASVGESRED DDVAVKEEGR REIKSGVDVS QALIRTSGFG
201 DTALLIFALC FHSIFEGIAI GLSDTKSDAW RNLWTISLHK VFAAVAMGIA
251 LLKLIPKRPF FLTVVYSFAF GISSPIGVGI GIGINATSQG AGGDWTYAIS
301 MGLACGVFVY VAVNHLISKG YKPLEECYFD KPIYKFIAVF LGVALLSVVM
```

ZIP2 nucleotide sequence

```
   1 ATGGCTTTGT CTTCCAAAAC CCTAAAGTCA ACTCTCGTCT TCCTCTCTAT
  51 TATTTTCCTC TGTTTCTCCT TGATCCTAGC TCACGGCGGC ATAGACGACG
 101 GCGACGAAGA AGAGGAGACC AACCAGCCAC CTCCGGCCAC CGGAACAACC
 151 ACCGTCGTGA ATCTCCGATC CAAAGGCTTG GTGCTTGTGA AGATCTACTG
 201 TATTATAATA CTCTTCTTTA GCACATTCTT AGCCGGAATT TCACCTTACT
 251 TTTACCGATG GAACGAGTCG TTTCTCCTCC TAGGAACTCA ATTCTCCGGT
 301 GGTATATTCC TCGCGACCGC TCTAATCCAt TTCCTCAGCG ACGCTAACGA
 351 GACTTTCCGA GGGTTAAAAC ACAAAGAGTA TCCTTACGCT TTCATGTTAG
 401 CAGCCGCTGG ATATTGCCTT ACAATGCTGG CAGATGTGGC GGtTGCGTTT
 451 GTaGCGGCTG GGAgTAATAA CAACCACgTC GGAGcTAGCg TCGGAGAGTC
 501 GAGGGAGGAT GAtGACGTGG CAGtGAAAGA GGAAGGACgT CGTGAGATAA
 551 AGAGTGGTGT TGATGTGAGT CAAGCGcTTA TACGAACTAG TGGATTTGGA
 601 GACACAGCTT TGCTGATTTT TGCTCTTTGT TTTCACTCCA TCTTTGAGGG
 651 AATCGCCATT GGTCTCTCAG ACACTAAAAG CGACGCTTGG AGAAACCTAT
 701 GGACAATATC GTTGCACAAG GTCTTTGCGG CCGTAGCAAT GGGAATAGCT
 751 CTTCTCAAGC TAATCCCTAA ACGTCCATTC TTCCTCACTG TCGTCtACTC
 801 CTTCGCCtTT GGGAtATCGA GTCCCATAGG TGTCGGGATT GGCATTGGAA
 851 TCaATGCCac TAGCCAAGGA GCTGGTGGTG AcTGGACCtA CGCgATcTcT
 901 ATGGGGCTTG CGtGTGGAGT TTTtGTGTAC GTTGCGGTTA ACCATcTCAT
 951 cTCAAAAGGG TATAAGCCTC TTGAGGAATG TtAcTTCGAC AAGCCAAtct
1001 ACAAGTTTAT TGcCGtCTtC CtCGGTGTTG CTTTGCtctC TGTTGTAAtG
1051 ATTTGGGATT G
```

FIG. 20

ZIP3 protein sequence

MKTKSVKLLFFFFSVSLLLIAVVNAAEGHSHGGPKCECSHEDDHENKAGARKYKIAAIPT
VLIAGIIGVLFPLLGKVFPSLRPETCFFFVTKAFAAGVILATGFMHVLPEAYEMLNSPCL
ISEAWEFPFTGFIAMIAAILTLSVDTFATSSFYKSHCKASKRVSDGETGESSVDSEKVQI
LRTRVIAQVLELGIIVHSVVIGISLGASQSPDAAKALFIALMFHQCFEGLGLGGCIAQGK
FKCLSVTIMSTFFAITTPIGIVVGMGIANSYDESSPTALIVQGVLNAASAGILIYMSLVD
LLAADFTHPKMQSNTGLQIMAHIALLLGAGLMSLLAKWA

ZIP3 nucleotide sequence

GTGTGAGTAATTTAGAAGCCCTAATTTAAATAAGATAGAGATTATGAAGACTAAGA
GCGTGAAACTCTTATTCTCTCCGTCTCTCCCTCCTCCCTCGCCGTCGTCAACG
CCGCGAAGGCCATTCACATGGTGGACCAAATGTGAATGCTCACGAAGACGACCATG
AAACAAAGCCGGAGCTCTTTCCCTTGTTAGGCAAGTCTTCCCTTCTTGCGTCCAGAAA
GCATAATCGGAGTTCTTTCGTCCTGAAAGCTTTCGCAGCCGGAGTTATCTTGGCTACCGGATTTA
CATGTTTCTTCTGCCTGAGGCTTACGAGATGCTTAACTCTCATGTTTGATATCTGAAGCAT
TGCATGTCTGTCCCGGAATTCCGTTCACCGGATTTATGCGATCATTGCTGCAAGCGTCTGACGTTATCGTTG
GGGAATTTCCGTTCACCGGAGTTTCTATAAATCGCATTGCAAGCGTCCAAATTCTCCGGACTAGAG
ATACATTTGCCACTTCGAGTTCGAGTCCTCCGTTGACTCCGAAAGCTCAGTGTTATTGCCTTAATGTTTCATC
ATGGAGAAACCGGGAGTATTGGAGTTGGGAATAATAGTACACTCTGTTATTGCTCAGGGAAATTCAAGTGTTGT
TTATTGCACAGGTATTGGAGAGCCCAGAGTTGGTGTTGGTGTTATTGCTCAGGGAAATTCAAGTGTTGT
TAGGAGCTTCACAGAGCCCAGAGTCTAGGCCTTGACGTTCGACGTTCGACGTCGAAAGCGATAGGAATCGTTGTGGAA
AATGCTTCGAAGGTCTAGGCCTTCGACGTTCGAACGCGATAAGGAATCGTTGTGGAA
CAGTAACAATCATGTCGACTTCTTACGATGAGTCTTCACCAACGCGTCTTGGTTGACCTTCTCGCAGCAG
TGGGAATAGCAAATTCCGCAGGCATTCATCAATACTGGGCTTCAAATTATGCCCATATTGCTC
TGAACGCTGCATCCGCACCCTAAATGCCCTCATGTCTCATTGGCTTATGGCCCATATTGCTC
ATTTCACGCACCCTAAATGCCCTCATGTCTCATTGGCTTATGGCCCATATTGCTC
TCCTTCTGGTGCTGGCCTCAGTTTTGCTCAGTATATTTGCTCATGGCCACCTTGAATTCGAATTATTGTT
CAACTCTTCAGTTTTGCTCATGATCATGGGATCTCTATTTCTGAAACACTCATGT
CTATTTCCCCTTTCAATGATTATTACAATTGTGTATATTGATCAGTGTCCAAGGAAAAAAAAAA
ACTCATGTTAACATTATTACAATTGTGTATATTGATCAGTGTCCAAGGAAAAAAAAAA
AAAAAAAAAAAAAAAACTAAATTACTCACACTGGCGCCGCCACGCGGTGGAG
CTCCAGCTTTTGTTCCCTTTAGTGAGGGTTAATTTCGAGCTTGGCGTAATCATA

FIG. 21

ZRT1 Nucleotide Sequence

```
   1  atgagcaacg ttactacgcc gtggtggaaa caatgggacc cttctgaagt
  51  tacacttgcc gataaaaccc ctgatgatgt gtggaagacc tgtgttttgc
 101  aaggtgttta ctttggtgga aacgagtaca atggtaactt aggtgccaga
 151  atatcttccg tctttgttat tctttttcgtg agtactttt tcaccatgtt
 201  cccattaatc tcaacaaaag tgaaaagatt gagaattcct ctatatgttt
 251  acctttttcgc aaagtatttt ggttccggtg ttattgttgc aaccgcattt
 301  atccacttaa tggaccctgc ttatggtgcg attggtggta ccacttgtgt
 351  aggacaaacc ggtaactggg gtctttattc atggtgtcct gccattatgc
 401  taacgagttt gaccttcact ttccttactg atctattcag tagcgtctgg
 451  gttgaaagaa agtatggtct ttcccatgac catacccacg atgaaattaa
 501  agacactgtt gtgagaaaca ctgcagctgt ttcaagtgag aatgacaatg
 551  agaatggtac tgcaaatgga tctcatgaca ccaagaacgg agtagagtat
 601  tatgaagatt cagacgctac atccatggat gttgttcaat catttcaagc
 651  acaattttat gccttttttaa ttttagaatt cggtgtgatt ttccactccg
 701  ttatgatcgg tctaaacctg ggaagtgttg gtgatgagtt ctcctcccta
 751  taccctgtct tagtgttcca tcaatcattt gaaggtttag gtattggtgc
 801  aagattgtca gccattgaat tccctagatc aaagagatgg tggccatggg
 851  ccctatgtgt tgcgtatggg ttaaccacac caatctgtgt ggccatcggt
 901  ttgggtgttc gtaccagata cgtcagcggt tcttacactg cgcttgttat
 951  ctctggtgtt ttggatgcca tttctgctgg tatcttattg tacactggtt
1001  tggttgaact actagcaaga gactttatat tcaatcctca aagaacaaag
```

ZRT1 Amino Acid Sequence

```
  1  MSNVTTPWWK QWDPSEVTLA DKTPDDVWKT CVLQGVYFGG NEYNGNLGAR
 51  ISSVFVILFV STFFTMFPLI STKVKRLRIP LYVYLFAKYF GSGVIVATAF
101  IHLMDPAYGA IGGTTCVGQT GNWGLYSWCP AIMLTSLTFT FLTDLFSSVW
151  VERKYGLSHD HTHDEIKDTV VRNTAAVSSE NDNENGTANG SHDTKNGVEY
201  YEDSDATSMD VVQSFQAQFY AFLILEFGVI FHSVMIGLNL GSVGDEFSSL
251  YPVLVFHQSF EGLGIGARLS AIEFPRSKRW WPWALCVAYG LTTPICVAIG
301  LGVRTRYVSG SYTALVISGV LDAISAGILL YTGLVELLAR DFIFNPQRTK
351  DLRELSFNVI CTLFGAGIMA LIGKWA
```

FIG.22A

ZRT2 Nucleotide Sequence

```
   1  atggttgatc ttatagcgag ggatgactcc gtagatactt gccaagcttc
  51  taacggctac aatgggcacg caggtcttag aattctggca gtattcatta
 101  tactgatatc gtcaggattg ggagtttatt tcccaatttt gtcatcacgg
 151  tattcgttta taaggctacc aaattggtgc ttttcatag cgaagttctt
 201  cggttctggt gtcattgttg ccacagcgtt cgttcatctt ctacagcccg
 251  cagccgaagc tctgggagat gaatgtcttg gtggcacatt tgccgaatat
 301  ccatgggctt tgggatctg tttaatgtcg cttttcttac ttttcttcac
 351  tgaaatcatc acgcattatt ttgtagcgaa aacgctggga cacgatcatg
 401  gggaccatgg ggaagttacc agtattgatg ttgatgctcc cagttcggga
 451  tttgtcatca gaaatatgga ctcggatcct gtatctttca ataacgaagc
 501  tgcctactcc atccataatg acaaaactcc gtacactact agaaatgaag
 551  agattgtcgc tactcctata aaggaaaaag aacccggctc aaatgttact
 601  aattatgatc tggaaccggg aaaaacagag tcactagcta atgaactagt
 651  tccaaccagt tcccatgcga caaatctcgc ttctgtacct ggaaaagatc
 701  attattctca cgaaaatgac catcaagatg tctcccagtt ggccacacgt
 751  atcgaggagg aagataaaga gcagtatctc aatcagatac tagctgtttt
 801  tattctagaa tttggcatca tctttcactc tgtatttgtg ggtctttcgc
 851  tatctgtcgc gggtgaagaa ttcgaaacct tatttatcgt tttaactttc
 901  caccaaatgt tcgaaggttt gggtctaggc acaagagttg ccgaaacgaa
 951  ttggccagaa agtaagaagt acatgccttg gttaatggga ttagccttca
1001  ctttaacgtc acccatagca gtcgcggtag gtattggtgt cagacactct
1051  tggatacctg gctctagaag agcattaatt gctaatggtg ttttgactc
1101  gatatcatca ggaattctta tttatactgg actagtcgaa ttaatggctc
1151  atgaattctt atactctaat caattcaaag gacctgatgg cctcaaaaaa
1201  atgcttagtg catatctcat catgtgttgt ggagctgctt taatggctct
1251  tctagggaaa tgggcatag
```

FIG. 22B

ZRT2 Amino Acid Sequence

```
  1 MVDLIARDDS VDTCQASNGY NGHAGLRILA VFIILISSGL GVYFPILSSR
 51 YSFIRLPNWC FFIAKFFGSG VIVATAFVHL LQPAAEALGD ECLGGTFAEY
101 PWAFGICLMS LFLLFFTEII THYFVAKTLG HDHGDHGEVT SIDVDAPSSG
151 FVIRNMDSDP VSFNNEAAYS IHNDKTPYTT RNEEIVATPI KEKEPGSNVT
201 NYDLEPGKTE SLANELVPTS SHATNLASVP GKDHYSHEND HQDVSQLATR
251 IEEEDKEQYL NQILAVFILE FGIIFHSVFV GLSLSVAGEE FETLFIVLTF
301 HQMFEGLGLG TRVAETNWPE SKKYMPWLMG LAFTLTSPIA VAVGIGVRHS
351 WIPGSRRALI ANGVFDSISS GILIYTGLVE LMAHEFLYSN QFKGPDGLKK
401 MLSAYLIMCC GAALMALLGK WA
```

FIG. 23

IRT2 peptide sequence (345 aa)

1   DPRVRLILFT FTVSPAISTA PEHCDSGFDN PCINKAKALP LKIVAIVAIL
51  TTSLIGVTSP LFSRYISFLR PDGNGFMIVK CFSSGIILGT GFMHVLPDSF
101 EMLSSKCLSD NPRHKFPSGG LVAMMSGLVT LAIDSITTSL YTGKNSVGPV
151 PDEEYGIDQE KAIHMVGHNH SHGHGVVLAT KDDGQLLRYQ VIAMVLEVGI
201 LFHSVVIGLS LGATNDSCTI KGLIIALCFH HLFEGIGLGG CILQADFTNV
251 KKFLMAFFFT GTTPCGIFLG IALSSIYRDN SPTALITIGL LNACSAGMLI
301 YMALVDLLAT EFMGSMLQGS IKLQIKCFTA ALLGCAVMSV VAVWA

IRT2 nucleotide sequence

1    TCGACCCACG CGTCCGCCTC ATCCTATTCA CCTTCACCGT ATCTCCGGCG
51   ATCTCAACGG CCCCGGAACA TTGTGATAGC GGCTTTGATA ACCCGTGCAT
101  CAACAAAGCT AAGGCTTTAC CACTCAAAAT CGTAGCCATT GTTGCCATAC
151  TTACAACAAG CTTGATAGGC GTGACCTCTC CTCTTTTCAG CCGTTACATT
201  TCGTTCCTCC GTCCCGATGG CAATGGTTTC ATGATCGTCA AATGTTTTTC
251  TTCTGGAATC ATCCTTGGAA CCGGTTTCAT GCACGTCTTG CCTGACTCTT
301  TCGAGATGTT GTCATCGAAA TGTCTTAGTG ATAATCCGCG CATAAGTTC
351  CCTTCTGGGG GTTTAGTCGC TATGATGTCC GGTCTAGTCA CTCTAGCCAT
401  TGACTCCATT ACCACCAGCC TTTATACCGG TAAGAACTCA GTCGGACCAG
451  TGCCTGATGA AGAGTATGGC ATTGATCAAG AGAAAGCGAT TCACATGGTA
501  GGCCACAATC ATAGTCACGG TCATGGTGTA GTGCTAGCAA CTAAAGATGA
551  TGGACAGCTT TTGCGCTACC AAGTCATTGC CATGGTATTG GAGGTTGGGA
601  TTTTATTTCA TTCTGTGGTC ATTGGACTAT CTCTAGGAGC AACTAATGAT
651  TCATGTACCA TTAAAGGACT CATCATAGCT CTTTGCTTCC ATCACTTGTT
701  CGAAGGCATA GGTCTTGGTG GCTGCATCCT CCAGGCAGAT TTTACAAATG
751  TGAAGAAGTT CTTGATGGCA TTCTTTTTCA CTGGAACAAC ACCTTGTGGT
801  ATCTTTCTTG GAATCGCATT GTCGAGTATC TATAGAGATA ACAGTCCAAC
851  CGCGTTGATT ACGATTGGAC TGTTAAATGC TTGCTCGGCC GGAATGCTCA
901  TCTACATGGC CCTCGTCGAC CTTCTAGCTA CCGAGTTCAT GGGGTCAATG
951  CTCCAAGGTA GCATCAAACT TCAGATCAAG TGCTTCACGG CGGCTTTGCT
1001 TGGCTGCGCC GTAATGTCGG TCGTCGCCGT GTGGGCTTAA ACACTCTTTC
1051 AACATAATCA ATAAATTATT TGATTTATTA ATCCAGGCGA CCAATACTTT
1101 CGCCTTTGGA AAATTGAGTT TTTGTTTTTA AGTTTGAATC ATTTATTAGT
1151 TTGTATAGTG CATGTAAGCG TTTGAAAGAA ATTTCTTTTT ATGACATTGT
1201 AAATTTATTT TTATGGATGC GATGTTTACT TTCTTAAAAA AAAAAAAAA
1251 AAAAAAAAAA AAAA

METAL-REGULATED TRANSPORTERS AND USES THEREFOR

RELATED APPLICATIONS

This application claims the benefit of the previously filed United States Provisional application Ser. No. 60/018,578, filed May 29, 1996, the contents of which are hereby incorporated by reference.

BACKGROUND OF THE INVENTION

Iron deficiency is one of the most common human nutritional disorders in the world today (Yip, R. (1994) *J. Nutr.* 124: 1479S–1490S). Indeed, iron is an essential nutrient for virtually all organisms because it plays a critical role in important biochemical processes such as respiration and photosynthesis. Although abundant in nature, iron is often available in limited amounts because the oxidized form, Fe(III), is extremely insoluble at neutral or basic pH. This fact is of particular importance to agriculture because approximately one-third of the world's soils are classified as iron-deficient (Yi, Y. et al. (1994) *Plant Physiol.* 104: 815–820). Many "iron-efficient" plant varieties have iron uptake strategies (designated strategy I or strategy II) that, not surprisingly, are directed at solubilizing iron (Römheld, V. (1987) *PhysioL Plant.* 70: 231–234). Strategy II plants, which include all of the grasses, release Fe(III) compounds called "phytosiderophores" into the surrounding soil that bind iron and are then taken up into the roots. Most other iron-efficient plants use strategy I and respond to iron deprivation by inducing the activity of membrane-bound Fe(III) chelate reductases that reduce Fe(III) to the more soluble Fe(II) form. The Fe(II) product is then taken up into the roots by an Fe(II) specific transport system that is also induced by iron-limiting growth conditions. Furthermore, the roots or strategy I plants release more protons when iron-deficient, lowering the rhizosphere pH and thereby increasing the solubility of Fe(III). Thus, it would be desirable to take advantage of this understanding of iron-uptake strategies to produce plants which have increased iron-uptake capabilities.

Furthermore, another metal, zinc, is an integral cofactor of many proteins and is indispensable to their catalytic activity and/or structural stability (Vallee and Auld (1990) *Biochemistry* 9:5647–5659). Moreover, zinc is a ubiquitous component of enzymes involved in transcription and of accessory transcription factors, the zinc finger proteins, that regulate gene expression (Rhodes and Klug (1993) *Sci. Am.* 268(2) :56–65). Because of the many roles this metal plays in cellular biochemistry, zinc is an essential nutrient for all organisms. Despite this importance, very little is known about the molecular mechanisms cells use to obtain zinc. No transporter genes involved in zinc uptake (i.e. influx transporters) have been isolated from any organism. Recently, genes have been identified whose products are responsible for detoxifying intracellular zinc by transporting the metal from the cytoplasm to the cell exterior or into intracellular compartments (i.e. efflux transporters). These genes include the closely related eukaryotic genes, COT1, ZRC1, and Znt-1 (Conklin et al. (1992) *Mol. Cell Biol.* 12:3678–3688; Kamizono et al. (1989) *Mol. Gen. Genet.* 219:161–167; Palmiter and Findley (1995) *EMBO J.* 14:639–649). While important for zinc detoxification, these genes do not appear to play a role in zinc uptake.

In addition, metal ion pollution is perhaps one of the most difficult environmental problems facing the industrial world today. Unlike the organic and even halogenated organic pollutants, which can be degraded in the soil, metals are essentially nonmutable. The electrolytic, in situ immobilization and chemical leaching technologies for cleaning polluted sites are all very expensive, particularly in light of how vast some of these sites are. With the exception of approaches like vitrification, most in situ metal ion remediation schemes require some mechanism for increased mobilization of the metal ion. This raises the possibility of further endangering local wildlife or adjacent ecosystems not already affected. Thus, a need still exists for better methods for removing toxic pollutants from the soil.

Accordingly, an object of the invention is to generate transgenic plants in which expression of an MRT polypeptide is altered such that metal-uptake is increased.

Another object of the invention to provide methods for removing toxic pollutants, such as heavy metals, from the environment.

Yet another object of the invention is to provide methods for improving human or animal nutrition, e.g., for treating metal-deficiency, e.g., iron-deficiency or zinc-deficiency.

SUMMARY OF THE INVENTION

This invention is based, at least in part, on the discovery of a family of polypeptides, designated herein as metal-regulated transporter, MRT, polypeptides, which share several structural/functional properties, at least one of which is related to metal transport. Structurally, the MRT polypeptides include, for example, at least one transmembrane binding domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14 and/or at least one histidine rich domain. Functionally, the MRT polypeptides are capable of, for example, transporting metals, e.g., Fe, e.g., Fe(II), Cd, Co, Mn, Pb, Hg and/or Zn.

Preferred MRT polypeptides have an overall amino acid sequence identity of at least about 40%, preferably at least about 42%, 45%, 47%, 50%, more preferably at least about 55%, 60%, 70%, 80%, 90%, or 95% with an amino acid sequence of SEQ ID NO:2, SEQ ID NO:4, SEQ ID NO:6, SEQ ID NO:8 or SEQ ID NO:14; it has eight transmembrane domains; it has four histidine rich domains; or it can be isolated from the Arabidopsis family of plants.

Accordingly, this invention pertains to isolated nucleic acid molecules encoding an MRT polypeptide. Such nucleic acid molecules (e.g., cDNAs) have a nucleotide sequence encoding an MRT polypeptide (e.g., an *A. thaliana* IRT1 polypeptide, an *A. thaliana* IRT2 polypeptide, an *A. thaliana* ZIP1 polypeptide, an *A. thaliana* ZIP2 polypeptide, or an *A. thaliana* ZIP3 polypeptide) or biologically active portions or fragments thereof, such as a polypeptide having an MRT bioactivity. In a preferred embodiment, the isolated nucleic acid molecule has a nucleotide sequence shown in SEQ ID NO:1, SEQ ID NO:3, SEQ ID NO:5, SEQ ID NO:7 or SEQ ID NO:13, or a portion or fragment thereof. Preferred regions of these nucleotide sequences are the coding regions. Other preferred nucleic acid molecules are those which have at least about 45%, preferably at least about 48%, more preferably at least about 50%, and most preferably at least about 55%, 60%, 70%, 80%, 90%, 95%, 97% or 98% or more nucleotide sequence identity over the entire sequence with a nucleotide sequence shown in SEQ ID NO:1, SEQ ID NO:3, SEQ ID NO:5, SEQ ID NO:7 or SEQ ID NO:13, or a portion or fragment thereof. Nucleic acid molecules which hybridize under stringent conditions to the nucleotide sequence shown in SEQ ID NO:1, SEQ ID NO:3, SEQ ID NO:5, SEQ ID NO:7 or SEQ ID NO:13, e.g., nucleic acid molecules which hybridize to at least 6 consecutive nucleotides of the nucleotide sequence shown in SEQ ID NO:1, SEQ ID NO:3, SEQ ID NO:5, SEQ ID NO:7 or SEQ ID NO:13, are also within the scope of the invention. Such portions or fragments include nucleotide sequences which encode, for example, polypeptide domains having an MRT bioactivity. Examples of portions or fragments of nucleic acid molecules which encode such domains include portions or fragments of nucleotide sequences of SEQ ID NO:1, SEQ ID NO:3, SEQ ID NO:5, SEQ ID NO:7 or SEQ ID NO:13 which encode one or more of the following: at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14 or at least one histidine rich domain. Nucleic acid molecules of the present invention which further comprise a label are also within the scope of the invention. Complements of the nucleic acid molecules of the present invention are also specifically contemplated.

In another embodiment, the nucleic acid molecules of the invention encode a polypeptide having an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity. Nucleic acid molecules encoding a polypeptide having at least about 40%, preferably at least about 42%, 45%, 47%, 50%, more preferably at least about 52%, and most preferably at least about 55%, 60%, 70%, 80%, 90%, 95%, 97% or 98% amino acid sequence identity over the entire sequence with an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity, are also within the scope of the invention.

Another aspect of the invention pertains to nucleic acid molecules which encode polypeptides which are fragments of at least about 20 amino acid residues in length, more preferably at least about 30 amino acid residues in length or more, of an amino acid sequence shown in SEQ ID NO:2, SEQ ID NO:4, SEQ ID NO:6, SEQ ID NO:8 or SEQ ID NO:14. Other aspects of the invention pertain to nucleic acid molecules which encode polypeptides which are fragments of at least about 20 amino acid residues in length, more preferably at least about 30 amino acid residues in length which have at least about 40%, more preferably at least about 42%, 45%, 47%, 50%, and most preferably at least about 55%, 60%, 70%, 80%, 90% or more (e.g., 95%, 97–98%) amino acid sequence identity over the entire sequence with an amino acid sequence shown in SEQ ID NO:2, SEQ ID NO:4, SEQ ID NO:6, SEQ ID NO:8 or SEQ ID NO:14, or a portion or fragment thereof having a biological activity, e.g., an MRT bioactivity. Portions or fragments of the polypeptides encoded by the nucleic acids of the invention include polypeptide regions which comprise, for example, various structural and/or functional domains of MRT family members. Such domains include portions or fragments of nucleotide sequences of SEQ ID NO:1, SEQ ID NO:3, SEQ ID NO:5, SEQ ID NO:7 or SEQ ID NO:13 which encode one or more of the following: at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, or at least one histidine rich domain. Nucleic acid molecules which are antisense to the nucleic acid molecules described herein are also within the scope of the invention.

Another aspect of the invention pertains to vectors, e.g., recombinant expression vectors, containing the nucleic acid molecules of the invention and host cells into which such recombinant expression vectors have been introduced. In one embodiment, such a host cell is used to produce an MRT polypeptide by culturing the host cell in a suitable medium. An MRT polypeptide protein can be then isolated from the medium or the host cell.

Still another aspect of the invention pertains to isolated MRT polypeptides (e.g., isolated *A. thaliana* IRT1 polypeptides) and active fragments thereof, such as peptides having an activity of an MRT polypeptide (e.g., at least one biological activity of an IRT1 polypeptide as described herein). The invention also provides an isolated or purified preparation of an MRT polypeptide. In preferred embodiments, an MRT polypeptide comprises an amino acid sequence of SEQ ID NO:2, SEQ ID NO:4, SEQ ID NO:6, SEQ ID NO:8 or SEQID NO:14. In other embodiments, the isolated MRT polypeptide comprises an amino acid sequence having at least about 40%, more preferably at least about 42%, 45%, 47%, 50%, and most preferably at least about 55%, 60%, 70%, 80%, 90% (e.g., 95%, 97%–98%) or more amino acid sequence identity over the entire sequence with an amino acid sequence of SEQ ID NO:2, SEQ ID NO:4, SEQ ID NO:6, SEQ ID NO:8 or SEQ ID NO:14, and, preferably has an activity of an MRT polypeptide (e.g., at least one biological activity of MRT). Preferred MRT polypeptides include, for example, at least one transmembrane binding domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, and/or at least one histidine rich domain. Preferred MRT polypeptides are capable of, for example, transporting metals, e.g., Fe, e.g., Fe(II), Cd, Co, Mn, Pb, Hg and/or Zn.

Fragments of the MRT polypeptides of the invention can include portions or fragments of the amino acid sequences shown in SEQ ID NO:2, SEQ ID NO:4, SEQ ID NO:6, SEQ ID NO:8 or SEQ ID NO:14, which are at least about 20 amino acid residues, at least about 30, or at least about 40 or more amino acid residues in length. The MRT polypeptide portions or fragments described herein can have an MRT bioactivity, e.g., one or more, in any combination, of the MRT biological activities described herein. Portions or fragments of the polypeptides of the invention can include polypeptide regions which comprise, for example, various structural and/or functional domains. Such domains include portions or fragments of amino acid sequences of SEQ ID NO:2, SEQ ID NO:4, SEQ ID NO:6, SEQ ID NO:8 or SEQ ID NO:14, which include at least one of the following: a transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8 or SEQ ID NO:14, or a histidine rich domain. Preferred amino acid sequences of each of these domains are described herein. The peptide fragments can be modified to alter MRT bioactivity, e.g., impart a non-wild type activity on MRT polypeptides, or to impart desired characteristics thereon, e.g., increased solubility, enhanced therapeutic or prophylactic efficacy, or stability. Such modified peptides are considered functional equivalents of peptides having an activity of MRT as defined herein. A modified peptide can be produced in which the amino acid sequence has been altered, such as by amino acid substitution, deletion, or addition. In another embodiment, a component which imparts a desired characteristic on a peptide can be linked to the peptide to form a modified peptide.

The invention also provides for an MRT fusion polypeptide comprising an MRT polypeptide and a second polypeptide portion having an amino acid sequence from a protein unrelated to an amino acid sequence which has at least about 40% or more amino acid sequence identity with an amino acid sequence shown in SEQ ID NO:2, SEQ ID NO:4, SEQ ID NO:6, SEQ ID NO:8 or SEQ ID NO:14.

The invention also provides transgenic plants in which the expression of an MRT polypeptide is altered, as well as seeds and cells derived from such plants. For example, the invention includes a method for evaluating the effect of the expression or misexpression of an MRT gene on a parameter related to metal transport. The method includes providing a transgenic plant having an MRT transgene, or which otherwise misexpresses an MRT gene, contacting the transgenic plant with an agent, and evaluating the effect of the transgene or misexpression of the MRT gene on the parameter related to metal transport (e.g., by comparing the value of the parameter for a transgenic plant with the value for a control, e.g., a wild-type plant).

In addition, the transgenic plant, e.g., rice, beans, peas and maize, in which expression of an MRT polypeptide is altered can be incorporated into a pharmaceutical composition which includes the transgenic plant, or a portion thereof, and a pharmaceutically acceptable carrier. Such compositions can be used as human or animal nutritional supplements to provide, for example, iron to a subject with iron-deficiency or zinc to a subject with zinc-deficiency. Antibodies, e.g., monoclonal or polyclonal antibodies, which bind to an epitope of or are specifically reactive with an MRT polypeptide or fragment thereof are also specifically contemplated in the present invention.

Methods for identifying an agent which inhibits or activates/stimulates an MRT polypeptide are also within the scope of the invention. These methods include contacting a first polypeptide comprising a naturally occurring ligand of MRT, with a second polypeptide comprising an MRT polypeptide and an agent to be tested and then determining binding of the second polypeptide to the first polypeptide. Inhibition of binding of the first polypeptide to the second polypeptide indicates that the agent is an inhibitor of an MRT polypeptide while activation/stimulation of binding of the first polypeptide to the second polypeptide indicates that the agent is an activator/stimulator or an MRT polypeptide.

In another aspect, the invention features a method for evaluating a candidate compound for the ability to interact with an MRT polypeptide. This method includes contacting the compound with the MRT polypeptide and evaluating the ability of the compound to interact with the MRT polypeptide. This method can be performed in vitro or in vivo.

The MRT polypeptides of the invention can be used to modulate metal concentrations in vitro or in vivo. In one aspect, the invention provides a method for modulating metal concentration in a biological sample containing the metal. This method includes providing a transgenic plant in which expression of an MRT polypeptide is altered and contacting the transgenic plant with the biological sample such that the metal concentration in the biological sample is modulated.

The invention further provides methods for removing a pollutant from soil. These methods include contacting a transgenic plant in which expression of an MRT polypeptide is altered with the soil such that the pollutant is removed from the soil. In a preferred embodiment, the pollutant is a metal, e.g., a metal selected from the group consisting of Pb, As, Co, Cu, Zn, Cd and/or Hg.

Additional methods of the invention include methods for treating a disorder associated with metal-deficiency, e.g., iron-deficiency or zinc-deficiency, in a subject. These methods include administering to a subject a therapeutically effective amount of a composition comprising a transgenic plant, or a portion thereof, in which expression of an MRT polypeptide is altered. In a preferred embodiment, the composition is administered in combination with a pharmaceutically acceptable carrier. In other preferred embodiments, the MRT polypeptide in the transgenic plant is overexpressed. In yet other preferred embodiments, the disorder associated with iron-deficiency is anemia.

Still additional methods of the invention include methods for promoting plant growth and/or survival. These methods include introducing into a plant a nucleic acid encoding an MRT polypeptide

BRIEF DESCRIPTION OF THE DRAWINGS

FIG. 1A depicts the predicted amino acid sequence of the IRT1 protein. Amino acids are numbered on the left beginning with the initiator methionine residue. The signal sequence is underlined, the histidine-glycine repeats that form a metal-binding domain are in boldface and italic, and the putative membrane-spanning domains detected by the TOP PRED II program (Claros, M. G. et al. (1994) Comput. Appl. Biol. Sci. 10: 685–686) are boxed and numbered I-VIII.

FIG. 1B depicts the similarity of the IRT1 amino acid sequence to other plant sequences in the current sequence databases.

FIG. 4 depicts the nucleotide sequence of IRT1.

FIG. 5 depicts the amino acid sequence of IRT1.

Shown are the mean values of two experiments each performed in duplicate. The standard deviation within each experiment was less than 10% of the corresponding mean.

FIG. 11 contains graphs depicting biochemical properties of the low affinity zinc uptake system. Each value represents the mean of two separate experiments each performed in duplicate.

Figure 12:
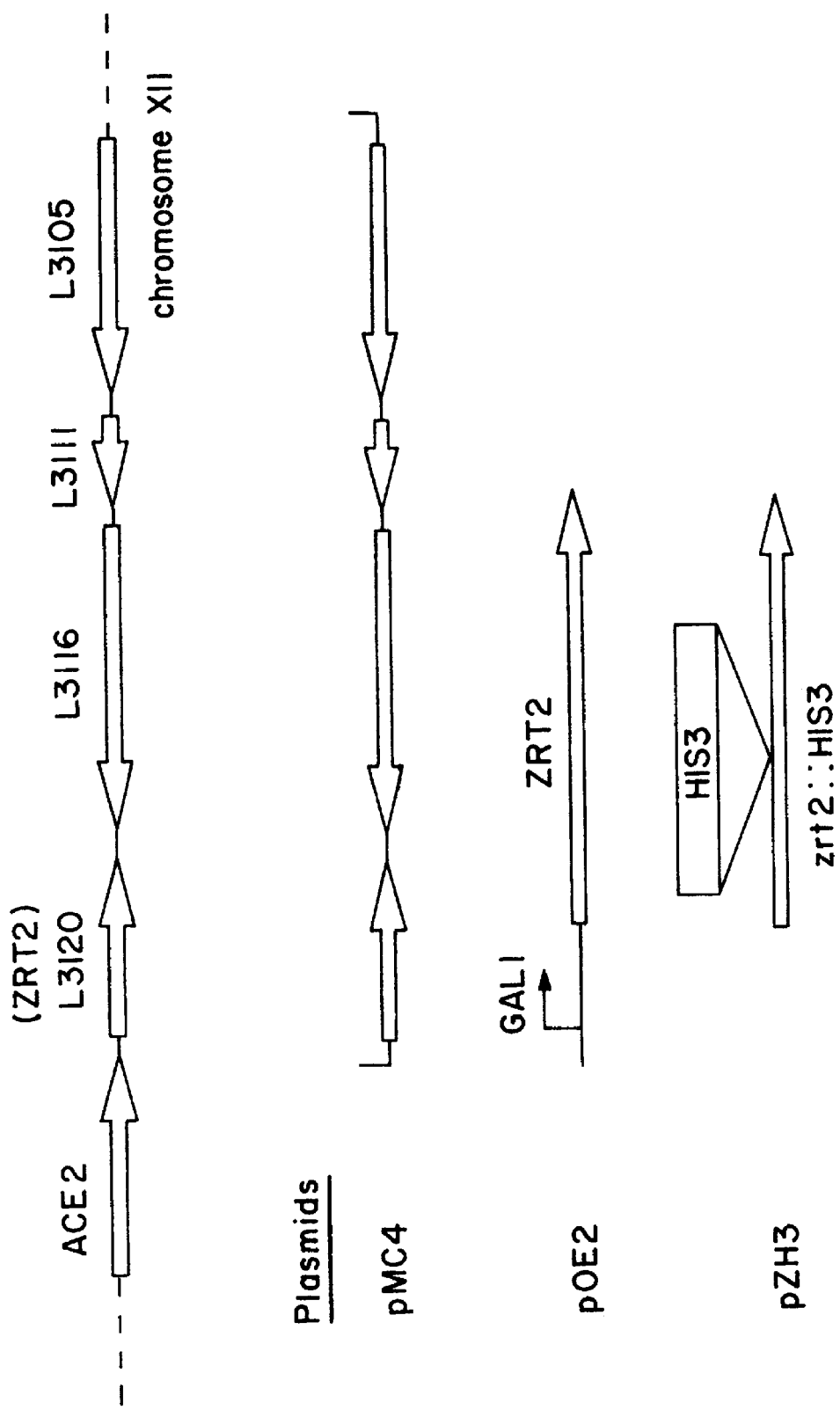

FIG. 12 depicts the chromosomal region of the ZRT2 gene and the plasmids used herein. The top line depicts a segment of yeast chromosome XII with open reading frames indicated by the arrows. The plasmids (pMC4, pOE2, and pZH3) are depicted below and the heterologous promoter in pOE2 is indicated by the arrow labeled GAL1.

Figure 13:
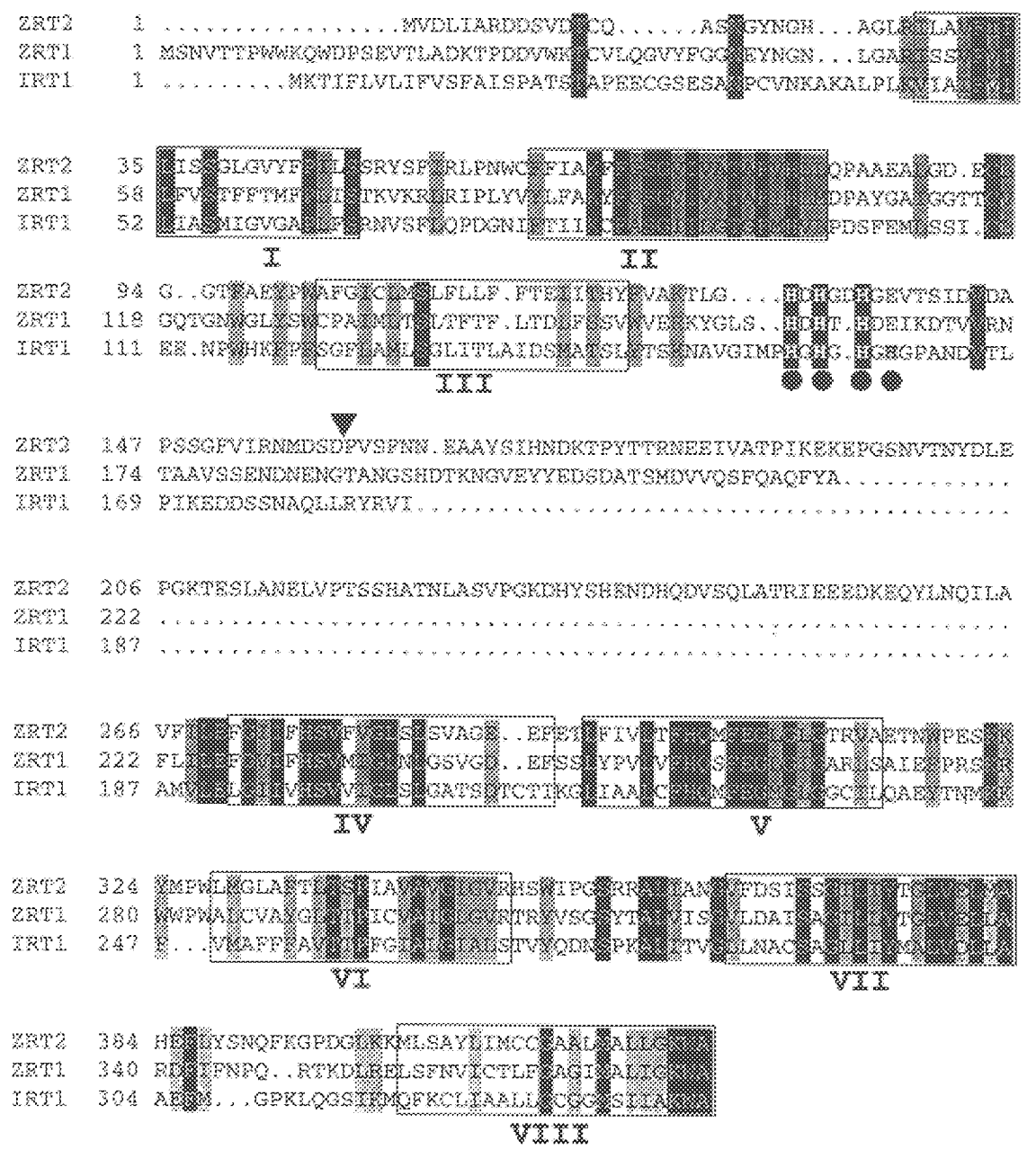

FIG. 13 depicts the predicted amino acid sequence of Zrt2p and its similarity to the amino acid sequences of Zrt1p and Irt1p. The black shading indicates positions of amino acid identity and the gray shading indicates conservative substitutions. The regions of Zrt2p that are predicted to be transmembrane domains are boxed and numbered I through VIII. The predicted transmembrane domains for Zrt1p and Irt1p are similarly located. The black circles indicate the amino acids comprising the putative metal-binding domain and the triangle indicates the position of the HIS3 insertion in the zrt2::HIS3 allele.

Figure 14A:
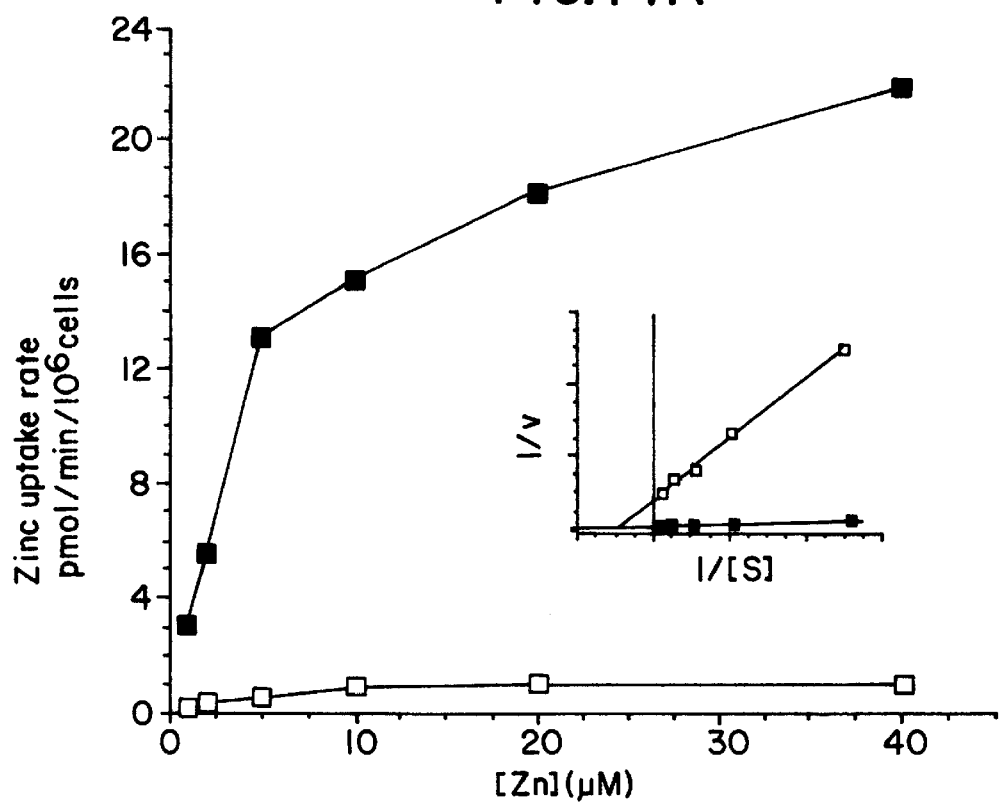

FIG. 14 contains graphs depicting data which demonstrates that ZRT2 overexpression increases the zinc uptake rate. The inset in each frame shows a Lineweaver-Burk reciprocal plot of the corresponding data. Each point represents the mean of two separate experiments each performed in duplicate. The standard deviation of each point was less than 15% of the corresponding mean.

FIG. 15 contains graphs depicting data which demonstrates that the ZRT2 gene is required for low but not high affinity uptake. Each point represents the mean of two separate experiments each performed in duplicate. The standard deviation of each point was less than 20% of the corresponding mean.

FIG. 16 contains graphs depicting effects of the zrt2 mutation on zinc levels required for growth. A representative experiment is shown.

Figure 17A:
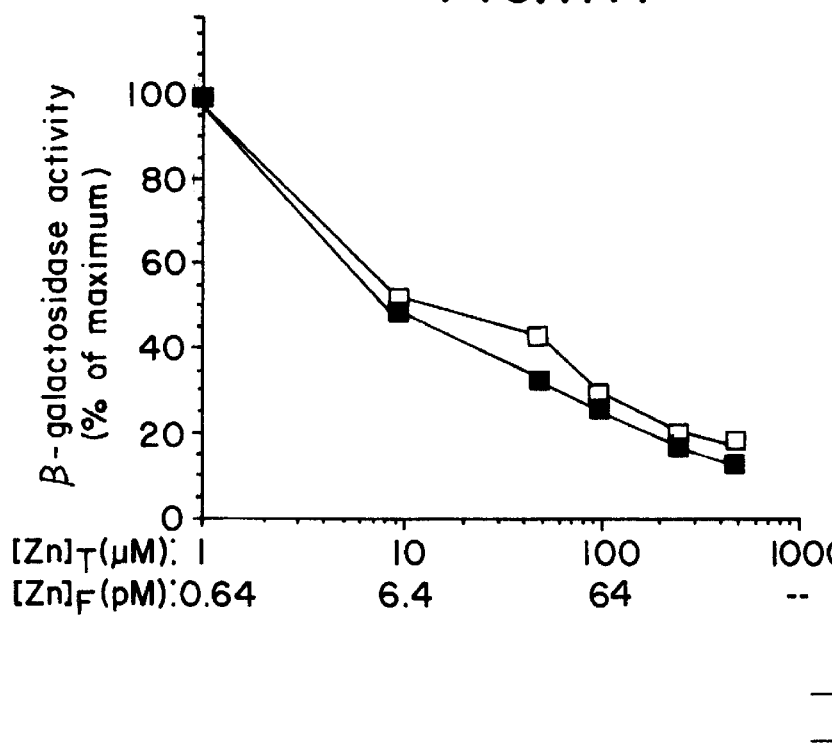

FIG. 17A is a graph depicting the effect of the zrt2 mutation on the regulation of the ZRT1 promoter. Each point represents the mean of three separate experiments and the standard deviation of each point was less than 20% of the corresponding mean.

Figure 17B:
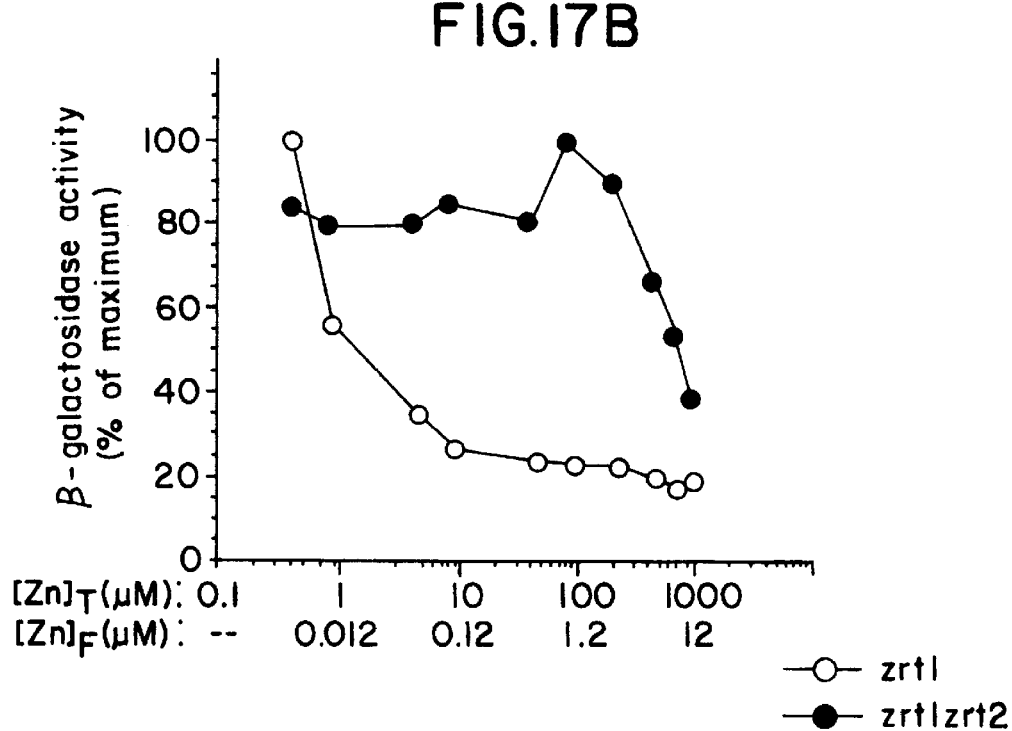

FIG. 17B is a graph depicting the effect of the zrt1 and zrt1zrt2 mutations on the regulation of the ZRT1 promoter. Each point represents the mean of three separate experiments and the standard deviation of each point was less than 20% of the corresponding mean.

FIG. 18 depicts the nucleotide sequence and the corresponding amino acid sequence of ZIP1.

FIG. 19 depicts the nucleotide sequence and the corresponding amino acid sequence of ZIP2.

FIG. 20 depicts the nucleotide sequence and the corresponding amino acid sequence of ZIP3.

FIG. 21 depicts the nucleotide sequence and the corresponding amino acid sequence of ZRT1.

FIG. 22 depicts the nucleotide sequence and the corresponding amino acid sequence of ZRT2.

FIG. 23 depicts the nucleotide sequence and the corresponding amino acid sequence of IRT2.

Figure 24:
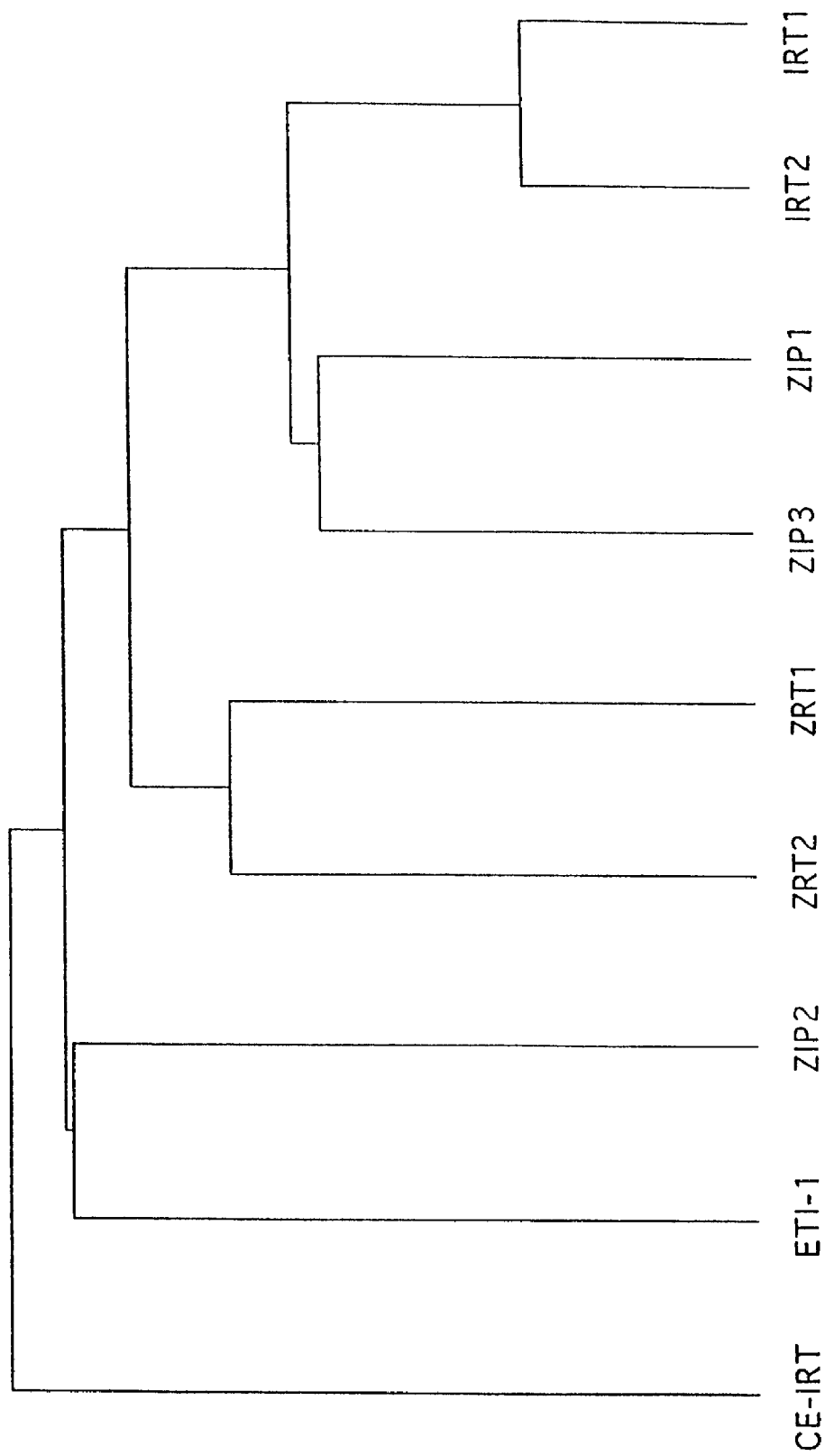

FIG. 24 depicts a dendogram showing total inferred sequence similarities among the deduced amino acid sequences of MRT family members. The tree was constructed using the GCG program PILEUP (Program Manual for the Wisconsin Package, version 8, 1994, Genetics Computer Group, Madison, Wis.). Several sub-families are apparent as groups in the dendogram.

DETAILED DESCRIPTION OF THE INVENTION

The IRT1, iron-regulated transporter, gene of the plant *Arabidopsis thaliana*, encoding an Fe(II) transporter, was cloned by functional expression in a yeast strain defective for iron uptake (GenBankTm™ accession #U27590). *Arabidopsis thaliana*, a common wall cress, is a small member of the mustard or crucifer family. Yeast expressing IRT1 posses a novel Fe(II) uptake activity that is strongly inhibited by Cd. IRT1 is an integral membrane protein with a metal-binding domain. Data base comparisons and Southern blot analysis indicated that IRT1 is a member of a gene family in Arabidopsis. Related sequences were also found in the genomes of rice, yeast, nematodes, and humans. In Arabidopsis, IRT1 is expressed in roots, is induced by iron deficiency, and has altered regulation in plant lines bearing mutations that affect the iron uptake system. These results provide the first molecular insight into iron transport by plants.

Functional expression in yeast has been used to identify a gene that encodes an Fe(II) transporter expressed in the roots of the strategy I plant *Arabidopsis thaliana*. There is a striking similarity between iron uptake in strategy I plants and the mechanism of iron uptake in *Saccharomyces cerevisiae* (Yi, Y. et al. (1994) *Plant Physiol.* 104: 815–820). In *S. cerevisiae*, Fe(III) reductases in the plasma membrane reduce extracellular Fe(III) to Fe(II) (Lesuisse, E. et al. (1989) *J. Gen. Microbiol.* 135: 257–263; Dancis, A. et al. (1990) *Mol. Cell. Biol.* 10: 2294–2301; Eide, D. et al. (1992) *J. Biol. Chem.* 267: 20774–20781). The Fe(II) product is then taken up by either of two uptake systems. One system, with low affinity for substrate, requires the Fe(II) transporter encoded by the FET4 gene (Dix, D. R. et al. (1994) *J. Biol. Chem.* 269: 26092–26099). The second system has high affinity for Fe(II) and is induced under conditions of iron limitation. The high affinity system requires the FET3 multicopper oxidase for activity (Askwith, C. et al. (1994) *Cell* 76: 403–410; Dancis, A. et al. (1994) *Cell* 76: 393–402.). It has been proposed that FET3, as one component of a multisubunit transporter complex, is responsible for oxidizing Fe(II) back to Fe(III) during the transport process. A fet3fet4 double mutant, although viable, is extremely sensitive to iron limitation (Dix, D. R. et al. (1994) *J. Biol. Chem.* 269: 26092–26099). The isolation and characterization of a gene from *A. thaliana*, IRT1, that suppresses the growth defect of afet3fet4 strain on iron-limited media is described herein. IRT1 is the first gene encoding an Fe(II) transporter to be cloned from plants or animals.

Comparisons of the IRT1 amino acid sequence with GenBank™, EMBL, and SWISS-PROT databases identified two additional MRT family members in Arabidopsis. Amino acids 8 through 127 of IRT1 are 72% (86 of 119) identical and 86% similar (i.e., identities plus conservative substitutions) to the predicted amino acid sequence of a cDNA partially sequenced as an EST T04324. Because of this high degree of similarity to IRT1, this gene has been designated IRT2 (SEQ ID NO:13). Furthermore, the carboxyl-terminal 47 amino acids of IRT1 are 45% (21 of 47) identical and 68% similar to the sequence of a partially sequenced open reading frame located downstream of the ferrodoxin-encoding FEDA gene (Somers, D. E. et al. (1990) *Plant Physiol.* 93: 572–577). This gene is referred to as IRT3.

Additional members of the MRT family of polypeptides were identified through a study of zinc uptake in *S. cerevisiae*. The yeast *Saccharomyces cerevisiae* provides an excellent model system in which to study zinc uptake in a eukaryotic cell. Biochemical assays of zinc uptake in yeast indicated that this process was transporter-mediated-i.e., uptake was dependent on time, temperature, and concentration and required metabolic energy (Fuhrmann, G. F. & Rothstein, A. (1968) *Biochim. Biophys. Acta* 163:325–330; White, C. & Gadd, G. M. (1987) *J. Gen. Microbiol.* 133:727–737; and Rothstein, A., Hayes, A., Jennings, D. & Hooper, D. (1958) *J. Gen. Physiol.* 41:585–594). Herein, the presence of two separate zinc uptake systems in *S. cerevisiae* is demonstrated. One system has high affinity for zinc, and its activity markedly increases in zinc-limited cells. The second system has a lower affinity for zinc and is not highly regulated by zinc availability. A gene, ZRT1 (for zinc-regulated transporter) (SEQ ID NO:9), has been characterized and identified because of its significant similarity to IRT1. The results described in greater detail herein indicate that Zrt1p is the zinc transporter protein of the high-affinity uptake system. The ZRT1 is the first influx zinc transporter gene from any organism to be characterized at the molecular level, and it is a member of the MRT family of proteins identified in fungi, nematodes, plants, and humans.

The second system for zinc uptake in yeast has a lower affinity for substrate (apparent $K_m$=10 $\mu M$), and it is active in zinc-replete cells. Low affinity uptake was unaffected by the zrt1mutation, demonstrating that this system is a separate uptake pathway for zinc. Another member of the MRT gene family, ZRT2 (SEQ ID NO:11), was identified in the sequence data bases because of the close sequence similarity of its product to IRT1 and ZRT1. The analysis of ZRT2 demonstrates that this gene encodes the transporter protein of the low affinity system.

Complementation studies using zrt1zrt2 yeast strains allowed for identification of the three additional MRT family members ZIP1 (SEQ ID NO:3), ZIP2 (SEQ ID NO:5) and ZIP3 (SEQ ID NO:7).

Amino acid and nucleotide sequence identities between different MRT family members are outlined in Tables 1 and 2 below.

TABLE 1

Amino Acid Similarities and Identities Among MRT Family Members

| | IDENTITY | | | | | | | SIMILARITY | |
|---|---|---|---|---|---|---|---|---|---|
| | IRT1 | IRT2 | ZIP1 | ZIP2 | ZIP3 | ZRT1 | ZRT2 | C.E.I RT1 | ETI-1 |
| IRT1 | — | 84.4 | 67.2 | 53.0 | 65.6 | 54.4 | 64.9 | 47.2 | 53.9 |
| IRT2 | 70.3 | — | 62.4 | 49.5 | 64.8 | 51.8 | 60.2 | 49.8 | 52.9 |
| ZIP1 | 43.5 | 41.7 | — | 51.2 | 69.9 | 57.6 | 61.5 | 47.9 | 55.9 |
| ZIP2 | 22.3 | 21.5 | 19.1 | — | 53.9 | 49.6 | 55.2 | 47.5 | 55.2 |
| ZIP3 | 47.7 | 44.3 | 49.1 | 23.9 | — | 55.9 | 60.6 | 45.9 | 53.9 |
| ZRT1 | 29.5 | 26.0 | 28.7 | 20.6 | 30.0 | — | 67.0 | 50.6 | 52.0 |
| ZRT2 | 34.5 | 35.2 | 32.6 | 23.2 | 37.7 | 43.8 | — | 52.2 | 55.9 |
| C.E.I RT1 | 20.8 | 20.8 | 19.8 | 23.2 | 21.8 | 20.0 | 20.3 | — | 51.0 |
| ETI-1 | 21.3 | 22.8 | 23.6 | 23.8 | 23.6 | 23.0 | 22.7 | 29.3 | — |

TABLE 2

Nucleotide Identity Values for MRT Family Members

| | IDENTITY | | | | | | | |
|---|---|---|---|---|---|---|---|---|
| | IRT1 | IRT2 | ZIP1 | ZIP2 | ZIP3 | ZRT1 | ZRT2 | ETI-1 |
| IRT1 | — | | | | | | | |
| IRT2 | 73.1 | — | | | | | | |
| ZIP1 | 51.7 | 50.7 | — | | | | | |
| ZIP2 | 41.4 | 41.0 | 41.9 | — | | | | |
| ZIP3 | 54.4 | 53.0 | 57.7 | 42.5 | — | | | |
| ZRT1 | 43.6 | 44.7 | 41.5 | 39.7 | 46.9 | — | | |
| ZRT2 | 44.4 | 45.3 | 44.5 | 40.2 | 43.9 | 44.6 | — | |
| ETI-1 | 40.1 | 40.5 | 43.8 | 41.2 | 40.0 | 42.0 | 40.6 | — |

Accordingly, this invention pertains to MRT polypeptides and to active portions or fragments thereof, such as peptides having MRT bioactivity. The phrases "an activity of MRT" or "having an MRT bioactivity" are used interchangeably herein to refer to molecules such as proteins, polypeptides, and peptides which have one or more of the following functional characteristics:

(1) the MRT polypeptide has the ability to transport one or more of the following metals: Fe, e.g., Fe(II), Cd, Co, Mn, Pb, Hg and Zn;

(2) the MRT polypeptide has the ability to bind one or more of the following metals: Fe, e.g., Fe(II), Cd, Co, Mn, Pb, Hg and Zn;

(3) the MRT polypeptide has affinity for one or more of the following metals: Fe, e.g., Fe(II), Cd, Co, Mn, Pb, Hg and Zn;

(4) the MRT polypeptide has the ability to suppress the growth defect of afet3fet4 yeast strain;

(5) the MRT polypeptide has the ability to uptake one of the following metals: Fe, e.g., Fe(II), Cd, Co, Mn, Pb, Hg and Zn;

(6) the MRT polypeptide has the ability to modulate metal concentration in a biological sample; and (7) the MRT polypeptide has the ability to suppress the growth defect of a zrt1zrt2 yeast strain.

Various aspects of the invention are described in further detail in the following subsections:

I. Isolated MRT Nucleic Acid Molecules

One aspect of this invention pertains to isolated nucleic acid molecules that encode a novel MRT polypeptide, such as an *A. thaliana* IRT1 polypeptide, an *A. thaliana* IRT2 polypeptide, an *A. thaliana* ZIP1 polypeptide, an *A. thaliana* ZIP2 polypeptide, an *A. thaliana* ZIP3 polypeptide, portions or fragments of such nucleic acids, or equivalents thereof. The term "nucleic acid molecule" as used herein is intended to include such fragments or equivalents and refers to DNA molecules (e.g., cDNA or genomic DNA) and RNA molecules (e.g., mRNA). The nucleic acid molecule can be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be free of other cellular material.

The term "equivalent" is intended to include nucleotide sequences encoding a functionally equivalent MRT polypeptide or functionally equivalent polypeptide or peptides having an MRT bioactivity. Functionally equivalent MRT polypeptide or peptides include polypeptides which have one or more of the functional characteristics described herein.

Other equivalents of MRT polypeptides include structural equivalents. Structural equivalents of an MRT polypeptide preferably comprise at least one transmembrane domain which has at least about 40%, more preferably at least about 50%, 55%, 60%, 70%, 80% or 90% amino acid sequence identity with an amino acid sequence shown in SEQ ID NO:2, SEQ ID NO:4, SEQ ID NO:6, SEQ ID NO:8, or SEQ ID NO:14 and/or at least one histidine rich domain. Other preferred structural equivalents of MRT polypeptides include a transmembrane domain, a histidine rich domain, a variable loop domain and optionally one or more of the domains present in MRT polypeptides described herein. Preferred nucleic acid molecules of the invention comprise a nucleotide sequence shown in SEQ ID NO:1, SEQ ID NO:3, SEQ ID NO:5, SEQ ID NO:7, or SEQ ID NO:13, a complement, fragment, portion or equivalent thereof.

In one embodiment, the invention pertains to a nucleic acid molecule which is a naturally occurring form of a nucleic acid molecule encoding an MRT polypeptide, such as an MRT polypeptide having an amino acid sequence shown in SEQ ID NO:2, SEQ ID NO:4, SEQ ID NO:6, SEQ ID NO:8, or SEQ ID NO:14. A naturally occurring form of a nucleic acid encoding MRT is derived from a mammal, e.g., a human, yeast, nematodes or plants, e.g., strategy I or a strategy II plants, e.g., *Arabidopsis thaliana*, rice, broccoli, tomato and mustard. Such naturally occurring equivalents can be obtained, for example, by screening a cDNA library, prepared with RNA from a mammal, with a nucleic acid molecule having a sequence shown in SEQ ID NO:1, SEQ ID NO:3, SEQ ID NO:5, SEQ ID NO:7, or SEQ ID NO:13 under high stringency hybridization conditions. Such conditions are further described herein.

Also within the scope of the invention are nucleic acids encoding natural variants and isoforms of MRT polypeptides, such as splice forms. Such natural variants are also within the scope of the invention.

In a preferred embodiment, the nucleic acid molecule encoding an MRT polypeptide is a cDNA. Preferably, the nucleic acid molecule is a cDNA molecule consisting of at least a portion of a nucleotide sequence encoding a polypeptide as shown in SEQ ID NO:2, SEQ ID NO:4, SEQ ID NO:6, SEQ ID NO:8, or SEQ ID NO:14. Preferred nucleic acid molecules encode polypeptides that have at least about 40%, preferably at least about 42%, 45%, 47%, 50%, more preferably at least about 52%, and most preferably at least about 55%, 60%, 70%, 80%, 90%, 95%, 97%, 98% or more amino acid sequence identity over the entire sequence with the amino acid sequence shown in SEQ ID NO:2, SEQ ID NO:4, SEQ ID NO:6, SEQ ID NO:8, or SEQ ID NO:14. A preferred portion of the cDNA molecule of SEQ ID NO:1 includes the coding region of the molecule (i.e., nucleotides 18–1034). Other preferred portions include those which code for domains of MRT, such as the transmembrane domains,e.g., the eight transmembrane domains of IRT1, the histidine rich domains, e.g., the four histidine rich domains of IRT1, or any combination thereof.

In another embodiment, the nucleic acid of the invention encodes an MRT polypeptide or an active portion or fragment thereof having an amino acid sequence shown in SEQ ID NO:2, SEQ ID NO:4, SEQ ID NO:6, SEQ ID NO:8, or SEQ ID NO:14. In yet another embodiment, preferred nucleic acid molecules encode a polypeptide having an amino acid sequence identity of at least about 40%, preferably at least about 42%, 45%, 47%, 50%, more preferably at least about 52%, and most preferably at least about 55%, 60%, 70%, 80%, 90%, 95%, 97%, 98% or more over the entire sequence with an amino acid sequence shown in SEQ ID NO:2, SEQ ID NO:4, SEQ ID NO:6, SEQ ID NO:8, or SEQ ID NO:14. Nucleic acid molecules which encode peptides having an amino acid sequence identity of at least about 93%, more preferably at least about 95%, and most preferably at least about 98–99% over the entire sequence with a sequence set forth in SEQ ID NO:2, SEQ ID NO:4, SEQ ID NO:6, SEQ ID NO:8, or SEQ ID NO:14 are also within the scope of the invention. Homology, used interchangeably herein with the term "identity" refers to sequence similarity between two protein (peptides) or between two nucleic acid molecules. Homology or identity can be determined by comparing a position in each sequence which may be aligned for purposes of comparison. When a position in the compared sequences is occupied by the same nucleotide base or amino acid, then the molecules are homologous, or identical, at that position. A degree (or percentage) of homology between sequences is a function of the number of matching or homologous positions shared by the sequences.

Isolated nucleic acids encoding a peptide having an MRT bioactivity, as described herein, and having a sequence which differs from a nucleotide sequence shown in SEQ ID NO:1, SEQ ID NO:3, SEQ ID NO:5, SEQ ID NO:7, or SEQ ID NO:13 due to degeneracy in the genetic code are also within the scope of the invention. Such nucleic acids encode functionally equivalent peptides (e.g., having an MRT bioactivity) or structurally equivalent polypeptides but differ in sequence from the sequence of SEQ ID NO:2, SEQ ID NO:4, SEQ ID NO:6, SEQ ID NO:8, or SEQ ID NO:14 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of an MRT polypeptide (especially those within the third base of a codon) may result in "silent" mutations in the DNA which do not affect the amino acid encoded. However, it is expected that DNA sequence polymorphisms that do lead to changes in the amino acid sequences of the MRT polypeptide will exist within a population. It will be appreciated by one skilled in the art that these variations in one or more nucleotides (up to about 3–4% of the nucleotides) of the nucleic acids encoding peptides having the activity of an MRT polypeptide may exist among different plant species or individuals within a population due to natural allelic variation. Any and all such nucleotide variations and resulting amino acid polymorphisms are within the scope of the invention. Furthermore, there are likely to be isoforms or family members of the MRT polypeptide family in addition to those described herein. Such isoforms or family members are defined as proteins related in function and amino acid sequence to an MRT polypeptide, but encoded by genes at different loci. Such isoforms or family members are within the scope of the invention. Additional members of the MRT polypeptide family can be isolated by, for example, screening a library of interest under low stringency conditions described herein or by screening or amplifying with degenerate probes derived from highly conserved amino acids sequences, for example, from the amino acid sequence in SEQ ID NO:2, SEQ ID NO:4, SEQ ID NO:6, SEQ ID NO:8, or SEQ ID NO:14. Alternatively, other members of the MRT polypeptide family can be isolated using one or more of the following techniques. For example, a genomic library from several other dicots, e.g., tomato, broccoli or mustard, can be screened to obtain genes of the MRT family. Positive clones are then analyzed and sequenced to obtain additional family members.

A "fragment" or "portion" of a nucleic acid encoding an MRT polypeptide is defined as a nucleotide sequence having fewer nucleotides than the nucleotide sequence encoding the entire amino acid sequence of an MRT polypeptide, such as an *A. thaliana* IRT1, an *A. thaliana* IRT2, an *A. thaliana* ZIP1, an *A. thaliana* ZIP2, or an A. thaliana ZIP3. A fragment or portion of a nucleic acid molecule is at least about 20 nucleotides, preferably at least about 30 nucleotides, more preferably at least about 40 nucleotides, even more preferably at least about 50 nucleotides in length. Also within the scope of the invention are nucleic acid fragments which are at least about 60, 70, 80, 90, 100 or more nucleotides in length. Preferred fragments or portions include fragments which encode a polypeptide having an MRT bioactivity as described herein. To identify fragments of portions of the nucleic acids encoding fragments or portions of polypeptides which have an MRT bioactivity, several different assays can be employed. For example, to determine the metal uptake activity of MRT peptides, commonly practiced metal uptake activity studies, for example, those described in the Examples section herein can be performed to obtain MRT peptides which transport, for example, Fe, e.g., Fe(II), Cd, Co, Mn, Pb, Hg and/or Zn.

Another aspect of the invention provides a nucleic acid which hybridizes under high or low stringency conditions to a nucleic acid which encodes a peptide having all or a portion of an amino acid sequence shown in SEQ ID NO:2, SEQ ID NO:4, SEQ ID NO:6, SEQ ID NO:8, or SEQ ID NO:14. Appropriate stringency conditions which promote DNA hybridization, for example, 6.0× sodium chloride/sodium citrate (SSC) at about 45° C., followed by a wash of 2.0× SSC at 50° C. are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 25 ° C. to a high stringency of about 0.2×SSC at 65° C. In addition, the temperature in the wash step can be increased from low stringency conditions at room temperature, about 22° C., to high stringency conditions, at about 65° C. Preferably, an isolated nucleic acid molecule of the invention that hybridizes under stringent conditions to the sequence of SEQ ID NO:1, SEQ ID NO:3, SEQ ID NO:5, SEQ ID NO:7, or SEQ ID NO:13 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural MRT polypeptide.

In addition to naturally-occurring allelic variants of the MRT sequence that can exist in the population, the skilled artisan will further appreciate that changes can be introduced by mutation into the nucleotide sequence of SEQ ID NO:1, SEQ ID NO:3, SEQ ID NO:5, SEQ ID NO:7, or SEQ ID NO:13 thereby leading to changes in the amino acid sequence of the encoded MRT polypeptide, without altering the functional ability of the MRT polypeptide. For example, nucleotide substitutions leading to amino acid substitutions at "non-essential" amino acid residues can be made in the sequence of SEQ ID NO:1, SEQ ID NO:3, SEQ ID NO:5, SEQ ID NO:7, or SEQ ID NO:13. A "non-essential" amino acid residue is a residue that can be altered from the wild-type sequence of MRT (e.g., the sequence of SEQ ID NO:2, SEQ ID NO:4, SEQ ID NO:6, SEQ ID NO:8, or SEQ ID NO:14) without altering the MRT activity of the polypeptide.

An isolated nucleic acid molecule encoding an MRT polypeptide homologous to the protein of SEQ ID NO:2, SEQ ID NO:4, SEQ ID NO:6, SEQ ID NO:8, or SEQ ID NO:14 can be created by introducing one or more nucleotide substitutions, additions or deletions into the nucleotide sequence of SEQ ID NO:1, SEQ ID NO:3, SEQ ID NO:5, SEQ ID NO:7, or SEQ ID NO:13 such that one or more amino acid substitutions, additions or deletions are introduced into the encoded polypeptide. Mutations can be introduced into SEQ ID NO:1, SEQ ID NO:3, SEQ ID NO:5, SEQ ID NO:7, or SEQ ID NO:13 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in MRT is preferably replaced with another amino acid residue from the same side chain family. Alternatively, in another embodiment, mutations can be introduced randomly along all or part of an MRT coding sequence, such as by saturation mutagenesis, and the resultant mutants can be screened for proteolytic activity to identify mutants that retain proteolytic activity. Following mutagenesis of the nucleotide sequence of SEQ ID NO:1, SEQ ID NO:3, SEQ ID NO:5, SEQ ID NO:7, or SEQ ID NO:13, the encoded polypeptide can be expressed recombinantly and activity of the protein can be determined.

In addition to the nucleic acid molecules encoding MRT polypeptides described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MRT coding strand, or to only a portion thereof. In one embodiment, an antisense nucleic acid molecule is antisense to a "coding region" of the coding strand of a nucleotide sequence encoding MRT. The term "coding region" refers to the region of the nucleotide sequence comprising codons which are translated into amino acid residues (e.g., the entire coding region of SEQ ID NO:1, SEQ ID NO:3, SEQ ID NO:5, SEQ ID NO:7, or SEQ ID NO:13). In another embodiment, the antisense nucleic acid molecule is antisense to a "noncoding region" of the coding strand of a nucleotide sequence encoding MRT. The term "noncoding region" refers to 5' and 3' sequences which flank the coding region that are not translated into amino acids (i.e., also referred to as 5' and 3' untranslated regions).

Given the coding strand sequences encoding MRT polypeptides disclosed herein (e.g., SEQ ID NO:1, SEQ ID NO:3, SEQ ID NO:5, SEQ ID NO:7, or SEQ ID NO:13), antisense nucleic acids of the invention can be designed according to the rules of Watson and Crick base pairing. The antisense nucleic acid molecule can be complementary to the entire coding region of MRT mRNA, but more preferably is an oligonucleotide which is antisense to only a portion of the coding or noncoding region of MRT mRNA. For example, the antisense oligonucleotide can be complementary to the region surrounding the translation start site of MRT mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for an MRT-encoding nucleic acid can be designed based upon the nucleotide sequence of an MRT cDNA disclosed herein (i.e., SEQ ID NO:1, SEQ ID NO:3, SEQ ID NO:5, SEQ ID NO:7, or SEQ ID NO:13). See, e.g., Cech et al. U.S. Pat. No. 4,987,071; and Cech et al. U.S. Pat. No. 5,116,742. Alternatively, MRT mRNA can be used to select a catalytic RNA having a specific ribonuclease activity from a pool of RNA molecules. See, e.g., Bartel, D. and Szostak, J. W. (1993) *Science* 261: 1411–1418.

The nucleic acid molecules of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

II. Recombinant Expression Vectors and Host Cells

Another aspect of the invention pertains to vectors, preferably expression vectors, containing a nucleic acid encoding MRT (or a portion or fragment thereof). As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MRT polypeptides, mutant forms of MRT, fusion proteins, etc.).

The recombinant expression vectors of the invention can be designed for expression of MRT in prokaryotic or eukaryotic cells. For example, MRT can be expressed in bacterial cells such as *E. coli*, insect cells (using baculovirus expression vectors) yeast cells, plant cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes:1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nuc. Acids Res.* 20:2111–2118). Such alteration of nucleic acid sequences of the invention can be carried out by standard DNA synthesis techniques.

In another embodiment, the MRT expression vector is a yeast expression vector. Examples of vectors for expression in yeast *S. cerivisae* include pYepSec1 (Baldari. et al. (1987) *Embo J.* 6:229–234), pMFa (Kurjan and Herskowitz (1982) *Cell* 30:933–943), pJRY88 (Schultz et al. (1987) *Gene* 54:113–123), and pYES2 (Invitrogen Corporation, San Diego, Calif.).

Alternatively, MRT can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow, V. A., and Summers, M. D. (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), cauliflower mosaic virus promoter, e.g., CaMV35S, and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

In one embodiment, a recombinant expression vector containing DNA encoding a MRT fusion protein is produced. An MRT fusion protein can be produced by recombinant expression of a nucleotide sequence encoding a first polypeptide peptide having an MRT bioactivity and a nucleotide sequence encoding a second polypeptide having an amino acid sequence unrelated to an amino acid sequence which has at least about 40% or more amino acid sequence identity with an amino acid sequence shown in SEQ ID NO:2, SEQ ID NO:4, SEQ ID NO:6, SEQ ID NO:8, or SEQ ID NO:14. In many instances, the second polypeptide correspond to a moiety that alters a characteristic of the first peptide, e.g., its solubility, affinity, stability or valency. For example, an MRT polypeptide of the present invention can be generated as a glutathione-S-transferase (GST- fusion protein). Such GST fusion proteins can enable easy purification of the MRT polypeptide, such as by the use of glutathione-derivatized matrices (see, for example, *Current Protocols in Molecular Biology*, eds. Ausabel et al. (N.Y.: John Wiley & Sons, 1991)). Preferably the fusion proteins of the invention are functional in a two hybrid assay. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MRT RNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MRT polypeptide can be expressed in bacterial cells such as *E. coli*, insect cells, yeast, plant or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding MRT or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an MRT polypeptide. Accordingly, the invention further provides methods for producing MRT polypeptides using the host cells of the invention. In one embodiment, the method comprises culturing the host cell of invention (into which a recombinant expression vector encoding MRT has been introduced) in a suitable medium until MRT is produced. In another embodiment, the method further comprises isolating MRT from the medium or the host cell.

The host cells of the invention can also be used to produce transgenic plants. As used herein, the term "transgenic" refers to a cell, group of cells, or organism, e.g., plant or animal, which includes a DNA sequence which is inserted by artifice therein. If the DNA sequence is inserted into a cell, the sequence becomes part of the genome of the organism which develops from that cell. For example, the transgenic organisms are generally transgenic plants and the DNA transgene is inserted artificially into the nuclear or plastidic genome. As used herein, the term "transgene" refers to any piece of DNA which is artificially inserted into a cell, group of cells, or organism, e.g., plant or animal, and becomes a part of the genome of the organism which develops from that cell. Such a transgene can include a gene which is partly or entirely heterologous to the transgenic organism, or can include a gene homologous to an endogenous gene of the organism.

For example, in one embodiment, a host cell of the invention is a plant cell, e.g., a protoplast, into which MRT-coding sequences have been introduced. As used herein, a "plant cell" refers to any self-propagating cell bounded by a semi-permiable membrane and containing a plastid. Such a cell requires a cell wall if further propagation is desired. For example, plant cells of the invention include algae, cyanobacteria, seed suspension cultures, embryos, meristematic regions, callus tissue, leaves, roots, shoots, gametophytes, sporophytes, pollen, and microspores. As used herein, the term "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The transformation of plants in accordance with the invention can be carried out in essentially any of the various ways known to those skilled in the art of plant molecular biology. See, in general, *Methods in Enzymology* Vol 153 ("Recombinant DNA Part D") 1987, Wu and Grossman Eds., Academic Press and European Patent Application EP 693554.

Selection of an appropriate vector is relatively simple, as the constraints are minimal. The minimal traits of the vector are that the desired nucleic acid sequence be introduced in a relatively intact state. Thus any vector which produces a plant carrying the introduced DNA sequence is sufficient. Also, any vector which introduces a substantially intact RNA which can ultimately be converted into a stably maintained DNA sequence can be used to transform a plant cell.

Even a naked piece of DNA confers the properties of this invention, though at low efficiency. The decision as to whether to use a vector, or which vector to use, is determined by the method of transformation selected.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, minichromosome vectors, and viral vectors, including the possibility of RNA forms of the gene sequences. The selection of vectors and methods to construct them are commonly known to persons of ordinary skill in the art and are described in general technical references (*Methods in Enzymology* Vol 153 ("Recombinant DNA Part D") 1987, Wu and Grossman Eds., Academic Press).

In one embodiment, the foreign nucleic acid is mechanically transferred by microinjection directly into plant cells by use of micropipettes. Alternatively, the foreign nucleic acid can be transferred into the plant cell by using polyethylene glycol. This forms a precipitation complex with the genetic material that is taken up by the cell (Paszkowski et al. (1984) *EMBO J.* 3:2712–22).

In another embodiment, foreign nucleic acid can be introduced into the plant cells by electroporation (From et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can also be used as a vector for introducing the foreign nucleic acid into plant cells (Hohn et al. (1982) "Molecular Biology of Plant Tumors," Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of foreign nucleic acid into plant cells is high velocity ballistic penetration by small particles with the nucleic acid either within the matrix of small beads or particles, or on the surface (Klein et al. (1987) *Nature* 327:70–73). Although typically only a single introduction of a new nucleic acid segment is required, this method particularly provides for multiple introductions.

A preferred method of introducing the nucleic acids into plant cells is to infect a plant cell, an explant, a meristem or a seed with *Agrobacterium tumefaciens* transformed with the nucleic acid. Under appropriate conditions known in the art, the transformed plant cells are grown to form shoots, roots, and develop further into plants. The nucleic acids can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 233:496–498; Fraley et al. (1983) *Proc. Natl. Acad. Sci. USA* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without affecting its transferring ability. By removing the tumor-causing genes so that they no longer interfere, the modified Ti plasmid can then be used as a vector for the transfer of the gene constructs of the invention into an appropriate plant cell.

There are presently at least three different ways to transform plant cells with Agrobacterium: (1) co-cultivation of Agrobacterium with cultured isolated protoplasts; (2) transformation of cells or tissues with Agrobacterium; or (3) transformation of seeds, apices or meristems with Agrobacterium. The first method requires an established culture system that allows culturing protoplasts and plant regeneration from cultured protoplasts. The second method requires that the plant cells or tissues can be transformed by Agrobacterium and that the transformed cells or tissues can be induced to regenerate into whole plants. The third method requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and can be used in this invention.

All plants from which protoplasts can be isolated and cultured to give whole regenerated plants can be transformed by the present invention so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Practically all plants can be regenerated from cultured cells or tissues. The term "regeneration" as used herein, means growing a whole plant from a plant cell, a group of plant cells, a plant part or a plant piece (e.g. from a protoplast, callus, or tissue part) (*Methods in Enzymology* Vol. 153 ("Recombinant DNA Part D") 1987, Wu and Grossman Eds., Academic Press; also *Methods in Enzymology*, Vol. 118; and Klee et al., (1987) *Annual Review of plant Physiology*, 38:467–486).

Plant regeneration from cultural protoplasts is described in Evans et al., "Protoplasts Isolation and Culture," *Handbook of plant Cell Cultures* 1: 124–176 (MacMillan Publishing Co. New York 1983); M. R. Davey, "Recent Developments in the Culture and Regeneration of Plant Protoplasts," *Protoplasts* (1983)-Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)-Lecture Proceedings, pp. 31–41, (Birkhauser, Basel 1983); and H. Binding, "Regeneration of Plants," *Plant Protoplasts*, pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants are propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants are self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

However, any additional attached vector sequences which confers resistance to degradation of the nucleic acid fragment to be introduced, which assists in the process of genomic integration or provides a means to easily select for those cells or plants which are transformed are advantageous and greatly decrease the difficulty of selecting useable transgenic plants or plant cells.

Selection of transgenic plants or plant cells is typically be based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) *The Flavonoids*, Vols. 1 and 2, [Acad. Press]). Appropriate plants are selected and further evaluated. Methods for generation of genetically engineered plants are further described in U.S. Pat. No. 5,283,184, U.S. Pat. No. 5, 482,852, and European Patent Application EP 693 554.

An example of a commercial application of the transgenic plants of the invention is in agriculture. Iron is an essential nutrient for crop plants because it is required for the activity of iron-containing proteins involved in photosynthesis and respiration. Although iron is abundant in the soil, its acquisition can be difficult under aerobic conditions because it is very insoluble at moderate pH. This issue is important in agriculture because a third of the world's soils are iron-deficient. Therefore, understanding how plants accumulate iron is critical for increased production of crops that would themselves be richer sources of iron in foods. The ability to develop transgenic plants, through manipulation of IRT1 gene and other members of the MRT family, that are more efficient in extracting iron from soil has important agricultural implications.

A second example of a commercial application of the transgenic plants of the invention is in environmental pollution remediation. Removal of toxic metals from contaminated sites is particularly difficult. Unlike organic pollutants, metal pollutants cannot be biodegraded. The current method of removing metals from contaminated sites is excavation, removal of the soil, and burial in a hazardous waste site. Phytoremediation, the technique of using plants to extract metals from soil, is a more economical and environmentally-safe alternative. Genetically engineered plants of the present invention that are created to be metal specific present great potential for this technology. IRT1 or other members of the MRT family can be manipulated in a plant species to allow high-level accumulation of a specific toxic metal from a contaminated soil.

III. Isolated MRT Polypeptides and Anti-MRT Antibodies

Another aspect of the invention pertains to isolated MRT polypeptides and active fragments or portions thereof, i.e., peptides having an MRT activity, such as *A. thaliana* IRT1, *A. thaliana* IRT2, *A. thaliana* ZIP3, *A. thaliana* ZIP2 or *A. thaliana* ZIP1. This invention also provides a preparation of MRT or fragment or portion thereof. An "isolated"polypeptide is substantially free of cellular material or culture medium when produced by recombinant DNA techniques, or chemical precursors or other chemicals when chemically synthesized. In a preferred embodiment, the MRT polypeptide has an amino acid sequence shown in SEQ ID NO:2, SEQ ID NO:4, SEQ ID NO:6, SEQ ID NO:8 or SEQ ID NO:14. In other embodiments, the MRT polypeptide is substantially homologous or identical to SEQ ID NO:2, SEQ ID NO:4, SEQ ID NO:6, SEQ ID NO:8 or SEQ ID NO:14 and retains the functional activity of the polypeptide of SEQ ID NO:2, SEQ ID NO:4, SEQ ID NO:6, SEQ ID NO:8 or SEQ ID NO:14 yet differs in amino acid sequence due to natural allelic variation or mutagenesis, as described in detail in subsection I above. Accordingly, in another embodiment, the MRT polypeptide is a polypeptide which comprises an amino acid sequence with at least about 40% overall amino acid identity with the amino acid sequence of SEQ ID NO:2, SEQ ID NO:4, SEQ ID NO:6, SEQ ID NO:8 or SEQ ID NO:14. Preferably, the polypeptide is at least about 40%, preferably at least about 42%, 45%, 47%, 50%, more preferably at least about 52%, and most preferably at least about 55%, 60%, 70%, 80%, 90%, 95%, 97% or 98%–99% identical over the entire sequence to SEQ ID NO:2, SEQ ID NO:4, SEQ ID NO:6, SEQ ID NO:8 or SEQ ID NO:14.

An isolated MRT polypeptide can comprise the entire amino acid sequence of SEQ ID NO:2, SEQ ID NO:4, SEQ ID NO:6, SEQ ID NO:8 or SEQ ID NO:14, or a biologically active portion or fragment thereof. For example, an active portion of MRT can comprise a selected domain of MRT, such as the transmembrane domain or the histidine rich domain. Moreover, other biologically active portions, in which other regions of the protein are deleted, can be prepared by recombinant techniques and evaluated for an MRT bioactivity as described in detail herein. For example, a peptide having an MRT bioactivity can differ in amino acid sequence from the sequence depicted in SEQ ID NO:2, SEQ ID NO:4, SEQ ID NO:6, SEQ ID NO:8 or SEQ ID NO:14 but such differences result in a peptide which functions in the same or similar manner as MRT. Thus, peptides having the ability to modulate metal transport, e.g., Fe, e.g., Fe(II), Co, Cd, Mn, Pb, Hg and/or Zn transport, and which preferably have at least one transmebrane domain and/or at least one histidine rich domain are within the scope of this invention. Preferred peptides of the invention include those which are further capable of reducing Fe(III) to the more soluble Fe(II) form.

A peptide can be produced by modification of the amino acid sequence shown in SEQ ID NO:2, SEQ ID NO:4, SEQ ID NO:6, SEQ ID NO:8 or SEQ ID NO:14 such as a substitution, addition or deletion of an amino acid residue which is not directly involved in the function of MRT. For example, in order to enhance stability and/or reactivity, the polypeptides or peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Modifications of proteins or peptides or portions thereof can also include reduction/alkylation (Tarr in: *Methods of Protein Microcharacterization*, J. E. Silver ed. Humana Press, Clifton, N.J., pp 155–194 (1986)); acylation (Tarr, supra); chemical coupling to an appropriate carrier (Mishell and Shiigi, eds, Selected *Methods in Cellular Immunology*, W H Freeman, San Francisco, Calif. (1980); U.S. Pat. No. 4,939,239; or mild formalin treatment (Marsh *International Archives of Allergy and Applied Immunology*, 41:199–215 (1971)).

To facilitate purification and potentially increase solubility of proteins or peptides of the invention, reporter group(s) can be added to the peptide backbone. For example, polyhistidine can be added to a peptide to purify the peptide on immobilized metal ion affinity chromatography (Hochuli, E. et al. (1988) *Bio/Technology*, 6:1321–1325). In addition, specific endoprotease cleavage sites can be introduced, if desired, between a reporter group and amino acid sequences of a peptide to facilitate isolation of peptides free of irrelevant sequences.

Peptides of the invention are typically at least 30 amino acid residues in length, preferably at least 40 amino acid residues in length, more preferably at least 50 amino acid residues in length, and most preferably 60 amino acid residues in length. Peptides having MRT activity and including at least 80 amino acid residues in length, at least 100 amino acid residues in length, at least about 200, or at least about 300 or more amino acid residues in length are also within the scope of the invention. Other peptides within the scope of the invention include those encoded by the nucleic acids described herein.

Another embodiment of the invention provides a substantially pure preparation of a peptide having an MRT bioactivity. Such a preparation is substantially free of proteins and peptides with which the peptide naturally occurs in a cell or with which it naturally occurs when secreted by a cell.

The term "isolated" when used to refer to an MRT polypeptide means that the polypeptide is substantially free of cellular material or culture medium when produced by recombinant DNA techniques, or chemical precursors or other chemicals when chemically synthesized.

The peptides and fusion proteins produced from the nucleic acid molecules of the present invention can also be used to produce antibodies specifically reactive with MRT polypeptides. For example, by using a full-length MRT polypeptide, such as an antigen having an amino acid sequence shown in SEQ ID NO:2, SEQ ID NO:4, SEQ ID NO:6, SEQ ID NO:8 or SEQ ID NO:14, or a peptide fragment thereof, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant MRT polypeptide, or fragment or portion thereof or a synthetic peptide fragment. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term "antibody" as used herein is intended to include fragments thereof which are also specifically reactive with a peptide having an MRT activity as described herein. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-MRT polypeptide portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel MRT polypeptides of the invention. See, e.g., Morrison et al. (1985) *Proc. Natl. Acad. Sci. U.S.A.* 81:6851; Takeda et al. (1985) *Nature* 314:452; Cabilly et al., U.S. Pat. No. 4,816,567; Boss et al., U.S. Pat. No. 4,816,397; EP171496; EP173494, GB 2177096. Such chimeric antibodies are less immunogenic in a human subject than the corresponding non-chimeric antibody.

For human therapeutic purposes, the monoclonal or chimeric antibodies specifically reactive with an MRT polypeptide as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) *Science* 229:1202–1207 and by Oi et al. (1986) *BioTechniques* 4:214. Such altered immunoglobulin molecules may be made by any of several techniques known in the art, (e.g., Teng et al. (1983) *Proc. Natl. Acad. Sci. U.S.A.*, 80:7308–7312; Kozbor et al. (1983) *Immunology Today*, 4:7279; Olsson et al. (1982) *Meth. Enzymol.*, 92:3–16), and are preferably made according to the teachings of WO92/06193 or EP 0239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. 5,225,539 to Winter; Jones et al. (1986) *Nature* 321:552–525; Verhoeyan et al. (1988) *Science* 239:1534; and Beidler et al. (1988) *J. Immunol.* 141:4053–4060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with an MRT polypeptide, such as human MRT. Splenocytes from these immunized transgenic mice can then be used to create hybridomas that secrete human monoclonal antibodies specifically reactive with an MRT polypeptide (see, e.g., WO 91/00906; WO 91/10741; WO 92/03918; WO 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman et al. (1993) *Year Immunol* 7:33–40; Tuaillon et al. (1993) *Proc. Natl. Acad. Sci. USA* 90:3720–3724; and Bruggeman et al. (1991) *Eur J Immunol* 21:1323–1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies that bind an MRT polypeptide of the invention (for descriptions of combinatorial antibody display see e.g., Sastry et al. (1989) PNAS 86:5728; Huse et al. (1989) *Science* 246:1275; and Orlandi et al. (1989) PNAS 86:3833). After immunizing an animal with an MRT polypeptide, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. PNAS (1989) 86:3833–3837; Sastry et al., PNAS (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27–9400–01; and the Stratagene SurfZAP™phage display kit, catalog no. 240612), examples of methods and reagents particularly amenable for use in generating a diverse antibody display library can be found in, for example, Ladner et al. U.S. Pat. No. 5,223,409; WO 92/18619; WO 91/17271; WO 92/20791; WO 92/15679; WO 93/01288; WO 92/01047; WO 92/09690; WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4\text{-}Ser)_3$ linker can be used to produce a single chain antibody which can render the display package separable based on antigen affinity. Isolated scFV antibodies immunoreactive with a peptide having activity of an MRT polypeptide can subsequently be formulated into a pharmaceutical preparation for use in the subject method.

Once displayed on the surface of a display package (e.g., filamentous phage), the antibody library is screened with an MRT polypeptide, or peptide fragment thereof, to identify and isolate packages that express an antibody having specificity for the MRT polypeptide. Nucleic acid encoding the selected antibody can be recovered from the display package (e.g., from the phage genome) and subcloned into other expression vectors by standard recombinant DNA techniques.

The polyclonal or monoclonal antibodies of the current invention, such as an antibody specifically reactive with a recombinant or synthetic peptide having an MRT activity can also be used to isolate the native MRT polypeptides from cells. For example, antibodies reactive with the peptide can be used to isolate the naturally-occurring or native form of MRT from, for example, plant cells by immunoaffinity chromatography. In addition, the native form of cross-reactive MRT-like molecules can be isolated from plant cells or other cells by immunoaffinity chromatography with an anti-MRT antibody.

IV. Uses and Methods of the Invention

The invention further pertains to methods for modulating metal concentration in a biological sample containing the metal. These methods include providing a transgenic plant in which expression of an MRT polypeptide is altered and contacting the transgenic plant with the biological sample such that the metal concentration in the biological sample is modulated. The term "modulating" as used herein refers to increasing or decreasing the concentration of a metal in a biological sample. As used herein, the term "metal" includes stable metals and radioactive metals such as iron, lead, chromium, mercury, cadmium, cobalt, barium, nickel, molybdenum, copper, arsenic, selenium, zinc, antimony, beryllium, gold, manganese, silver, thallium, tin, rubidium, vanadium, strontium, yttrium, technecium, ruthenium, palladium, indium, cesium, uranium, plutonium, and cerium. The term "metal" is also intended to include a mixture of two or more metals and mixtures of metals and common organic pollutants such as, for example, lead and chromium in combination with nitrophenol, benzene, and/or alkyl benzyl sulfonates (detergents). As used herein the phrase "biological sample" refers to a material, solid or liquid, in which it is desirable to modulate a metal concentration. Examples of biological samples include metal contaminated liquids such as industrial and residential waste streams, water-treatment plant effluents, ground and surface water, diluted sludge and other aqueous streams containing radioactive and nonradioactive metals, as well as soils or sediments. The soils or sediments can include a variety of soil types having wide ranges of water content, organic matter content, mineral content and metal content. As used herein, the phrase "transgenic plant in which expression of an MRT polypeptide is altered" refers to a transgenic plant in which an MRT polypeptide is misexpressed, e.g., the expression of an MRT polypeptide is enhanced, induced, prevented or suppressed. For example, a transgenic plant in which MRT polypeptide is altered, e.g., by misexpression, can be a metal accumulating plant.

"Misexpression", as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

To measure metal accumulation of a plant in a biological sample, seeds of a particular plant to be tested are grown in a greenhouse, the appropriate metal is administered to the plant and soil, and the roots and shoots harvested for routine determination of biomass and metal content. Chemical analysis of metal content in soils and plants is well characterized. See, e.g., Blincoe et al. (1987) *Comm. Soil. Plant Anal.* 18: 687; Baker et al. (1982) "Atomic Absorption Spectrometry," pp. 13–17 in *Methods of Soil Analysis*, part 2, *Am. Soc. Agron.*, Madison, Wis. Metal in plant tissues is preferably assayed with plasma spectrometry, allowing ashing and acid extraction. Metal remaining in the solution is measured, for example, by atomic absorption or plasma spectrometry. See, e.g., Soltanpour et al. (1982) "Optical emission spectrometry," pp. 29–65 in *Methods of Soil Analysis*, part 2, *Am. Soc. Agron.*, Madison, Wis.

Other methods of the invention include methods for removing a pollutant from soil, e.g., phytoremediation. These methods include contacting the transgenic plant in which expression of an MRT polypeptide is altered with the soil such that the pollutant is removed from the soil, i.e., the concentration of the pollutant in the soil prior to contact with the transgenic plant is greater than the concentration of the pollutant in the soil after contact with the transgenic plant. The term "pollutant" as used herein refers to any metal, e.g., radioactive or nonradioactive metal, that is found in the soil at toxic levels. As used herein, the phrase "toxic levels" refers to the concentration of metal which is higher than the concentration at which these metals naturally occur in the soil. Such toxic levels are usually produced by industries and other pollution centers. For example, metals such as mercury, cobalt, lead, arsenic, cadmium, zinc, copper, alone or in combination with other metals and/or detergents, as described above, are known soil pollutants.

Still other methods of the present invention include methods for treating a disorder associated with metal-deficiency, e.g., iron-deficiency or zinc-deficiency, in a subject. These methods include administering to a subject a therapeutically effective amount of a composition comprising the transgenic plant, or a portion thereof, in which expression of an MRT polypeptide is altered. In a preferred embodiment, the composition is administered in combination with a pharmaceutically acceptable carrier. In another preferred embodiment, the MRT polypeptide is overexpressed. Subjects who can be treated by the method of this invention include living organisms, e.g. mammals, e.g., humans. Examples of preferred subjects are those who have or are susceptible to iron-deficiency or zinc-defficency, e.g., infants and women of childbearing age. As used herein, the phrase "a disorder associated with metal-deficiency" refers to any disease or disorder that results from a negative balance between metal intake and metal loss, e.g., iron intake and iron loss or zinc intake and zinc loss. For example, whenever there is rapid growth, as occurs during infancy, early childhood, adolescence and pregnancy, positive iron balance is difficult to maintain. Iron-deficiency can be the result of low dietary iron content, especially bioavailable iron, while in areas endemic for hookworm, intestinal blood loss secondary to heavy infestation contributes to iron-deficiency in both women and men. More severe forms of iron-deficiency usually result in anemia. In addition to iron, zinc is a metal with great nutritional importance, particularly during periods of rapid growth, due to its intervention in cellular replication as well as in development of the immune response. There is considerable evidence that zinc deficiency in humans is a serious worldwide problem and outweighs the potential problem of accidental, self-imposed, or environmental exposure to zinc excess. Acute deficiency (Henkin et al.. (1975) *Arch Neurol* 322:745–751) and chronic deficiency (Prasad A. S. (1991) *Am J Clin Nutr*

53:403–412) are well-known entities in human populations and are probably much more common than generally recognized. The importance of zinc for human health was first documented in 1963 (Prasad et al. (1963) *J Lab Clin Med* 61:537–549). During the past 25 years, deficiency of zinc in humans due to nutritional factors and several disease states has now been documented throughout the world. Prevalence of zinc deficiency is high in populations that consume large quantities of cereal proteins containing high amounts of phytate, an organic phosphate compound. Alcoholism, malabsorption, sickle cell anemia, chronic renal disease, and other chronically debilitating diseases are known to be predisposing factors for zinc deficiency in humans (Prasad A S, (Prasad, A S, ed.) (1988) *New York:Alan R. Liss* 3–53).

Based upon clinical data and using traditional, epidemiologic techniques, Henkin and Aamodt (Henkin R I, Aamodt R L, (Inglett G E, ed.) (1983) *Washington:American Chemical Society* 83–105) have reclassified zinc deficiency into three syndromes; these are a) acute, b) chronic, and c) subacute zinc deficiency. Acute zinc deficiency is relatively uncommon and follows parenteral hyperalimentation or oral $_L$-histidine administration. Chronic zinc deficiency is more common, usually resulting from chronic dietary lack of zinc. Subacute or latent zinc deficiency is the most common of these syndromes. It is estimated that there are 4 million people in the United States with this syndrome, the initial symptom being dysfunction of taste and olfaction; treatment with exogenous zinc restores taste and smell but this usually requires months before these functions are returned to normal (Henkin et al. (1976) *Am J Med Sci* 272:285–299). Diagnosis of these disorders is most efficacious following oral administration of zinc tracers such as $^{65}$Zn, $^{67}$Zn, or $^{70}$Zn with subsequent evaluation of the kinetics of transfer of the isotope into various body tissues, the formulation of the data by compartmental analysis, and the integration of the data by a systematic model of zinc metabolism.

Clinical symptoms of human zinc-deficiency states exhibit a spectrum ranging from mild to severe and may even be fatal if unrecognized and not corrected (Prasad, A S (Prasad, A S, ed.) (1988) *New York:Alan R. Liss*, 3–53). The clinical manifestations of severely zinc deficient subjects include bullous pustular dermatitis, diarrhea, alopecia, mental disturbances, and intercurrent infections due to cell-mediated immune disorders. These severe signs are seen in patients with acrodermatitis enteropathica secondary to an inborn error of zinc absorption, patients receiving total parenteral nutrition without zinc, and patients receiving penicillamine therapy. Growth retardation, male hypogonadism, skin changes, poor appetite, mental lethargy, abnormal dark adaptation, and delayed wound healing are usual manifestations of moderate deficiency of zinc. Recent studies show that a mild or marginal deficiency of zinc in humans is characterized by neurosensory changes, oligospermia in males, decreased serum testosterone in males, hyperammonemia, decreased serum thymulin activity, decreased IL-2 production, decreased natural killer cell activity, alterations in T cell subpopulations (Prasad, A S (Prasad, A S, ed.) (1988) *New York:Alan R. Liss*, 3–53), impaired neuropsychological functions (Penland, J. G. (1976) *FASEB, J* 5:A938), and decreased ethanol clearance (Milne et al. (1991) *Am J Clin Nutr* 53:25).

The composition of the invention can be administered to the subject by a route of administration which allows the composition to perform its intended function. Various routes of administration are described herein in the section entitled "Pharmaceutical Compositions". Administration of a therapeutically active or therapeutically effective amount of the composition of the present invention is defined as an amount effective, at dosages and for periods of time, necessary to achieve the desired result.

Other aspects of the invention pertain to methods for evaluating a candidate compound for the ability to interact with, e.g., bind, an MRT polypeptide. These methods include contacting the candidate compound with the MRT polypeptide and evaluating the ability of the candidate compound to interact with, e.g., to bind or form a complex with the MRT polypeptide. These methods can be performed in vitro, e.g., in a cell free system, or in vivo, e.g., in a two-hybrid interaction trap assay. These methods can be used to identify naturally occurring molecules which interact with MRT polypeptides. They can also be used to find natural or synthetic inhibitors of MRT polypeptides.

Yet other aspects of the invention pertain to methods for identifying agents which modulate, e.g., inhibit or activate/stimulate, an MRT polypeptide or expression thereof. Also contemplated by the invention are the agents which modulate, e.g., inhibit or activate/stimulate MRT polypeptides or MRT polypeptide expression and which are identified according to methods of the present invention. In one embodiment, these methods include contacting a first polypeptide, e.g., a naturally occurring ligand of MRT, with a second polypeptide comprising an MRT polypeptide and an agent to be tested and determining binding of the second polypeptide to the first polypeptide. Inhibition of binding of the first polypeptide to the second polypeptide indicates that the agent is an inhibitor of an MRT polypeptide. Activation of binding of the first polypeptide to the second polypeptide indicates that the agent is an activator/stimulator of an MRT polypeptide.

V. Pharmaceutical Compositions

The transgenic plant in which the expression of MRT polypeptide is altered, or portions thereof, and other agents described herein can be incorporated into pharmaceutical compositions suitable for administration. Such compositions typically comprise the transgenic plant in which the expression of MRT polypeptide is altered, a portion thereof, or agent and a pharmaceutically acceptable carrier. As used herein the term "pharmaceutically acceptable carrier" is intended to include any and all solvents, dispersion media, coatings, antibacterial and antifingal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, polypeptides, compositions, transgenic plants or portions thereof, of the invention can be administered to a subject to treat metal-deficiency, e.g., iron- or zinc-deficiency, or can be administered to a subject, e.g., human or animal, as a nutritional supplement, e.g., as a metal source, e.g., as an iron or zinc supplement. The polypeptides, compositions, or plants are administered to the subjects in a biologically compatible form suitable for pharmaceutical administration in vivo. By "biologically compatible form suitable for administration in vivo" is meant a form of the polypeptide, composition, or plant, e.g., transgenic plant, to be administered in which any toxic effects are outweighed by the therapeutic effects of the polypeptide composition or plant. Administration of a therapeutically active or therapeutically effective amount of a polypeptide, composition, or plant of the present invention is defined as an amount effective, at dosages and for periods of time necessary to achieve the desired result. For example, a therapeutically active amount of a transgenic plant in which expression of MRT polypeptide is altered can vary according to factors such as the disease state, age, sex, and weight of the subject, and the ability of the composition to elicit a desired response in the subject. Dosage regimens may be adjusted to provide the optimum therapeutic response. For example, several divided doses can be administered daily or the dose can be proportionally reduced as indicated by the exigencies of the therapeutic situation.

The polypeptides, composition, or plant can be administered in a convenient manner such as by oral administration, e.g., as a nutritional supplement, injection (subcutaneous, intravenous, etc.), and other methods of parenteral administration. Depending on the route of administration, the polypeptide, composition, or plant can be coated in a material to protect it from the action of enzymes, acids and other natural conditions which may inactivate the agent.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the polypeptides, compositions, or plants are prepared with carriers that protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

To administer a polypeptide, composition, or plant by other than parenteral administration, it may be necessary to coat it with, or co-administer it with, a material to prevent its inactivation. For example, a transgenic plant in which expression of an MRT polypeptide is altered or a portion thereof can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al. (1984) *J. Neuroimmunol* 7:27). Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the polypeptide, composition, or plant in the required amount in an appropriate solvent with one or a combination of ingredients enumerated above, as required, followed by filtered sterilization. Generally, dispersions are prepared by incorporating the polypeptide, composition, or plant into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

This invention is further illustrated by the following examples which in no way should be construed as being further limiting. The contents of all cited references (including literature references, issued patents, published patent applications, and co- pending patent applications) cited throughout this application are hereby expressly incorporated by reference.

EXAMPLES

The Following Materials and Methods Were Used in Examples 1–4

Yeast Growth Conditions and Library Screening

Yeast cells were grown in 1% yeast extract, 2% peptone supplemented with 2% glucose (YPD). The pH of liquid YPD medium was lowered to pH 4.0 with HCl to aid growth of fet3fet4 double mutants. YPD medium was made iron-limiting by adding 80$\mu$M bathophenanthroline disulfonate (BPS; Sigma, St. Louis, Mo.). Cells were also grown in synthetic defined medium (SD, 6.7 g/liter of yeast nitrogen base without amino acids) supplemented with 20 g/liter of glucose and necessary auxotrophic supplements. This medium was also supplemented with 10 $\mu$M FeCl$_3$ and the pH was lowered to 3.5 to aid growth of the fet3 fet4 strain. DEY1453 (MATα/MATαade2/+can1/can1 his3/his3 leu2/leu2 trpl /trpl ura3/ura3 fet3-2::HIS3/fet3-2::HIS3 fet-4-1::LEU2/fet4-1::LEU2was transformed using standard procedures (Schiestl, R. H. et al. (1989) *Curr. Genet.* 16: 339–346) with a plasmid library containing *A. thaliana* cDNAs inserted under the control of the phosphoblycerate kinase promoter in pFL61 (Minet, M. et al. (1992) *Plant J.* 2: 417–422). The poly (A)$^+$RNA used to construct this library was isolated from whole young seedlings (stage two leaves) grown on an iron-sufficient medium. Ura$^+$ transformants were isolated, pooled into 100 groups of 30,000 transformants each (i.e., 3×10$^6$ total transformants), and 1×10$^6$ cells from each pool were inoculated onto 100 YPD plus 80 $\mu$M BPS plates. Cells plated from six pools of transformants gave rise to several large colonies on this medium and a single colony was selected from each pool for further analysis. Plasmids were selectively removed from transformants using 5-fluoroorotic acid (Boeke, J. D. et al. (1987) *Methods Enzymol.* 154: 164–175).

Yeast DNA Manipulations

*Escherichia coli* TOP10 F' cells (Stratagene, La Jolla, Calif.) were used for all recombinant DNA procedures. The plasmid pZH1 was constructed by inserting the 1.4 kb NotI insert fragment from one isolate, pIRT-1, into the NotI site of pBluescript SK (+) (Stratagene, La Jolla, Calif.). Sequence analysis of the insert in pZH1 was performed by LARK Sequencing Technologies (Houston, Tex.). Computer database comparisons were performed using BLAST software (Altschul, S. F. et al. (1990) *J. Mol. Biol.* 215: 403–410); hydropathy analysis was performed and potential transmembrane segments were identified using the TOP-PREDII program (Claros, M. G. et al. (1994) *Comput. Appl. Biol. Sci.* 10: 685–686).

Iron Uptake Assays

Iron uptake assays using $^{55}$FeCl$_3$ (Amersham, Arlington Heights, Ill.) were performed as described (Eide, D. et al. (1992) *J. Biol. Chem.* 267: 20774–20781) except that MGN (10 mM Mes/2% glucose/1 mM nitrilotriacetic acid, pH 6.1) was used for the assay buffer. Where noted, 1 mM sodium ascorbate was added to reduce Fe(III) to Fe(II). Stock solutions of the chloride salt of each metal (except for iron) were prepared in water at a concentration of 100 mM and diluted into MGN to a final concentration of 10 $\mu$M before addition of the cells. The $^{56}$FeCl$_3$ stock was 50 mM prepared in 0.1M HCl. The statistical significance of differences in values relative to controls was determined using STATVIEW software (Abacus Concepts, Berkeley, Calif.). Data was subjected to one-way analysis of variance (ANOVA) followed by a Scheffe's test.

Plant Growth Conditions

Seeds of *A. thaliana* (Columbia ecotype) WT,frd1, and frd3 (Yi, Y. (1995) Ph. D. thesis (Dartmouth College, Hanover, N.H.)) were surface-sterilized and sown on plates of Gamborg's B5 medium (Sigma, St. Louis, Mo.) with 2% sucrose, 0.5 g/liter Mes, and 0.7% agar (final pH 5.8). Plates were stored for 2 days in the dark at 4° C. and then incubated at 21° C. under constant illumination (65 $\mu$E m$^{-2.s-1}$) for 11 days. A 3-mm thick yellow acrylic filter (acrylic yellow-2208, Cadillac Plastic and Chemical, Pittsburgh, Pa.) was placed between the light source and the plates to prevent the photochemical degradation of Fe(III)-EDTA (Hangarter, R. P. et al. (1991) *Plant Physiol.* 96: 843–847). Seedlings were then transferred to either iron-sufficient or iron-deficient nutrient plates. The medium contained macro- and micro-nutrients (Marschner, H. et al. (1982) *Z. Pflanzenphysiol.* 105: 407–416) plus 0.7% agar and 0.5 g/liter of Mes (final pH 6.0). The iron-sufficient medium contained 50 $\mu$M Fe(III)-EDTA and the iron-deficient medium contained 300 $\mu$M FerroZine [3-(2-pyridyl)-5,6-diphenyl-1,2,4-triazine sulfonate, HACH Chemical (Ames, Iowa)]. Plates were incubated for 3 days in the growth chamber described above.

Arabidopsis Nucleic Acid Analysis

For Southern blot analysis, 15-$\mu$g samples of Arabidopsis genomic DNA (Dellaporta, S. L. et al. (1983) *Plant Mol. Biol. Rep.* 1: 19–21) were digested overnight with the appropriate restriction enzymes, separated by electrophoresis on a 0.8% agarose gel, transferred to a nitrocellulose membrane, and bound to the membrane by UV crosslinking (Stratalinker; Stratagene, La Jolla, Calif.). Standard procedures were used for prehybridization and hybridization (Ausubel, F. M. et al. (1995) *Current Protocols in Molecular Biology* (Wiley, N.Y.). Membranes were then washed twice at room temperature for 15 min in 5×SSPE, 0.1% SDS, followed by two 15 min washes in 0.1×SSPE, 0.1% SDS at 50° C. (high stringency) or at room temperature (low stringency). Membranes were stripped for reprobing with a boiling solution of 1×SSC, 0.1% SDS. Southern blot analysis of genomic DNA from Columbia and Landsberg ecotypes digested with SalI and probed with a labeled IRT1 fragment revealed a restriction fragment length polymorphism between these lines. To map IRT1, Southern blots of genomic DNA from 30 recombinant inbred lines (Lister, C. et al. (1993) *Plant J.* 4: 745–750.) were then analyzed for segregation of the polymorphism. The IRT1 segregation data were compared with the segregation patterns of other markers and the IRT1 map position was determined using MAPMAKER software (Lander, E. S. et al. (1987) *Genomics* 1: 174–181). RNA was extracted (Verwoerd, T. C. et al. (1989) *Nucleic Acids Res.* 17: 2362) from root and shoot fractions of plants that had been grown axenically on either iron-sufficient or iron-deficient plates. Samples (10 $\mu$g) of RNA were denatured and electrophoresed on a 0.8% agarose, 6.2% formaldehyde gel and then transferred to a nylon membrane (BioTrans; ICN). RNA was bound to the membrane by UV crosslinking (Stratalinker; Stratagene, La Jolla, Calif.). The membrane was prehybridized, hybridized, washed, and stripped as described by Pilgrim and McClung (Pilgrim, M. L. & McClung, R. (1993) *Plant Physiol.* 103: 553–564). DNA fragments used as hybridization probes were radio labeled by the random primer method (Feinberg, A. P. et al. (1984) *Anal. Biochem.* 137: 266–267). For Southern blot analysis, the 1.4-kb EcoRI/XbaI insert fragment of expressed sequence tag (EST) 37F12T7 were used as probes for IRT1 and IRT2, respectively. The same IRT1 DNA fragment was used as a probe for Northern blot analysis as well as the 2.5-kb EcoRI insert fragment of pARR16 encoding rRNA (Richards, E. et al. (1988) *Cell* 53: 127–136).

The Following Materials and Methods Were Used
in Examples 6–9

Yeast Strains and Culture Conditions

Strains used were DY1457 (MATα ade6 can1 his3 leu2 trp1 ura3) and ZHY1 (MATα ade6 can1 his3 leu2 trp1 ura3 zrt1::LEU2). Yeast were grown in standard culture media (SD, YPD) (Eide, D., Davis-Kaplan S., Jordan, I., Sipe, D., and Kaplan, J. (1992) *J. Biol. Chem.* 267, 20774–20781) supplemented with necessary auxotrophic requirements and either 2% glucose or 2% galactose. A zinc-limiting medium (LZM) was prepared in the same manner as LIM (Eide and Guarenete (1992)*J. Gen. Microbiol.* 138:347–354) except that $ZnSO_4$ in LIM was replaced with 10 μM $FeCl_3$ in LZM. Cell number in liquid cultures was determined by measuring the optical density of cell suspensions at 600 nm ($A_{600}$) and converting to cell number with a standard curve.

Plasmids and DNA Manipulations *E. coli* and yeast transformations were performed using standard methods (Sambrook and Maniatis (1989) *Molecular Cloning: A Laboratory Manual* (Cold Spring Harbor Lab. Press, Plainview, N.Y.), 2nd Ed.; Schiestl and Gietz (1989) *Curr. Genet.* 16:339–346). Plasmids constructed are diagrammed in FIG. 6. A fragment bearing the ZRT1 open reading frame was prepared by the polymerase chain reaction (PCR) using primers derived from the ZRT1 sequence with either BamHI (Primer 3) or SalI restriction sites (Primer 4) added to their 5' ends (FIG. 6, Primer 3: 5'-CGGATCC/ATGA-GCAACGTTACTACG-3' (SEQ ID NO:15) and Primer 4: 5'-TACGCGTCGAC/TTAAGCCC-ACTTACCGAT-3' (SEQ ID NO:16); the slash indicates the beginning of the ZRT1 sequences in each primer). The resulting fragment was inserted into Bluescript SK+ (Stratagene, La Jolla, Calif.) to generate pSK+ZRT1. A PstI fragment containing the LEU2 gene was prepared as described (Dix et al. (1994) *J. Biol. Chem.* 269:26092–26099) and inserted into pSK+ ZRT1 to generate pZH2. This plasmid contains the zrt1disruption mutation, zrt1::LEU2. Plasmid pZH2 was digested with BamHI and SalI and transformed into DY1457 to replace the chromosomal locus by single-step gene transplacement (Rothstein, R. (1991) *Methods Enzymol.* 194:281–301). The resulting strain, ZHY1, was confirmed to contain the zrt1::LEU2 mutation by Southern blot analysis. Because ZHY1 grows more slowly than the wild type strain on media containing metal chelators, a plasmid (pMC5) containing a genomic ZRT1 fragment was isolated from a genomic library (Carlson and Botstein (1982) *Cell* 28:145–154) by complementation (Rose and Broach (1991) *Methods Enzymol.* 194:195–230) of the growth defect displayed by ZHY1 on YPD+200 μM bathophenanthroline disulfonate (Sigma Chemical Co., St. Louis, Mo.). The 2.2 kb SacI-HindIII fragment from pMC5 containing the genomic ZRT1 gene was subdloned into pRS316 (Sikorski and Boeke (1991) *Methods Enzymol.* 194:302–318) to generate pMC5-HS. The BamHI-SalI fragment generated with Primers 3 and 4 was also cloned into pRS316-GAL1 (Liu et al. (1992) *Genetics* 132:665–673) to generate pOE1. A PCR fragment containing bases–706 to+3 of ZRT1 (the first base of the ATG initiation codon is designated as position+1) was generated with Primers 1 and 2 (FIG. 6, Primer 1: 5'-GGAATTC/GAAGG-CAAGAGTATTTCAGAC-3' 9SEQ ID NO:17), Primer 2: 5'-CGGGATC/CATAATTCCTTTTT-TGATATTTG-3' (SEQ ID NO:18); the slash indicates the beginning of the ZRT1 sequence in each primer). This PCR fragment was digested with EcoRI and BamHI and inserted into the yeast integrating vector Ylp353 (Myers et al. (1986) *Gene* 45:299–310) to generate pGI1. This plasmid contains a fusion between the ZRT1 upstream flanking sequences, 5' untranslated region, and initiation methionine residue, and the *E. coli* lacZ gene. Plasmid pGI1 was then digested with NcoI, and transformed into DY1457 and ZHY1 to integrate the plasmid at the URA3 locus (Dix et al. (1994) *J. Biol. Chem.* 269:26092–26099). The plasmid pHYC3 contains HIS4 promoter elements fused to lacZ (Hinnebusch et al. (1985) *Proc. Natl. Acad. Sci. USA* 82:498–502). Database comparisons were performed with the National Center for Biotechnology Information databases using BLAST (Altschul et al. (1990) *J. Mol. Biol.* 215:403–410), and topology analysis was performed using the TOP-PREDII program (Claros and von Heijne (1994) *Comput. Appl. Biosci.* 10:685–686).

Zinc uptake and β-galactosidase assays

Zinc uptake assays were performed as described previously for iron uptake (Eide et al. *J. Biol. Chem.* 267:20774–20781) except that $^{65}ZnCl_2$ (Amersham Corp., Arlington Heights, Ill.) and LZM-EDTA were substituted for $^{59}FeCl_3$ and LIM-EDTA. Cells were incubated at 30° C. with $^{65}Zn$ for five minutes, filtered, and washed with 10 ml ice-cold SSW. Cell-associated radioactivity was measured by liquid scintillation. Kinetic values were derived using KinetAsyst software (IntelliKinetics, Princeton, N.J.). Zinc accumulation was measured in cells grown in LZM medium supplemented with 10 mM $^{65}Zn$ plus nonradioactive zinc to the indicated final concentration. Aliquots (0.5 ml) were filtered, washed with 10 ml ice-cold SSW, and counted by liquid scintillation. b-galactosidase activity was assayed as described by Guarente (Guarante, L. (1983) *Methods Enzymol.* 101:181–191).

RNA Isolation and Northern Blot Analysis

Total RNA was isolated from yeast (Sherman et al. (1986) *Methods in Yeast Genetics* (Cold Spring HarboLab. Press, Plainview, N.Y.)), denatured, separated by agarose gel electrophoresis (6 μg /lane), and analyzed by Northern blotting (Sambrook and Maniatis (1989) *Molecular Cloning: A Laboratory Manual* (Cold Spring Harbor Lab. Press, Plainview, N.Y.), 2nd Ed). Equal loading of RNA in each lane was confirmed by staining the gel with acridine orange. Probes used were the ZRT1 BamHI-SalI insert of pSK+ ZRT1 and ACT1 labeled with $^{32}P$ (Amersham Corp., Arlington Heights, Ill.) by the random priming method (Feinberg and Vogelstein (1984) *Anal. Biochem.* 137:266–267). Densitometric scanning was performed using a Sierra Scientific CCD camera and Image 1.4 software (National Institutes of Health, Bethesda, Md.).

The Following Materials and Methods Were Used
in Examples 10–14

Strains and Culture Methods

Strains used were DY1457 (MATα ade6 can1 his3 leu2 trp1 ura3), ZHY1 (MATα ade6 can1 his3 leu2 trp1 ura3 zrt1::LEU2), ZHY2 (MATα ade6 can1 his3 leu2 trp1 ura3 zrt2::HIS3), and ZHY3 (MATα ade6 can1 his3 leu2 trp1 ura3 zrt1::LEU2 zrt2::HIS3). Yeast were grown in YP or SD media (Sherman et al. (1986) *Methods in Yeast Genetics*, Cold Spring Harbor Laboratory, Cold Spring Harbor, N.Y.) supplemented with necessary auxotrophic requirements and either 2% glucose or 2% galactose. Zinc-limiting YP and SD agar plates contained either bathophenanthroline disulfonate (BPS, 200 μM) or EDTA (1 mM), respectively. A liquid zinc-limiting medium (low zinc medium, LZM) was prepared in the same manner as low iron medium (LIM) (Eide and Guarente (1992)*J. Gen. Microbiol.* 138:347–354) except that the $ZnSO_4$ in LIM was replaced with 10 μM $FeCl_3$ in LZM. LZM is similar in composition to SD medium with two modifications essential to controlling zinc availability. First, 1 mM EDTA is added to provide buffering for the concentration of free metal ions. Second, the medium is pH-buffered at 4.2 with 20 mM citrate to prevent pH changes that could alter the metal binding ability of EDTA. LZM was also prepared without EDTA (LZM-EDTA) which is less zinc-limiting because the predominant chelator in this medium, citrate, binds zinc with less affinity than does EDTA. The concentrations of free (i.e. unchelated) zinc were calculated using MAXCHELATOR software (Chris Patton, Stanford University). Cell number in liquid cultures was determined by measuring the absorbance of cell suspensions at 600 nm ($OD_{600}$) and converting to cell number with a standard curve.

Zinc Uptake and β-galactosidase Assays

Zinc uptake assays were performed as described previously for iron uptake (Eide et al. (1992) *J. Biol. Chem.* 267:20774–20781) except that $^{65}ZnCl_2$ (Amersham) and LZM-EDTA were substituted for $^{59}FeCl_3$ and LIM-EDTA, respectively. Cells were incubated for 5 minutes in LZM-EDTA plus the indicated concentration of $^{65}Zn$, collected on glass fiber filters (Schleicher and Schuell), washed with 10 ml ice-cold SSW (1 mM EDTA, 20 mM trisodium citrate, 1 mM $KH_2PO_4$, 1 mM $CaCl_2$, 5 mM $MgSO_4$, 1 mM NaCl pH 4.2), and cell-associated radioactivity was measured by liquid scintillation counting. Cells were starved for glucose by incubating them in LZM-EDTA prepared without glucose for one hour at 30° C. prior to assay. Michaelis-Menten kinetic values were determined using KINETASYST software (Intellikinetics, Princeton, N.J.). Stock solutions of the chloride salts of Co, Cu, Mg, Mn, and Ni were prepared in distilled water at a concentration of 100 mM. The nonradioactive $ZnCl_2$ stock was prepared at 100 mM in 0.02N HCl and the $FeCl_3$ stock was prepared at 50 mM in 0.1N HCl. The statistical significance of the differences of values relative to controls was determined with one-way analysis of variance (ANOVA) followed by a Dunnett multiple comparison test. β-galactosidase activity was assayed in cells harvested at an $OD_{600}$ of 0.5–2.0 as described by Guarente (Guarente, L. (1983) *Mehods Enzymol.* 101:181–191) and activity is expressed as the change in absorbance at 420 nm×1000 divided by (min×ml of culture used×$OD_{600}$ of the culture). Cell-associated zinc was measured in parallel cultures supplemented with tracer amounts of $^{65}Zn$ (10 μM) and nonradioactive zinc to the indicated final concentration. Aliquots (0.5 ml) were filtered, washed with 10 ml ice-cold SSW, and radioactivity measured by liquid scintillation.

Isolation of the ZRT2 Gene and DNA Manipulations

*E. coli* and yeast transformations were performed using standard methods (Sambrook et al. (1989) *Molecular Cloning: A Laboratory Manual*, 2nd Ed., (Cold Spring Harbor Laboratory, Cold Spring Harbor, N.Y.); Schiestl, and Gietz (1989) *Curr. Genet.* 16:339–346). To screen for multicopy suppressors of the zrt1mutation, ZHY1 cells were transformed with a genomic library constructed in the multicopy vector YEp24 (Carlson and Botstein (1982) *Cell* 28:145–154). Approximately 40,000 Ura+transformants were isolated and replated onto zinc-limiting YP glucose+BPS agar plates. Three independent transformants were isolated that formed larger colonies on this medium than the untransformed parent strain. Plasmid-dependence was verified by selectively removing the plasmids from each transformant with 5-fluoroorotic acid (Boeke et al. (1987) *Methods Enzymol.* 154:164–175) followed by replating onto YP glucose +BPS. DNA was prepared from each transformant, and the plasmids were then transformed into *E. coli* TOP10F' (Invitrogen). Plasmid DNA was prepared, restriction mapped, and the ends of the inserts were sequenced as described by Borson et al. (Borson et al. (1992) *PCR Methods Appl.* 2:144–148). This analysis demonstrated that two of the plasmids (pMC1 and pMC5) have cDNA inserts containing ZRT1. The third plasmid, pMC4, contains the ZRT2 gene. Computer database comparisons were performed using BLAST (Altschul et al. (1990) *J. Mol. Biol.* 215:403–410), potential transmembrane domains were identified using TOP-PREDII (Claros and von Heijne (1994) *Comput. Appl. Biosci.* 10:685–686), and multiple sequence alignment was performed using PILEUP (Genetics Computer Group) (Devereux et al. (1984) *Nucleic Acids Res.* 12:387–395).

A fragment bearing the ZRT2 open reading frame was prepared from pMC4 by the polymerase chain reaction (PCR) using primers derived from the ZRT2 sequence with either SalI (Primer 1: 5'-ACGCGTCGACATGGTTGATCTTATAGCGAG-3' (SEQ ID NO:19)) or SacI restriction sites (Primer 2: 5'-CCCGAGCTCCTATGCCCATTT CCCTAG-3' (SEQ ID NO:20)) added to their 5' ends. The resulting fragment was inserted into Bluescript SK+(Stratagene, La Jolla, Calif.) to generate pSK+ZRT2. A BamHI fragment containing the HIS3 gene was prepared from YCp407 (Stearns et al. (1990) *Methods Enzymol.* 185:280–297) and inserted into pSK+ZRT2 to generate pZH3. This plasmid contains the zrt2 disruption mutation, zrt2::HIS3. Plasmid pZH3 was digested with SalI and SacI to liberate the zrt2::HIS3 fragment and transformed into DY1457 and ZHY1 to replace the chromosomal locus by single-step gene transplacement (Rothstein, R. (1991) *Methods Enzymol.* 194:281–301). The resulting strains, ZHY2 and ZHY3, were confirmed to contain the zrt2::HIS3 allele by Southern blot analysis. The SalI-SacI PCR fragment generated with Primers 1 and 2 was also cloned into pRS316-GAL 1 (Liu et al. (1992) *Genetics* 132:665–673) to generate pOE2. The plasmid pGI1 (Zhao and Eide (1996) *Proc. Natl. Acad. Sci. U.S.A.* 93:2454–2458), containing a fusion between the ZRT1 promoter and the *E. coli* lacZ gene, was digested with NcoI and transformed into DY1457, ZHY1, ZHY2 and ZHY3 to integrate the plasmid at the URA3 locus (Rothstein, R. (1991) *Methods Enzymol.* 194:281–301).

Example 1
Isolation and Sequence Analysis of the IRT1 Gene

An *A. thaliana* cDNA library was screened for clones that, when expressed in *S. cerevisiae*, could restore iron-limited growth to a yeast strain defective for iron uptake. A fet3fet4 double mutant is sensitive to iron limitation due to its reliance on additional and apparently less efficient uptake mechanisms. This mutant strain was transformed with an Arabidopsis cDNA library constructed in a yeast expression vector, and approximately $3 \times 10^6$ independent transformants were screened on a rich medium made iron-limiting by adding the Fe(II) chelator, BPS. Six independent transformants that formed larger colonies on this medium were isolated. The plasmids carried by these transformants were required for the improved growth; this ability was lost when the plasmid was removed from each strain. Restriction endonuclease mapping indicated that all six plasmids contain inserts derived from the same gene. The gene has been designated IRT1 for iron-regulated transporter. IRT1 mapped to chromosome 4 by restriction fragment length polymorphism analysis (Lister, C. et al. (1993) *Plant J.* 4: 745–750).

The entire cDNA insert of one of the six plasmids, pIRT-1, was sequenced and found to be 1348 bp in length and to contain a single 1017 bp open reading frame capable of encoding a polypeptide of 339 amino acids (FIG. 1A). The predicted amino acid sequence of IRT1 shows that it is an integral membrane protein. Greater than 60% of the amino acids are nonpolar and these are arrayed in eight regions longer than 20 amino acids. These eight regions form transmembrane domains. The hydrophobic nature of the IRT1 amino acid sequence and the arrangement of potential transmembrane domains, coupled with the biochemical analysis described herein, demonstrates that IRT1 is an Fe(II) transport protein. Therefore, the IRT1 amino acid sequence was examined for potential metal-binding domains. IRT1 has four histidine-glycine repeats located at amino acids 154–161 in the region between transmembrane domains 3 and 4. This histidine-rich domain is important in substrate binding or regulation of this transporter. Several metal-binding proteins use the imidazole ring nitrogen of histidine as a coordinating ligand for metal ions (Karlin, D. D., (1993) *Science*, 261: 701–708.29; O'Halloran, T. V. (1993) *Science*, 261:715–725.). Moreover, similar domains [i.e., (-His-X-)$_{3-6}$] are found in analogous positions in the amino acid sequences of four other proteins thought to play a role in metal transport (Kamizono, A.et al. (1989) *Mol. Gen. Genet.* 219: 161–167.31; Conklin, D. S.et al. (1992) *Mol. Cell. Biol.* 12: 3678–368832; Palmiter, R. D. et al. (1995) *EMBO J.* 14: 639–649).

Example 2
IRT1 is a Member of a Gene Family

The predicted amino acid sequence of IRT1 has no detectable similarity to FET3 (Dix, D. R et al. (1994) *J. Biol. Chem.* 269: 26092–26099), FET4 (Askwith, C. et al. (1994) *Cell* 76: 403–410), or COPT1, a putative copper transporter from *A. thaliana* (Kampfenkel, K.et al. (1995) *J. Biol. Chem.* 270: 28479–28486). Also, although they share the same number of potential transmembrane domains, there is no detectable similarity between IRT1 and the *E. coli* Fe(II) transporter protein encoded by the feoB gene (Kammnler, M. et al. (1993) *J. Bacteriol.* 175: 6212–6219). The lack of similarity among these proteins suggests that each may transport the substrate by a different biochemical mechanism. However, comparison of the IRT1 amino acid sequence with GenBank™, EMBL, and SWISS-PROT databases identified two closely related sequences in Arabidopsis. Amino acids 8 through 127 of IRT1 are 72% (86 of 119) identical and 86% similar (i.e., identities plus conservative substitutions) to the predicted amino acid sequence of a cDNA partially sequenced as an EST (FIG. 1B). Because of this high degree of similarity to IRT1, this gene has been designated IRT2. Furthermore, the carboxylterminal 47 amino acids of IRT1 are 45% (21 of 47) identical and 68% similar to the sequence of a partially sequenced open reading frame located downstream of the ferrodoxin-encoding FEDA gene (Somers, D. E. et al. (1990) Plant Physiol. 93: 572–577). This gene is referred to as IRT3. The GenBank™ data base accession numbers for IRT2, IRT3, and the rice EST are T04324, M35868, and D49213, respectively. The numbers refer to the IRT1 amino acid sequence, bars indicate positions of amino acid identity, and positions of conservative substitutions are indicted by the colons. Conservative substitutions are based on the following groupings of amino acids: (L, I, V, M) (A, G, P, S, T) (R, K, H), (Q, D, E, N), and (F, Y, W)(Dayhoff, M. O. et al. (1978) in *Atlas of Protein Sequence and Structure* (Natl. Biomed. Res. Found., Silver Spring, Md.), pp. 345–352).

A low stringency Southern blot using IRT1 as the probe confirmed that IRT1 is a member of a small gene family. A comparison of the hybridization patterns seen on Southern blots using IRT1 and IRT2 as probes indicates that some of the bands seen on the low stringency Southern blot probed with IRT1 can be attributed to IRT2. When *A. thaliana* DNA was digested with EcoRI, IRT1 and IRT2 hybridized strongly to 4.2- and 9.6-kb fragments, respectively. The same fragments showed weak (but visible) hybridization with the opposite probes, i.e., IRT1 weakly hybridized to the 9.6-kb fragment and IRT2 weakly hybridized to the 4.2-kb band. Digestion with the enzymes HincII and AvaI generated a 1.2-kb fragment that hybridized strongly to IRT1 and a 1.8-kb fragment that strongly hybridized to IRT2. Again, both fragments showed weak hybridization to the opposite probes. With both digestions, other weakly hybridizing fragments were visible that could not be attributed to either IRT1 or IRT2. These fragments represent additional members of the IRT1 gene family, such as IRT3, present in the *A. thaliana* genome. Furthermore, DNA sequences similar to IRT1 were detected by low stringency hybridization of the IRT1 cDNA to DNA isolated from several other dicots including tomato, broccoli, and mustard.

Database comparisons also identified IRT1 related genes in the genomes of rice (a strategy II plant) (FIG. 1B), yeast, nematodes, and humans. The rice gene was identified as an EST and has 64% identity and 82% similarity to IRT1 over an 84-aa region. Two related *S. cerevisiae* genes (GenBank™ accession nos. P32804 and X91258) were identified. Both of these genes encode proteins that are similar in length to IRT1 (376 and 422 amino acids) and are ≈30% identical and 60% similar to IRT1. These genes were identified as open reading frames in the course of genomic sequencing and their functions are currently being investigated. The nematode sequence (GenBank™ accession no. U28944) was also identified by genomic sequencing and has 23% identity and 47% similarity to IRT1 over an 84 amino acid stretch. Finally, a human EST (GenBank™ accession no. H20615) was identified with 31% identity and 43% similarity to IRT1 over 82 amino acids. Given their close similarity to IRT1, these related genes encode metal transporters in the organisms in which they are found.

Example 3
IRT1 Expression Confers Iron Uptake Activity

Figure 2A:
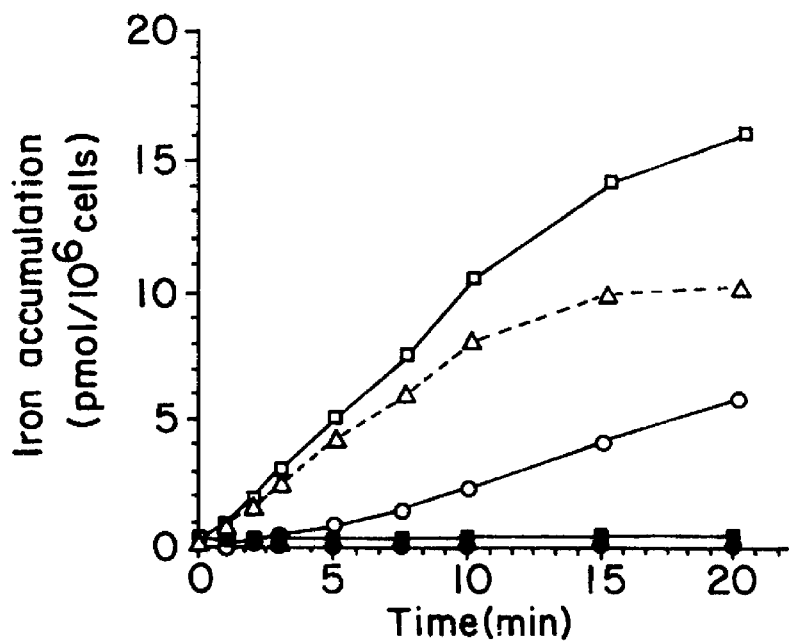
FIGS. 2A and 2B are graphs depicting the effect of IRT1 expression on iron uptake in yeast.
Figure 2B:
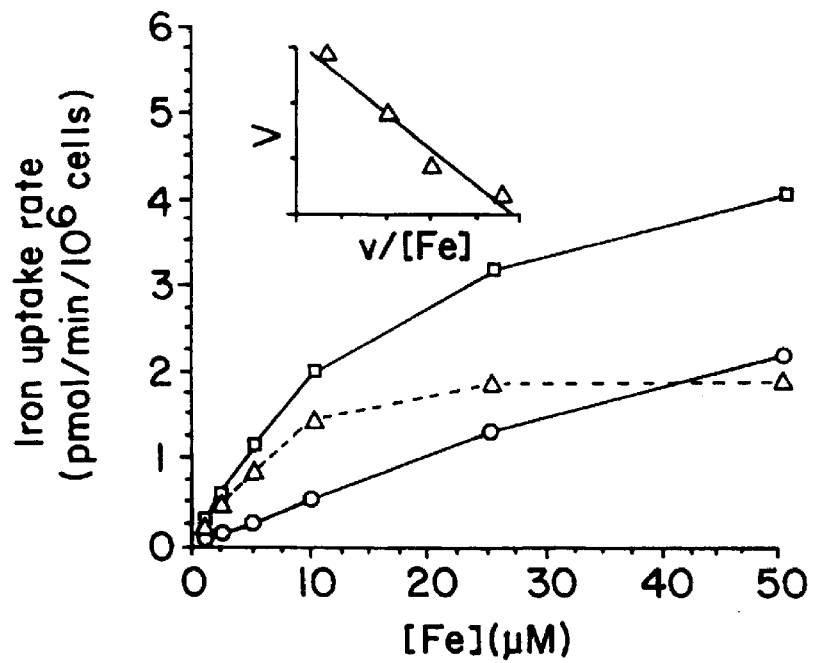

To determine if IRT1 encodes an iron transporter, $^{55}$Fe uptake rates were examined in a fet3fet4 strain expressing IRT1. Little or no uptake was detected at 0° C. for either IRT1-expressing or untransformed control cells (FIG. 2A). The fet3 fet4 mutant strain DEY1453 (circles) and DEY1453 transformed with pIRT-1 (squares) were grown to exponential phase in SD glucose and assayed for iron uptake with $^{55}$Fe. (A) Time- and temperature- dependence of iron accumulation assayed in MGN with 1 mM ascorbate and 5 $\mu$M $^{55}$FeCl$_3$ assayed at 30° C. (open symbols) or OC (solid symbols). The dashed line marked with open triangles represents the IRT1 -dependent accumulation, i.e., the accumulation of iron by the untransformed strain at 30° C. subtracted from the accumulation of the pIRT-1-bearing strain at 30° C. At 30° C., IRT1 expression resulted in an increased uptake rate for the first 10 min of the assay, after which the rate dropped to the control level. The IRT1-dependent rate was ≈3-fold higher than the control uptake rate. No increased uptake was apparent in strains bearing either of two randomly selected clones from the library, indicating the dependence of these uptake effects on expression of IRT1. The iron uptake activity dependent on IRT1 expression was also concentration-dependent and saturable (FIG. 2B). The same strains as in A were assayed for iron uptake rates for 10 min over a range of concentrations. The dashed lines marked with open triangles represents the IRT1- dependent uptake rate, i.e., background uptake rate of the untransformed strain subtracted from the corresponding rate of the pIRT-1-bearing strains. (Inset) Eadie-Hofstee plot of the IRT1-dependent uptake data. Each point represents the mean of three experiments each performed in duplicate. The standard deviation within each experiment was less that 20% of the corresponding mean. The concentration dependence of IRT1-mediated uptake was found to generate a linear Eadie-Hofstee plot (FIG. 2B, Inset) with an apparent $K_m$ of 6±1 $\mu$M and a $V_{max}$ of 1.9±0.4 pmol per min per $10^6$ cells. Taken together, these results show that IRT1 expression in yeast produces a time-, temperature-, and concentration-dependent system of iron uptake.

Figure 3A:
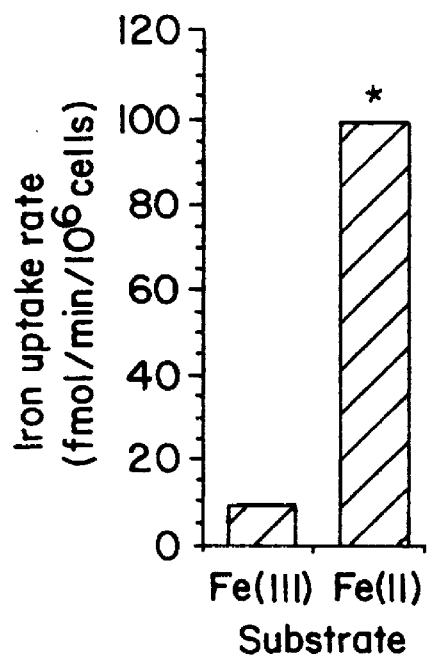
FIG. 3A is a bar graph depicting the inhibition of IRT1-dependent uptake in yeast by other metals.
Figure 3B:
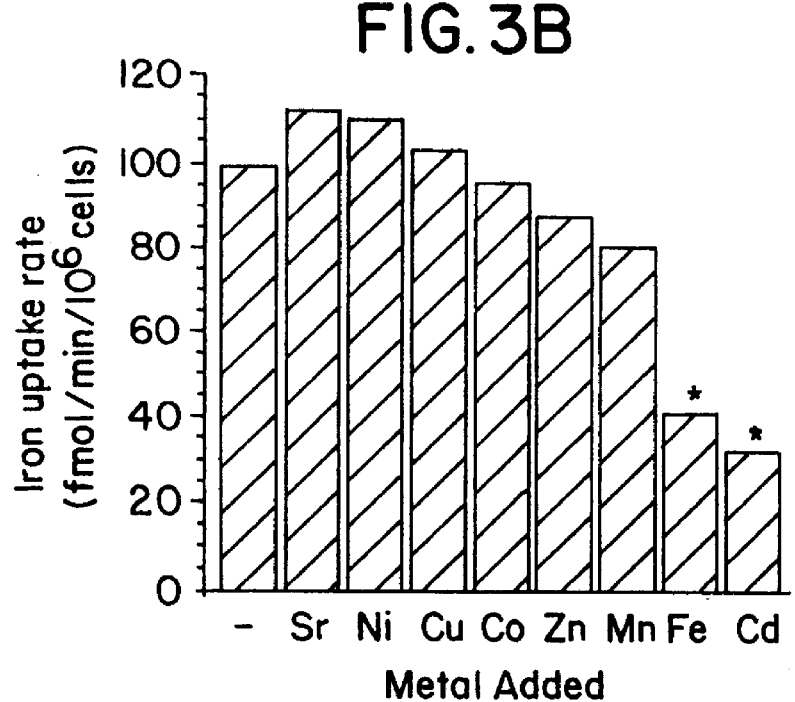
FIG. 3B is a bar graph depicting the inhibition of IRT1-dependent uptake by other transition metals.

The experiments described above were conducted with iron supplied as Fe(II), i.e., in the presence of ascorbate, an agent capable of reducing Fe(III) to Fe(II). To determine if Fe(II) is the preferred substrate over Fe(III), assays were carried out in the absence of ascorbate where iron is supplied to the cells as Fe(III). It has been found that the iron uptake rate in the absence of ascorbate was ≈10% of the rate when ascorbate was present (FIG. 3A). The fet3 fet4 mutant strain DEY1453 and DEY1453 transformed with pIRT-1 were grown to exponential phase is SD glucose and assayed for iron uptake with 1 $\mu$M $FeCl_3$ in MGN for 10 min. The values shown are the IRT1-dependent rates, i.e., the untransformed strain control values were subtracted from the DEY1453 pIRT-1 values and represent the means of four replicates. The asterisks indicate significant of differences from the control values (P<0.05). Assays were performed in the absence [Fe(III)] or presence [Fe(II)] of 1 mM ascorbate. This result shows that Fe(II) is preferred over Fe(III) as substrate for the IRT1 transporter. Although yeast are capable of reducing Fe(III) to Fe(II) through the action of plasma membrane Fe(III) reductases, this rate of cell-mediated reduction is slower than reduction by ascorbate and therefore may be rate-limiting for IRT1-dependent uptake. To assess if metals other than iron are potential substrates for IRT1, several transition metals were tested for their ability to inhibit accumulation of iron in IRT1-expressing cells (FIG. 3B). Assays were conducted in the absence (−) or presence of 10 $\mu$M metal. Radioactive iron was supplied as Fe (II) in the presence of 1 mM ascorbate. Iron was supplied as Fe(II) in these assays (i.e., in the presence of ascorbate) and the concentration of the metals tested was 10 times higher than the concentration of radiolabeled iron. The addition of Sr, Ni, Cu, Co, Zn, and Mn had no significant effect on the rate of iron uptake by IRT1. Cd and nonradiolabeled Fe(II) proved to be potent inhibitors of iron uptake. At 100-fold excess, Co, Mn, and Zn were also found to inhibit IRT1-dependent iron uptake. The observed decreases in iron uptake rate were not due to toxicity of any of these metals because control experiments detected no loss of cell viability resulting from metal exposure. Therefore, although the mechanism of this inhibition is not yet known, these data show that IRT1 is relatively specific for Fe(II) but is also capable of transporting Cd, Co, Mn, and/or Zn.

Example 4
Regulation of IRT1 in Wild-Type and Mutant Plant Lines in Responce to Iron IRT1 mRNA is expressed at a high level in roots of iron-deficient plants; no signal was detected on a Northern blot with total RNA prepared from roots of iron-sufficient plants or from shoots of iron-sufficient or iron-deficient plants. The signal detected on the Northern blot is specific for IRT1; using gene-specific probes for IRT1 and IRT2, no hybridization was detected with the IRT2 probe. Thus IRT1 has a pattern of expression similar to Fe(III) chelate reductase activity, showing increased expression under iron deficiency. The pattern of IRT1 expression was also examined in two different Fe(III) chelate reductase mutants, frd1 and frd3.

Plants carrying the frd1 mutation do not show an increase in Fe(III) chelate reductase activity in response to iron deficiency whereas frd3 mutants express reductase activity under both iron-sufficient and iron-deficient growth conditions (Yi, Y. (1995) Ph. D. thesis (Dartmouth College, Hanover, N.H.)). The frd1 mutant showed some expression of IRT1 in roots from plants grown on iron-sufficient plates, indicating that these plants may actually be iron-deficient. This is consistent with the chlorosis observed in this line. frd3 plants showed equally high levels of IRT1 mRNA in the roots of iron-sufficient and iron-deficient plants. This pattern of regulation is similar to that of the Fe(III) chelate reductase in this mutant and indicates that reductase activity and IRT1 expression are controlled by iron availability through a shared regulatory system.

The ability of IRT1 to suppress the mutant phenotype of a yeast strain defective for plasma membrane Fe(II) transport, together with the increased Fe(II) uptake observed in yeast expressing IRT1, demonstrates a role for this gene in uptake of iron across the plasma membrane of plant cells. Also, given the observations that IRT1 mRNA is expressed in roots, is induced by iron deprivation, an is corrugated with the plasma membrane Fe(III)-chelate reductase in wild-type and frd3 plants, the physiological role of IRT1 involves the uptake of iron from the rhizosphere across the plasma membrane in the root epidermal cell layer.

The studies described herein demonstrate that some other transition metals (Cd, Co, Mn, and Zn) are inhibitors of IRT1-mediated Fe(II) uptake in yeast and, therefore, can be substrates for this transporter.

Example 5
Construction of Transgenic Plants

A 1.4 kb Notl fragment from pIRT-1 (representing the IRT1 cDNA) was subcloned into the pCGN18 vector in both the sense and antisense directions. The CaMV 35S promoter was used to drive expression of IRT1. After confirming the constructs in *E. coli*, the plasmids were transformed into *Agrobacterium tumefaciens* strain ASE via eletroporation. The resulting Agrobacterium strains were then used to transform *Arabidopsis thaliana* ecotype Columbia using the vacuum infiltration method (Bechtold et i al. (1995) *Gene Transfer to Plants*, Potrykus and Spangenberg, eds., pp.19–23 (Springer-Verlag:Berlin, Germany). Alternatively, the gene constructs could be introduced into various plant species via bombardment using a particle gun (biolistics) or by co-cultivating *Agrobacterium tumefaciens* or *Agrobacterium rhizogenes* and plant cells or tissues and then regenerating transgenic plants from the transformed cells or tissues via tissue culture techniques. Seeds collected from vacuum-infiltrated plants were sown onto plates containing kanamycin. Kanamycin resistant plants were then transferred to soil and allowed to set seed. The progeny were collected from individual plants and tested for segregation of the transgenes. Families that showed 3:1 segregation of kanamycin resistance to kanamycin sensitivity were selected.

Example 6
Identification of ZRT1

Comparisons of the predicted Irt1p amino acid sequence against the current sequence databases indicated that IRT1 belongs to a family of closely related genes of unknown function, including two additional genes in *A. thaliana* and genes in rice, *C. elegans*, and humans. This comparison also identified two closely related open reading frames of unknown function from *S. cerevisiae*. One of these two yeast genes was designated ZRT1 for zinc-regulated transporter.

The sequence of the open reading frame corresponding to ZRT1(GenBank™ accession number P32804) was originally obtained during sequence analysis of a portion of the yeast genome (Breitwieser et al. (1993) *Yeast* 9:551–556). In this analysis, it was determined that ZRT1 is located on chromosome VII immediately adjacent to the FZF1 gene (FIG. 6) and is predicted to encode a protein of 376 amino acids. It has been found that Zrt1p is 30% identical and 50% similar (i.e. identities plus conservative substitutions) to Irt1p. A model of Zrt1p membrane topology suggested the presence of eight transmembrane domains located in nearly identical positions on the amino acid sequence as those predicted for Irt1p. Irt1p contains an amino acid sequence, $(-H-G-)_4$, that is a metal-binding domain. A similar sequence was also found in Zrt1p in which 3 of the 4 histidines are conserved but the fourth potential ligand is unclear. A histidine located approximately 30 amino acids toward the carboxyl terminus may contribute to metal binding. In both Irt1p and Zrt1p, this histidine-rich domain is found in a large loop between transmembrane domains 3 and 4. Topological predictions based on the "positive-inside" rule (Claros and von Heijne (1994) *Comput. Appl. Biosci.* 10:685–686) suggested that in both proteins this loop is located on the cytoplasmic surface of the membrane.

Example 7
ZRT1 is Required for Zinc-Limited Growth

Figure 6:
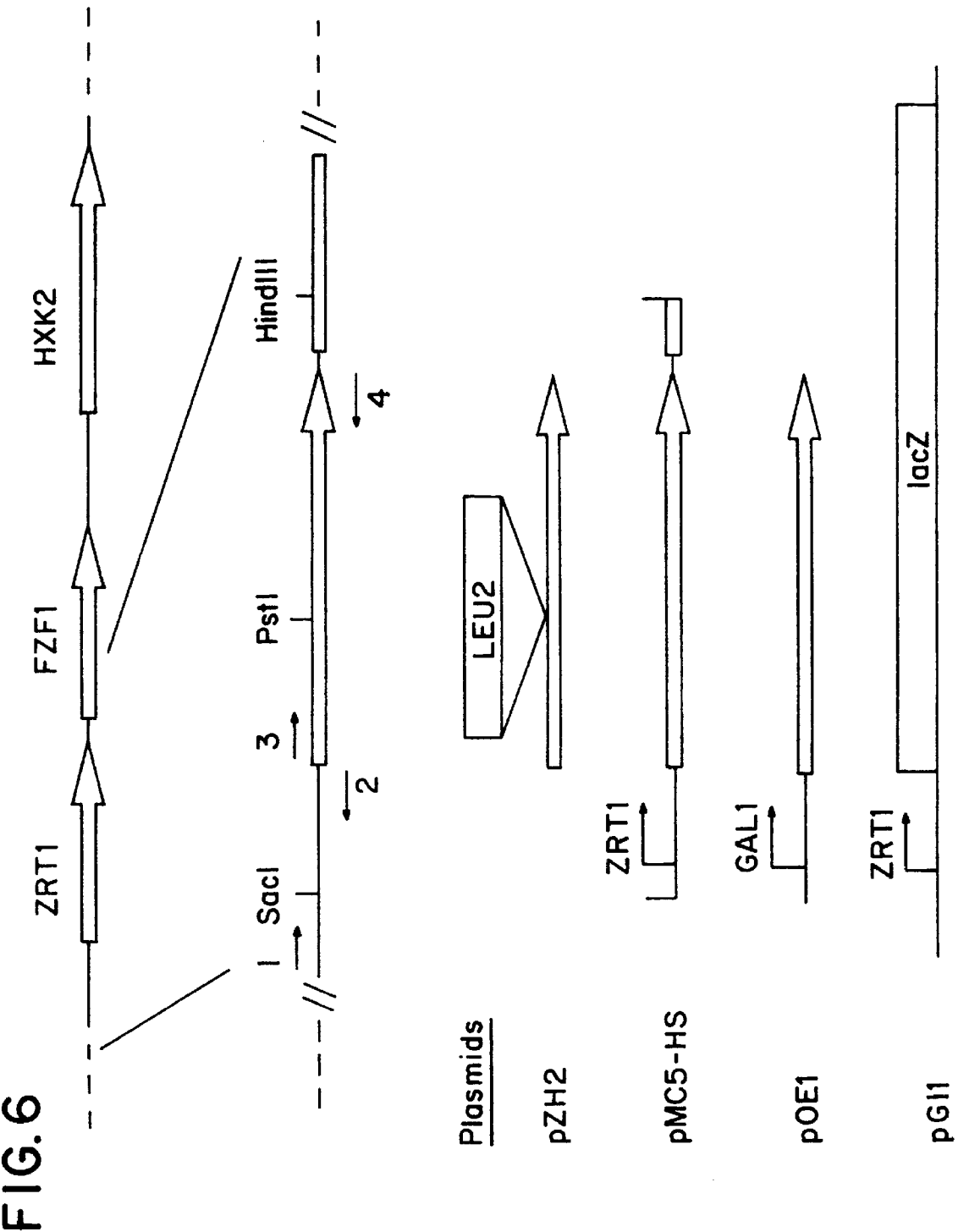
FIG. 6 depicts chromosomal region of the ZRT1 gene and plasmids constructed herein. The open reading frames on Chromosome VII are indicated by large arrows. The location of the relevant restriction sites in this region are indicated, and small arrows numbered 1–4 represent the primers used in plasmid construction. The promoters in the plasmids are identified by arrows labeled either ZRT1 or GAL1.
Figure 7:
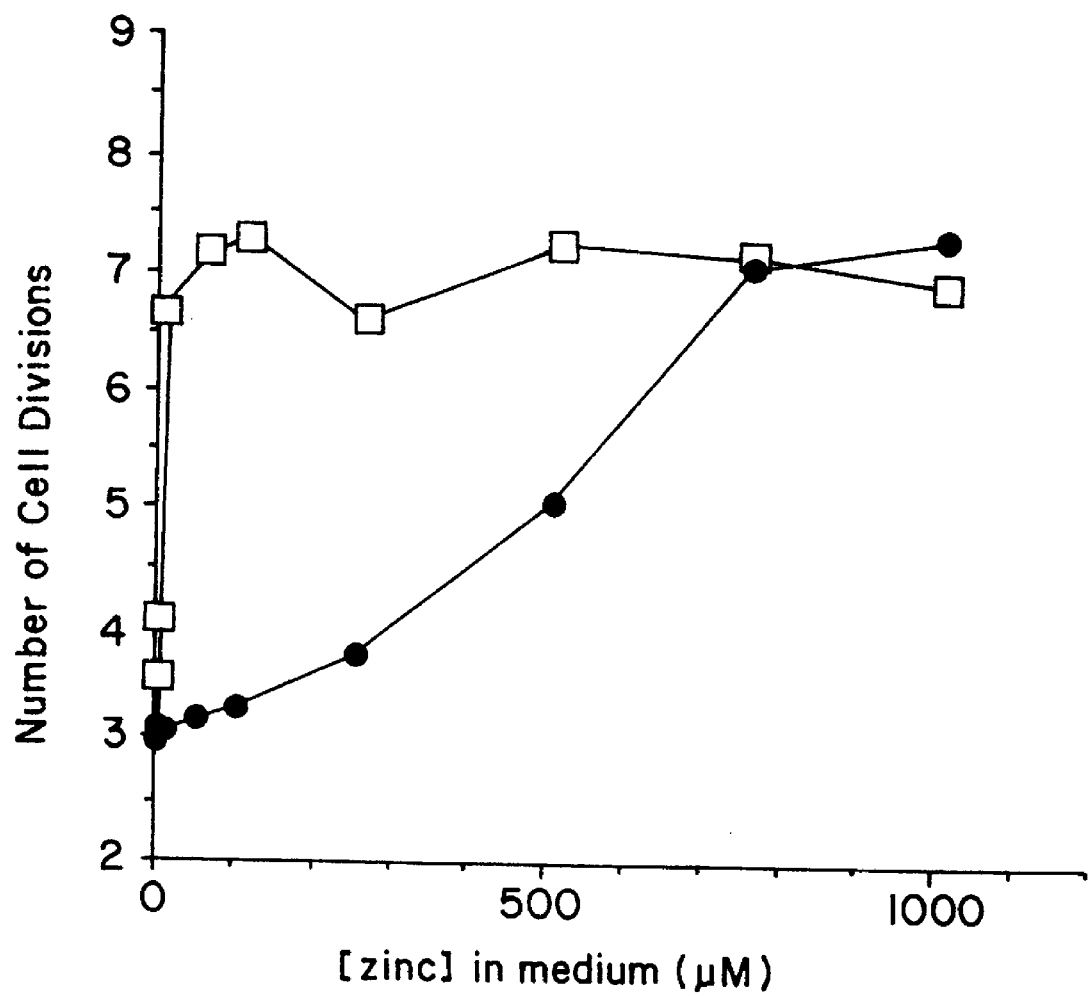
FIG. 7 is a graph depicting data which demonstrates that ZRT1 is required for zinc-limited growth. Shown are the mean values of three experiments.

To examine the function of ZRT1, a disruption mutation, zrt1::LEU2, was constructed by inserting the LEU2 gene into the center of ZRT1 (FIG. 6). This zrt1disruption allele was then introduced into a haploid yeast strain. The resulting mutant was viable, indicating that ZRT1 is not an essential gene. Northern blot analysis failed to detect ZRT1-related mRNA in this mutant strain indicating that the disruption allele was unlikely to retain any residual function. Despite its resemblance to the Irt1p iron transporter, Zrt1p does not play a role in iron uptake in yeast. No defect was observed in iron uptake in the zrt1 mutant. However, this mutant strain did not grow in an iron-limiting medium (LIM). Because of the high EDTA concentration in LIM (1 mM), this medium is expected to have low available levels of other metals that are bound tightly by this chelator. Supplements of other metals were tested for improved growth of the zrt1mutant in LIM. Adding 500 μM Co, Cu, Fe, Mg, or Mn to LIM had no effect on zrt1growth, but adding 500 μM zinc greatly enhanced growth of this mutant strain. To study this effect further, a low zinc medium, LZM, was developed in which cell growth could be limited by zinc deficiency and the growth response of the wild type and zrt1mutant strains to increasing levels of supplemented zinc was examined. Wild type (DY1457, squares) and zrt1mutant (ZHY1, circles) cells were inoculated into LZM supplemented with the indicated amount of ZnSO$_4$ and grown for 16 hours prior to cell number determination. While growth of the wild type strain in LZM without zinc supplement was severely inhibited, adding as little as 10 μM zinc allowed this strain to go through its maximum number of seven cell divisions over a 16 hour period (FIG. 7). Mutant zrt1cells attained this same maximum number of cell divisions only with zinc supplements of 750 μM or more, i.e. a 75-fold increase in the zinc requirement of the zrt1mutant compared to the wild type. This growth defect could be complemented fully by the plasmid pMC5-HS (FIG. 6), a genomic clone of the ZRT1 gene, indicating that the phenotype resulted from loss of ZRT1 function and not because the mutation affected the nearby FZF1 gene on chromosome VII.

Example 8
ZRT1 is Required for High Affinity Zinc Uptake

Figure 8A:
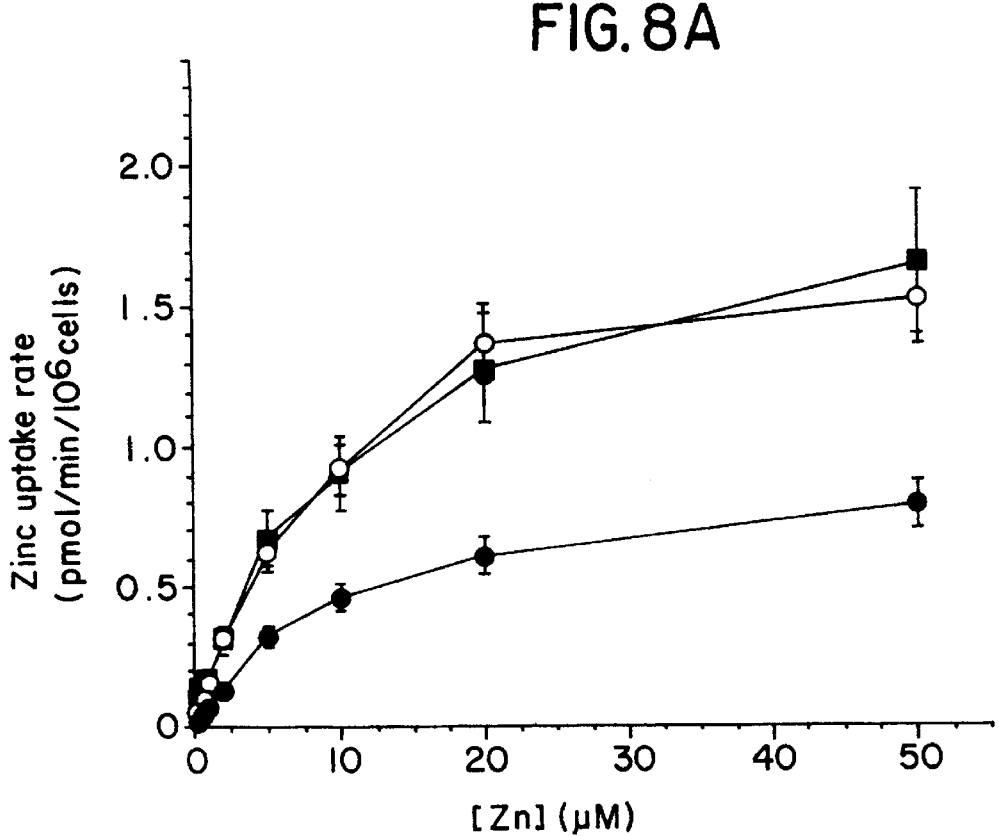
FIG. 8 contains two graphs depicting data which demonstrates that ZRT1 is required for high affinity zinc uptake. Shown are the mean values of two experiments each performed in duplicate; error bars indicate±one standard deviation.
Figure 8B:
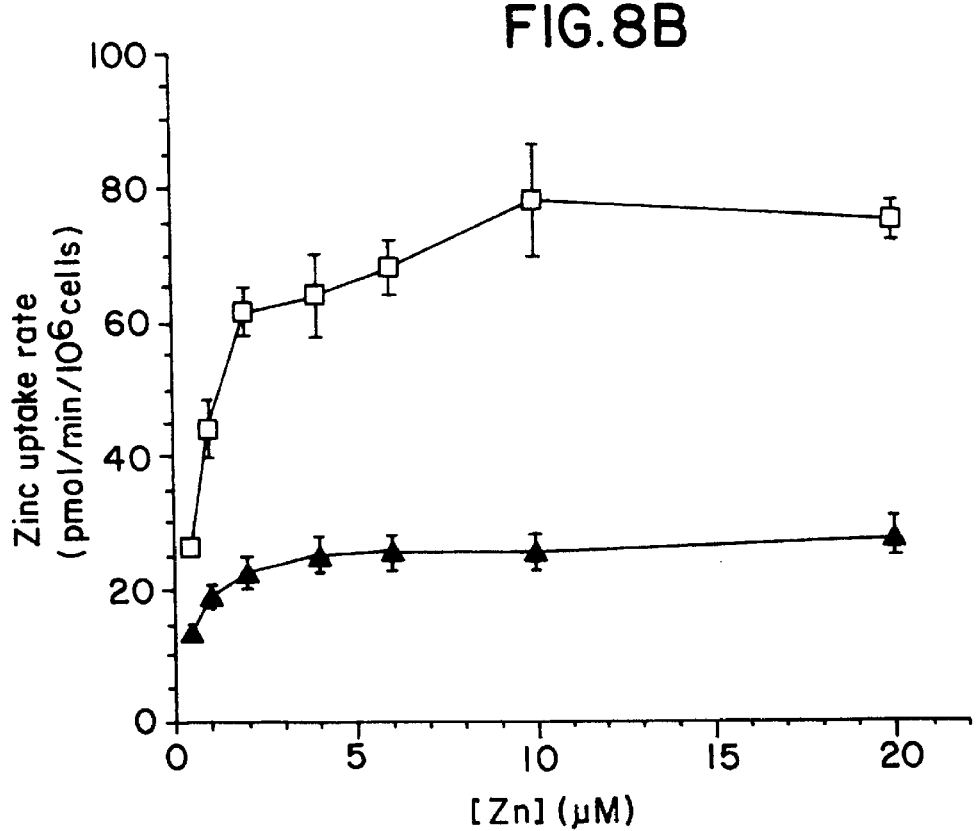

To determine if ZRT1 plays a role in zinc uptake, the biochemical properties of this process in wild type cells were first characterized. These conditions were selected on the basis of the experiment described in FIG. 10. Wild type (FIG. 10, DY1457, squares) and zrt1mutant (FIG. 10, ZHY1, circles) cells were grown to exponential phase in zinc-limited (open symbols, FIG. 10) and zinc-replete (FIG. 10, closed symbols) media and assayed for zinc uptake rate over a range ZnSO$_4$ concentrations. Zinc-limited media was LZM+10 μAM zinc for the wild type and LZM+500 μM zinc for the mutant. Zinc-replete conditions were LZM+1000 μM for both strains. ZHY1(pOE1) cells (FIG. 10, triangles) were grown in zinc-replete SDgal medium. These experiments indicated that $^{65}$Zn uptake in the assay system is transporter-mediated; this process is time-, temperature-, and energy-dependent. At 30° C., zinc accumulation was linear with time for up to 5 minutes after which the uptake rate decreased, and little accumulation was detected with cells incubated at 0° C. or starved for glucose for one hour prior to assay. The rate of zinc uptake was concentration-dependent and saturable (FIG. 8). The Michaelis-Menten kinetic properties differed depending on the medium in which the cells were grown prior to assay. Zinc-replete cells had an apparent $K_m$ of 10±1 μM and $V_{max}$ of 2 pmol/min/10$^6$ cells (FIG. 8A, closed squares). In zinc-limited cells, the apparent $K_m$ was 1±0.1 μM and $V_{max}$ was 80 pmol/min/10$^6$ cells (FIG. 8B, open squares). Thus, uptake activity in zinc-limited cells had a markedly lower apparent $K_m$ and higher $V_{max}$ than the activity observed in zinc-replete cells. These results demonstrate the presence of two zinc uptake systems in yeast, a high affinity system induced by zinc limitation and a low affinity system active in zinc-replete cells.

Zinc uptake assayed in zrt1mutant cells grown in zinc-limiting and zinc-replete media displayed only low affinity activity (FIG. 8A, open and closed circles, respectively). The apparent Km in each case was 10±1 μM and the $V_{max}$ was 1–2 pmol/min/10$^6$ cells. Expressing ZRT1 from the GAL1 promoter (pOE1, FIG. 6) in zinc-replete cells resulted in high affinity uptake activity (apparent $K_m$ of 0.6±0.1 μM) with a $V_{max}$ of 30 pmol/min/10$^6$ cells (FIG. 8B, triangles). No high affinity activity was observed in these cells grown in glucose, in which the GAL1 promoter is not expressed, nor in vector-only control cells grown in galactose or glucose. These results demonstrate that the ZRT1 gene is both necessary and sufficient for high affinity system activity but is not required for low affinity system activity.

Example 9
Regulation of ZRT1 mRNA Levels by Zinc

Figure 9:
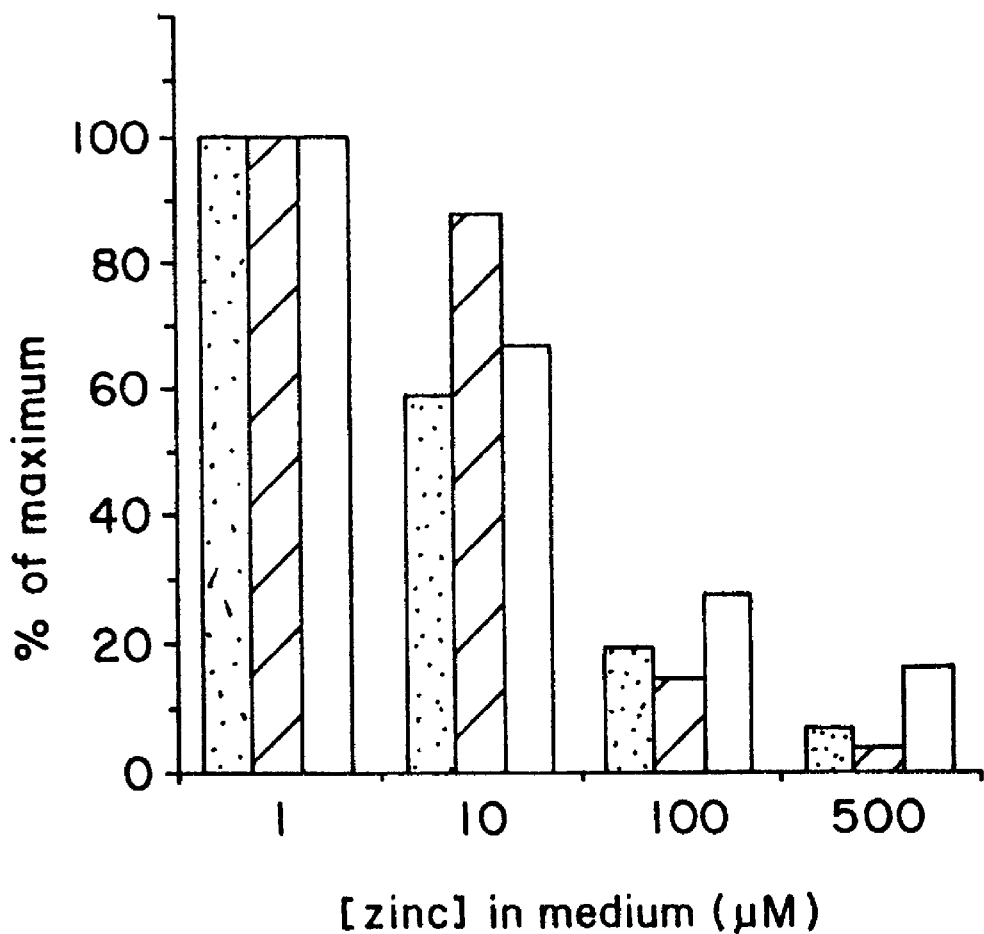
FIG. 9 is a bar graph depicting regulation of the ZRT1 gene and zinc uptake. Shown are the mean values of two experiments each performed in duplicate. The standard deviation within each experiment was less than 10% of the corresponding mean.

The observation that zinc-limited wild type cells possess ZRT1-dependent uptake activity absent in zinc-replete cells suggested that the ZRT1 gene could be regulated by zinc. To test this hypothesis, ZRT1 mRNA levels and zinc uptake activity were measured in cells grown in a range of zinc concentrations. To provide a simpler means of assessing ZRT1 expression, a fusion between the ZRT1 promoter and 5' untranslated region, and the *E. coli* lacZ gene encoding β-galactosidase (pGI 1, FIG. 6) was also constructed. Wild type (DY1457) cells bearing pGI1 were grown to exponential phase in LZM medium supplemented with different concentrations of ZnSO$_4$. The ZRT1 mRNA levels were determined by densitometric scanning and are normalized to the total RNA loaded in each lane (closed bars), and zinc uptake (assayed at 1 μM $^{65}$Zn, hatched bars) and β-galactosidase activities (open bars) were measured. ZRT1 mRNA was regulated in a zinc-dependent manner; zinc-limited cells had 10-fold more ZRT1 mRNA than zinc-replete cells. Uptake activity of the high affinity system closely correlated with ZRT1 mRNA levels and the ZRT1-lacZ fusion was regulated in an identical manner (FIG. 9). The close correlation between ZRT1 expression levels and zinc uptake activity demonstrates that ZRT1 encodes the high affinity transporter. Furthermore, these results show that the ZRT1 gene is regulated at the transcriptional level by zinc and that the ZRT1-lacZ fusion accurately reflects that regulation.

Figure 10A:
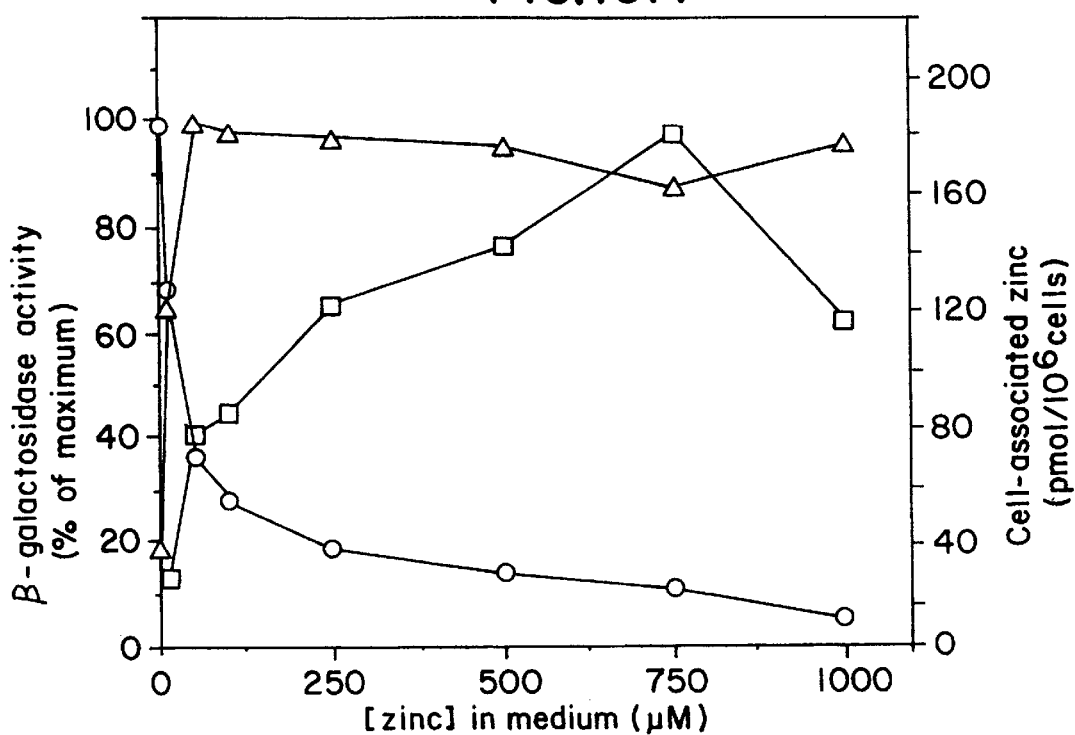
FIGS. 10A and 10B are graphs depicting effects of the zrt1 mutation on ZRT1 regulation and cell-associated zinc levels.

The ZRT1-lacZ fusion allowed for comparison of ZRT1 regulation in wild type and zrt1mutant cells grown over a range of zinc concentrations. Wild type (FIG. 10A, DY1457, open symbols) and zrt1mutant (Figure 10A, ZHY1, closed symbols) transformed with either pGI1 (FIG. 10A, circles) or pHYC3 (the HIS4-lacZ fusion) (FIG. 10A, triangles) were inoculated into LZM media supplemented with the indicated level of $ZnSO_4$, grown for 16 hours, and assayed for β-galactosidase activity. In a parallel experiment, these strains were grown for 16 hours in LZM media containing tracer amounts of $^{65}Zn$ (FIG. 10A, squares). Cells were harvested, and cell-associated zinc was measured. In the wild type strain, β-galactosidase activity was highest in zinc-limited cells and decreased with increasing zinc concentrations in the medium (FIG. 10A). To test if zinc status alters β-galactosidase activity per se, cells bearing a HIS4-lacZ fusion were also assayed. HIS4 encodes a histidine biosynthetic enzyme and is dependent on the GCN4 leucine zipper protein for expression (Lucchini et al. (1984) *Mol. Cell. Biol.* 4:1326–1333). This promoter fusion in wild type cells generated β-galactosidase activity that correlated closely with the strain's growth response to zinc (FIG. 7). Therefore, the repressive effects of zinc on β-galactosidase activity were not caused by zinc toxicity or negative effects of zinc excess on the activity of this enzyme. To estimate the size of the intracellular zinc pool in these cells and determine its relationship to ZRT1 expression, the cell-associated zinc levels in cells grown in LZM containing $^{65}Zn$ were measured. The decrease in ZRT1-dependent β-galactosidase activity coincided with an increase in cell-associated zinc.

Figure 10B:
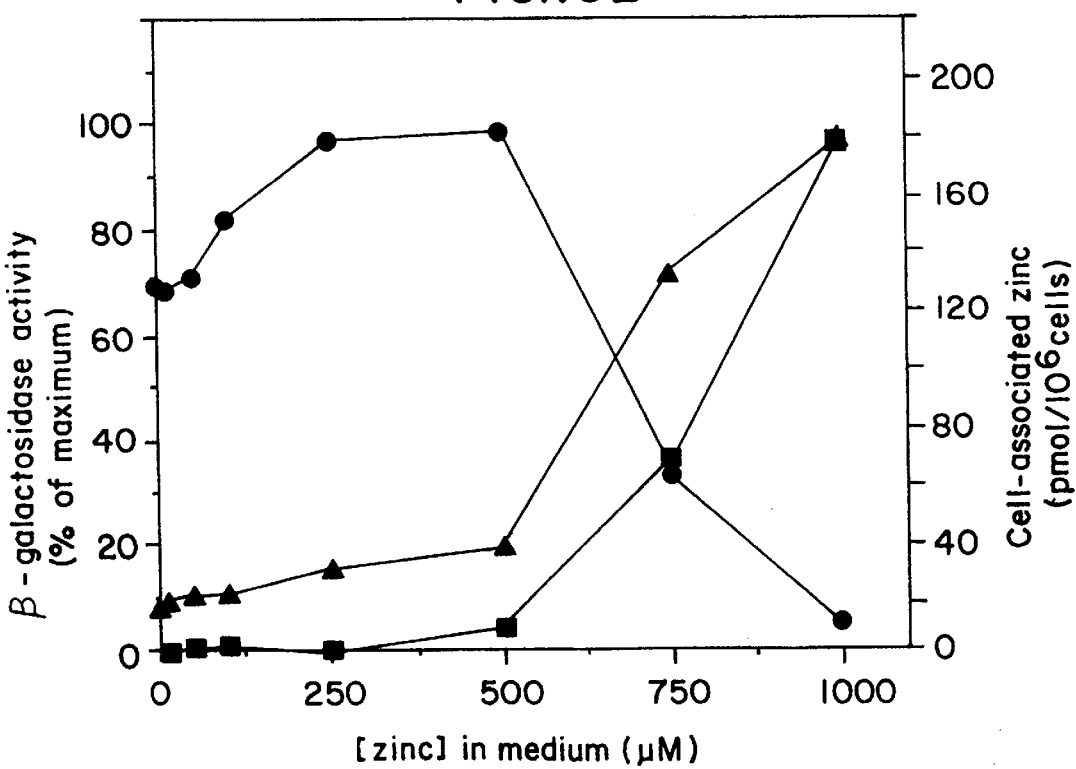

In the zrt1mutant strain, ZRT1-lacZ expression remained at its maximum level in cells grown with much higher concentrations of zinc in the medium than wild type (FIG. 10B). Thus, the zrt1mutant required more zinc in the medium to repress ZRT1 expression than did wild type cells. HIS4-dependent β-galactosidase activity was similar to the growth response of this strain to zinc as well. Finally, although the response of the ZRT1-lacZ fusion to extracellular zinc levels was very different in the wild type and mutant, the response to cell-associated zinc levels was unaffected. For example, approximately equal levels of cell-associated zinc were present in wild type cells grown in LZM+50 μM zinc and zrt1mutant cells grown in LZM+750 μM zinc, and these cells also had similar levels of ZRT1 expression. These data demonstrate that the ZRT1 gene is regulated by intracellular zinc pools and that, although the amount of zinc required in the medium to supply these pools is greatly altered in the mutant, the regulatory system that controls ZRT1 expression in response to pool size is unaffected.

The analyses described herein demonstrate that yeast has two zinc uptake systems. One system has a high affinity for substrate, is induced by zinc limitation, and is necessary for growth in zinc-limiting conditions. The ZRT1 gene encodes the transporter of this high affinity system and several lines of evidence support this hypothesis. First is the similarity between Zrt1p and Irt1p; Irt1p has been demonstrated to be an Fe(II) transporter and may also be capable of transporting zinc. Second, a mutation in the ZRT1 gene eliminated high affinity uptake activity and inhibited growth on zinc-limiting media. Third, overexpressing ZRT1 increased activity of an uptake system that had an apparent $K_m$ almost identical to that of the high affinity system. These results indicate that ZRT1 expression is both necessary and sufficient for high affinity system activity. It has also been found that high affinity activity and ZRT1 expression was closely correlated across a wide range of extracellular zinc concentrations. It is formally possible that Zrt1p is only one subunit of a heteromeric transporter complex, but this is unlikely given that overexpression of ZRT1 alone increased high affinity activity.

ZRT1 is the first influx zinc transporter gene from any organism to be characterized at the molecular level. Neither Irt1p nor Zrt1p contain ATP binding domains, suggesting that uptake is driven by indirect coupling to energy metabolism, perhaps through a gradient of another ion such as $K^+$ (Fuhrmann and Rothstein (1968) *Biochim. Biophys. Acta* 163:325–330; Okorokov et al. (1983) *Biochem. Int.* 6:463–472). A group of histidine residues found in Irt1p was conserved in Zrt1p. This region is a metal-binding domain given that the imidazole ring nitrogens of histidine may serve as coordinating ligands for metal ions. In both proteins, this sequence is found in a loop region predicted to be on the cytoplasmic surface of the membrane. Similar histidine-rich sequences are also found in the three eukaryotic proteins implicated in zinc detoxification, i.e. Zrc1p, Cot1p, and Znt-1p (Conklin et al. (1992) *Mol. Cell Biol.* 12:3678–3688; Kamizono et al. (1989) *Mol. Gen. Genet.* 219:161–167; Palmiter and Findley (1995) *EMBO J.* 14:639–649). In each case, the domain is predicted to be cytoplasmically located. This conservation suggests that the domain plays an important functional role in Irt1p and Zrt1p. For example, these histidines may serve as a means of feedback regulation of zinc transport. High intracellular zinc levels could result in binding of zinc by Zrt1p and reduce the activity of the transporter.

Zinc limitation induces activity of the high affinity system. Because the results show that this system is regulated at the transcriptional level, a zinc finger DNA-binding protein may sense intracellular zinc levels to regulate ZRT1 expression. However, a mechanism that controls mRNA stability through sequence elements located in the 5' untranslated region of the mRNA cannot be ruled out. Whatever the mechanism, the high affinity system is clearly regulated in response to the intracellular zinc content. This is demonstrated by the fact that the ZRT1-lacZ fusion gene shows a similar response to cell-associated zinc levels in both wild type and zrt1mutants despite a 75-fold difference in their response to external levels of zinc. Thus, the regulatory system that controls ZRT1 expression in response to intracellular zinc pools is unaffected in the zrt1mutant. It has also been found that zrt1 mutant is not any more resistant to high extracellular zinc levels than wild type cells. This result is consistent with the low level of ZRT1 expression observed in zinc-replete cells and demonstrates that the high affinity uptake system does not play an important role in zinc toxicity.

Example 10

Low Affinity Zinc Uptake

Zinc accumulation by the low affinity system was assayed in zrt1mutant cells in which the high affinity system has been eliminated. Mutant zrt1(ZHY 1) cells were grown in LZM supplemented with 1 mM $ZnCl_2$. Cells were incubated with 10 μM $^{65}$Zn for the indicated times at either 0° C. (FIG. 11, closed squares) or 30° C. (FIG. 11, open squares). Shown is a representative experiment in which each point is the average of two values, each within 15% of the mean. The low affinity system was measured in zrt1mutant cells (FIG. 11, ZHY1, closed bars) that were grown to exponential phase in LZM supplemented with 1 mM $ZnCl_2$ and assayed for zinc uptake with 20 μM $^{65}$Zn for five minutes in the absence (-, control) or presence of 200 μM other metals. High affinity uptake was measured in zinc-limited wild type (FIG. 11, DY1457, hatched bars) grown in LZM supplemented with 10 μM $ZnCl_2$ and assayed for zinc uptake with 2 μM $^{65}$Zn for five minutes in the absence (-, control) or presence of 20 μM other metals. The control rate of uptake was 0.9 pmol/min/$10^6$ cells for the low affinity system and 47 pmol/min/$10^6$ cells for the high affinity system. Fe(II) was supplied in the presence of 1 mM ascorbate, a reducing agent found in control experiments to have no effect on the rate of zinc uptake by either low or high affinity systems. The asterisks indicate values significantly different from control values (P<0.05). When incubated at 0° C., these cells accumulated little zinc (FIG. 11A). At 30° C., cell-associated zinc levels increased linearly with time for up to 40 minutes. Similar results were obtained with wild type cells grown under zinc-replete conditions in which the high affinity system is not expressed. Thus, zinc accumulation by the low affinity system is time- and temperature-dependent. This accumulation was also dependent on glucose; after five minutes at 30° C. in 10 μM $^{65}$Zn, glucose-starved zrt1cells had no detectable zinc accumulation whereas the same cells incubated with glucose accumulated 3.7 pmol/$10^6$ cells. Taken together, these data demonstrate that zinc accumulation by the low affinity system occurs through an uptake mechanism rather than by adsorption of the metal to the cell surface. To assess the substrate specificity of this system, several metals were tested for their ability to inhibit zinc uptake by zrt1mutant cells (FIG. 11B). The concentration of the added metals in these assays was 10-fold higher (200 μM) than the radioactive zinc concentration (20 μM). The addition of excess nonradioactive zinc reduced the uptake rate of radioactive zinc to approximately 10% of the control rate. Cu and Fe(II) also inhibited zinc uptake by the low affinity system (32 and 79% of the control rate) but to a lesser extent than nonradioactive zinc (P<0.05). Co, Fe(III), Mg, Mn, and Ni did not diminish zinc uptake by the low affinity system. These results demonstrate that while Cu and Fe(II) can potentially be substrates, the low affinity system prefers zinc over other metals.

To compare the substrate specificities of the low and high affinity uptake systems, these metals were tested to determine whether they could inhibit uptake by the high affinity system under similar conditions (FIG. 11B). Again, the concentration of added metal was 10-fold higher (20 μM) than the radioactive zinc concentration (2 μM). As with the low affinity system, the high affinity system was unaffected by Co, Fe(III), Mg, Mn, and Ni whereas Fe(II), Cu, and, to a far greater extent, Zn, were inhibitory of high affinity uptake (P<0.05). In fact, the only significant difference between these systems was that Cu was more inhibitory to the low affinity system than it was to the high affinity system. These results demonstrate that the high and low affinity systems are closely related. This conclusion is supported by the high degree of sequence similarity between the Zrt1p high affinity transporter and the product of the ZRT2 gene. As described herein, the experiments demonstrate that ZRT2 encodes the low affinity zinc transporter.

Example 11
Identification of the ZRT2 Gene

The ZRT2 gene was identified as an open reading frame (ORF) of unknown function during sequence analysis of the yeast genome (GenBank™ accession number X91258). The hypothesis that ZRT2 encodes the low affinity zinc transporter was suggested by the close similarity of its predicted amino acid sequence to that of Zrt1p (Zhao and Eide (1996) *Proc. Natl. Acad. Sci. USA* 93:2454–2458). This hypothesis was further supported by the isolation of ZRT2 as a multicopy suppressor of the zinc-limited growth defect of a zrt1mutant. Multicopy suppressors are genes that, when overexpressed due to the increased gene dosage provided by a multicopy plasmid vector, reduce the phenotypic effects of a mutation in another gene (Rine, J. (1991) *Methods Enzymol.* 194: 239–251). Overexpression of the low affinity transporter could suppress the zinc-limited growth defect of the zrt1 mutant and a multicopy plasmid containing the ZRT2 gene, pMC4, was isolated in this way. This plasmid is a weaker suppressor of the zrt1 mutation than a multicopy plasmid containing a genomic copy of ZRT1 (pMC5), i.e. pMC4 restored ability of the zrt1mutant to grow on moderately zinc-limiting conditions but not on severely zinc-limited media where pMC5 could still complement the growth defect. This result is consistent with the 10-fold difference in apparent $K_m$ values of the high and low affinity systems.

The plasmid pMC4 contains a 9 kp insert derived from chromosome XII, immediately adjacent to the ACE2 gene (Butler and Thiele (1991) *Mol. Cell Biol.* 11:476–485).

This fragment contains four ORFs originally designated L3120, L3116, L3111, and L3105 (FIG. 12). ORF L3120 is the gene that has been named ZRT2. The amino acid sequence of Zrt2p is related to that of Zrt1p and Irt1p (44% and 35% identity, respectively) (FIG. 13). All three proteins are predicted to contain eight transmembrane domains, numbered I-VIII in FIG. 13, and these domains show the greatest degree of sequence similarity among these proteins. The sequence alignment shown in FIG. 13 also indicates that transmembrane domains III and IV are separated by a region of variable length and sequence. The different lengths of this "variable region" largely accounts for the different overall sizes of these three proteins. Both Irt1p and Zrt1p contain a cluster of 3 to 4 histidine residues in the variable region that is a metal-binding domain and these histidines are also found in Zrt2p. Moreover, the variable regions of Zrt2p and Zrt1p carry a highly negative net charge. Zrt2p contains a total of 26 acidic residues in its 142 amino acid variable region (i.e., 18%) and Zrt1p contains 14 acidic residues in its 72 amino acid variable region (19%). These acidic residues could also contribute to metal binding. The membrane topologies of all three proteins, as predicted by the "positive-inside" rule (Claros and von Heijne (1994) *Comput. Appl. Biosci.* 10:685–686), show that their variable regions are located on the cytoplasmic surface of the membrane.

Example 12
ZRT2 Overexpression Increases Low Affinity Uptake

Figure 14B:
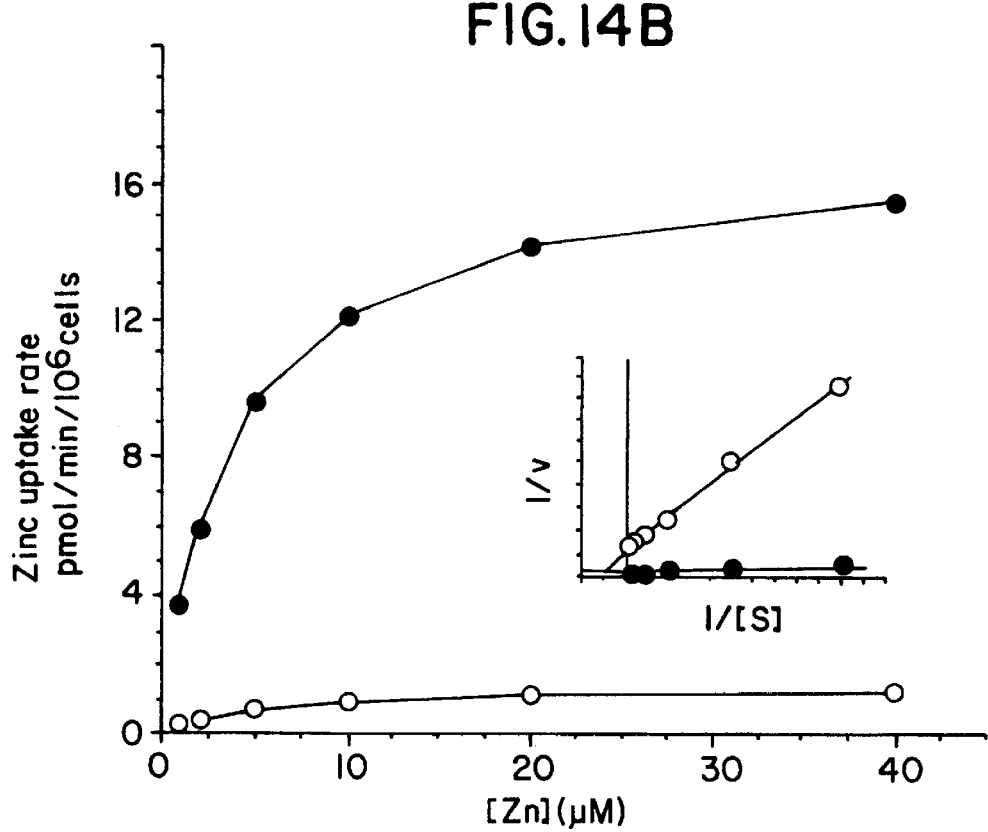

Plasmid pMC4 suppresses the growth defect of a zrt1 mutant on zinc-limited media. Given the high degree of similarity between Zrt1p and Zrt2p, this suppression was likely to result from increased expression of the ZRT2 gene and a concomitant increase in zinc uptake. To test this hypothesis, zinc uptake was assayed with yeast transformed with either pMC4 or the vector, YEp24. ZHY1 (zrt1) cells transformed with either pMC4 (closed squares) or the vector YEp24 (FIG. 14, open squares) were grown to exponential phase in SD glucose medium and assayed for zinc uptake rate over a range of $^{65}$Zn concentrations. ZHY1 (zrt1) cells transformed with pOE2 (FIG. 14, closed circles) or the vector pRS316-GAL1 (FIG. 14, open circles) were grown to exponential phase in SD galactose medium and assayed for zinc uptake over a range of $^{65}$Zn concentrations. At all concentrations tested, pMC4 transformants had an approximately 15-fold higher rate of zinc uptake than the corresponding vector control (FIG. 14). To determine if the pMC4-dependent increase in uptake rate is due to overexpression of the ZRT2 gene rather than overexpression of one of the three other ORFs present in the pMC4 insert, the ZRT2 ORF was cloned into an expression vector under control of the GAL1 promoter (pOE2, FIG. 12). This plasmid was found to suppress the zrt1zinc-limited growth defect on galactose-containing media where the GAL1 promoter is expressed, but not on glucose-containing media where it is inactive). Cells overexpressing Zrt2p from pOE2 also had increased zinc uptake rates relative to their vector-only control (FIG. 14B). Thus, ZRT2 overexpression per se increases zinc uptake activity.

The higher uptake rate observed in ZRT2 overexpressing cells could result from increased activity of the low affinity system or increased activity of a third, previously unknown, zinc uptake system. To address this question, the Michaelis-Menten kinetic properties of the data presented in FIG. 14 were determined using Lineweaver-Burk reciprocal plots (FIG. 14, insets). Although the Vmax values are much higher in the ZRT2 overexpressing strains, the apparent Km values are very similar to those of the low affinity system measured in the corresponding vector-only controls (Table 3A).

TABLE 3

Effects of ZRT2 overexpression and disruption on the Michaelis-Menten kinetic properties of zinc uptake

| A. Plasmid | $K_m^a$ | $V_{max}^b$ |
|---|---|---|
| pMC4 | 8.0 ± 0.4 | 28 ± 1 |
| vector | 9.5 ± 0.8 | 2.2 ± 0.1 |
| pOE2 | 3.6 ± 0.1 | 17 ± 2 |
| vector | 10 ± 1 | 2.0 ± 0.1 |

| B. Strain | Growth Medium [Zn] | $K_m^a$ | $V_{max}^b$ |
|---|---|---|---|
| wild type | low | 0.52 ± 0.07 | 76 ± 2 |
| zrt2 | low | 0.85 ± 0.18 | 60 ± 2 |
| wild type | high | 15 ± 3 | 0.60 ± 0.03 |
| zrt2 | high | 0.40 ± 0.04 | 0.31 ± 0.01 |
| zrt1 | high | 10 ± 1 | 0.52 ± 0.04 |
| zrt1zrt2 | high | N.D. | N.D. |

$^a$µM total zinc (mean ± SE)
$^b$pmol/min/10$^6$ (mean ± SE)

A. Kinetic analysis of the data presented in FIG. 14. B. Kinetic analysis of the data presented in FIG. 15. Low growth medium [Zn] values were derived from the data in FIG. 15A and high growth medium [Zn] values were derived from the data in FIG. 15B. The apparent $K_m$ (in terms of [Zn]T) and $V_{max}$ values were calculated from Lineweaver-Burk reciprocal plots. N.D.-uptake not detectable.

These results show that ZRT2 overexpression increases the activity of the low affinity system. pMC4- and pOE2-dependent uptake activity was inhibited by Cu and Fe(II) to the same degree that these metals inhibited the low affinity system but not by any of the metals that do not inhibit the low affinity activity. The lower apparent Km observed in the pOE2 overexpressing strains was reproducible.

Example 13
ZRT2 is Required for Low Affinity Uptake

To determine if ZRT2 is required for the low affinity system to function, a disruption mutation in this gene was constructed. This allele, designated zrt2::HIS3, was constructed by inserting the wild type HIS3 gene into the center of the ZRT2 ORF (FIG. 13). The disruption allele was transformed by gene transplacement into wild type and zrt1 haploid strains and viable zrt2::HIS3 mutants were obtained in both. These results show that ZRT2 is not an essential gene, even in a zrt1 mutant strain where the high affinity uptake system has been eliminated.

Figure 15A:
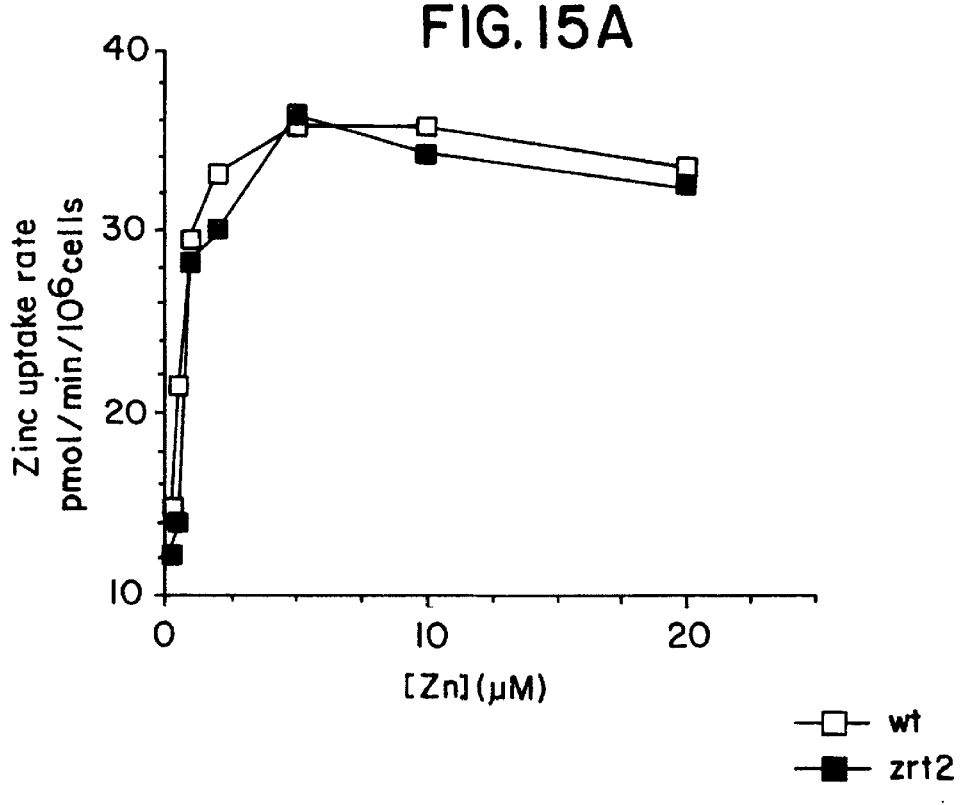
Figure 15B:
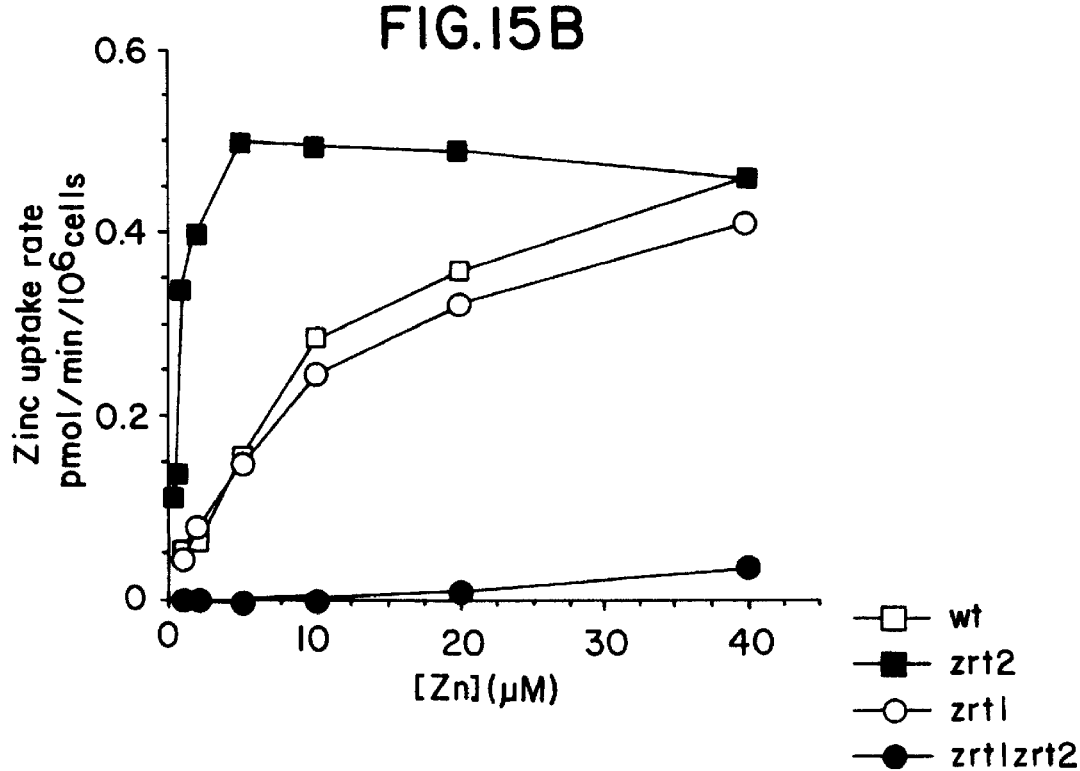

Zinc uptake assays were performed on wild type, zrt1, zrt2, and zrt1zrt2 mutant strains to determine if the zrt2 mutation altered the activity of either the low or high affinity zinc uptake systems. Wild type (DY1457), zrt2 (ZHY2), zrt1(ZHY1) and zrt1zrt2 (ZHY3) cells were grown to exponential phase and assayed for zinc uptake rate over a range of $^{65}$Zn concentrations. Zinc-limited cells were grown in LZM supplemented with 10 µM ZnCl$_2$ prior to assay. Zinc-replete cells were grown in LZM supplemented with 1.5 mM ZnCl$_2$ prior to assay. In zinc-limited cells, no difference in the activity of the high affinity system was observed in the zrt2 mutant relative to the wild type strain (FIG. 15A). Calculations of the apparent $K_m$ and $V_{max}$ from these data confirmed the conclusion that the zrt2 mutation does not affect the high affinity system (Table 3B). Zinc-replete wild type and zrt1mutant cells had similar levels of low affinity activity (FIG. 15B, Table 3B). In the zrt2 single mutant, however, the low affinity system was eliminated and apparently replaced by increased activity of the high affinity system (FIG. 15B). The apparent $K_m$ of uptake in zrt2 cells was similar to the apparent $K_m$ of the high affinity system (Table 3B). Furthermore, neither low nor high affinity activity was detected in the zrt1zrt2 mutant. These results demonstrate the ZRT2 gene is required for function of the low affinity uptake system but is not necessary for high affinity activity.

Example 14
The Low Affinity System is a Relevant Source of Zinc

The presence of high affinity uptake activity in zrt2 mutants grown in a zinc-rich medium demonstrates that the low affinity system is a relevant source of zinc; these cells have increased the activity of their high affinity system to compensate for the loss of the low affinity system. The relevance of the low affinity system as a source of zinc was also indicated by the observation that the activity of this system is zinc-regulated. Mutant zrt1 cells grown in a zinc-replete medium (SD glucose) had a zinc uptake rate of 1.7 pmol/min/10$^6$ cells when assayed at 10 µM $^{65}$Zn. However, cells grown in the same medium supplemented with extremely high levels of ZnCl$_2$ (2 mM) had an uptake rate only 7% (0.12 pmol/min/10$^6$ cells) of the rate observed in the untreated cells. No difference in growth rate was observed between these two culture conditions indicating that this lower activity was not due to toxic effects of the metal.

Figure 16A:
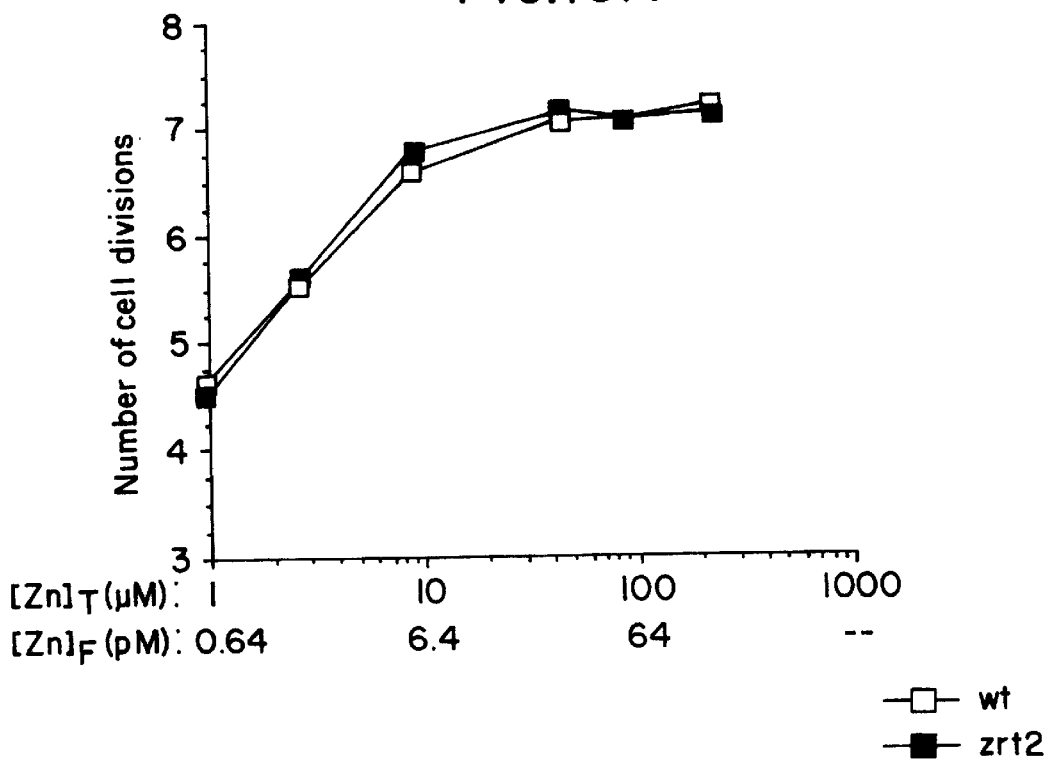

To further assess the role of the low affinity system as a source of zinc, growth of wild type and zrt2 cells in a zinc-limiting medium, LZM, supplemented with increasing amounts of zinc was examined. The same strains as in FIG. 15 were grown for six hours in SD glucose medium, harvested, washed in LZM, and reinoculated into either LZM (FIG. 15A) or LZM-EDTA (FIG. 15B) supplemented with the indicated concentrations of ZnCl$_2$ ([Zn]T). These cultures were then grown for 16 hours at 30° C. prior to cell number determination. Number of cell divisions are plotted against [Zn]T and the calculated free zinc concentration ([Zn]F). The metal ion buffering capacity of EDTA in LZM is exceeded at concentrations above 100 μM total zinc whereas the metal buffering capacity of citrate in LZM-EDTA maintains a linear relationship between [Zn]T and [Zn]F to concentrations greater than 1 mM. It has been shown previously that the zrt1 mutant requires greater than 500 μM total zinc ([Zn]T) in LZM to undergo its maximum number of cell divisions and this value corresponds to a calculated free (i.e. unchelated) zinc concentration ([Zn]F) of approximately 500 pM. However, no difference in zinc requirement was observed between the wild type and zrt2 strains where as little as 10 μM total zinc (~6 pM [Zn]F) was sufficient for maximum growth yield (FIG. 16A). This result was expected given that the high affinity system, which would be more important than the low affinity system for zinc-limited growth, is not reduced in activity by the zrt2 mutation.

Figure 16B:
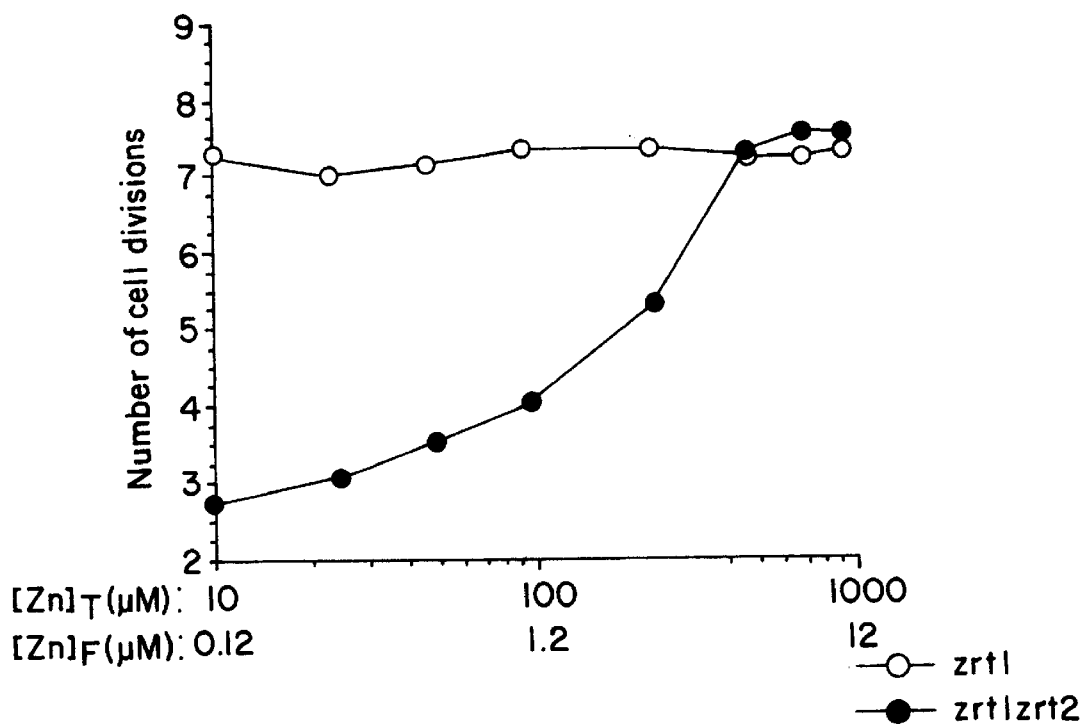

LZM is zinc-limiting because of the presence of 1 mM EDTA, a high affinity zinc chelator. The zinc requirement of the zrt1 and the zrt1zrt2 strains was determined in LZM-EDTA medium. LZM-EDTA is less zinc-limiting than LZM at a given concentration of total zinc because citrate, the predominant chelator in LZM-EDTA, binds the metal with lower affinity than EDTA. While the zrt1single mutant divided its maximum number of times in LZM-EDTA with as little as 0.5 μM total zinc (~6 nM [Zn]F), the zrt1zrt2 mutant required 500 μM total zinc (~6 μM [Zn]F) to do so (FIG. 16B). Thus, zrt1zrt2 mutants are hypersensitive to zinc-limitation and require at least 1000-fold more zinc for growth than the zrt1strain. Given that the zrt1mutant already requires 100-fold more zinc than the wild type strain for optimal growth, this result shows that the zrt1zrt2 mutant requires greater than $10^5$-fold more zinc in the medium than the wild type strain.

The effects of the zrt2 mutation on the regulation of the ZRT1 gene was also examined. Previous studies demonstrated that ZRT1 is regulated at the transcriptional level by a regulatory pool of intracellular zinc and that ZRT1 expression increases when this pool level is low. Furthermore, cell-associated zinc levels are much lower in the zrt1mutant grown in zinc-limiting conditions. At higher concentrations of extracellular zinc, however, these levels increased to the wild type levels. It was proposed that this accumulation was the result of zinc uptake by the low affinity system. To test this hypothesis and determine the effect of the zrt2 mutation on the pool of intracellular zinc that regulates ZRT1 gene expression, β-galactosidase activity from the ZRT1-lacZ fusion in wild type, zrt1, zrt2, and zrt1zrt2 mutant strains grown in media supplemented with a broad range of zinc concentrations was measured. The same strains as in FIG. 15 bearing the ZRT1-lacZ fusion gene (pGI1) were grown for six hours in SD glucose medium, harvested, washed in LZM, and reinoculated into either LZM (FIG. 15A) or LZM-EDTA (FIG. 15B) lacking uridine and supplemented with the indicated concentrations of ZnCl2 ([Zn]T). These cultures were then grown for 16 hours at 30° C. prior to being assayed for β-galactosidase activity. These values are also plotted against the calculated free zinc concentration ([Zn]F). The 100% values of β-galactosidase activity were 140, 130, 86, and 105 units for wild type, zrt2, zrt1, and zrt1zrt2, respectively. ZRT1-lacZ β-galactosidase activity in the zrt2 mutant was indistinguishable from the activity in wild type cells (FIG. 17A). This result shows that ZRT1 regulation in response to the regulatory pool of intracellular zinc is not greatly altered by the zrt2 mutation. As noted previously, the high affinity system is induced in zrt2 mutants growing in zinc-rich media (FIG. 15B), yet no increase in β-galactosidase activity was observed in this experiment. This apparent contradiction can be explained by the observation that the high affinity activity observed in the zrt2 mutant is very low (i.e. only 1–2% of the maximum activity) and β-galactosidase assays may be too insensitive to reliably detect this slight increase in expression.

ZRT1-lacZ expression was greatly altered in the zrt1zrt2 strain. While β-galactosidase activity in the zrt1mutant decreased to its minimal level with as little as 10 μM total zinc (~0.12 μM $[Zn]_F$), expression in the zrt1zrt2 mutant was down-regulated only at total zinc concentrations of 200 μM (~2.4 μM [Zn]F) or higher (FIG. 17B). These results suggest that the regulatory pool of intracellular zinc is at a lower level in the zrt1zrt2 strain grown under these conditions than in the zrt1single mutant. This conclusion was supported by measurements of cell-associated zinc in these strains. At 10 μM total zinc, cell-associated zinc in the zrt1strain was 133±12 pmol/$10^6$ cells, compared with 5±0.6 pmol/$10^6$ cells in the zrt1zrt2 strain. At 1000 μM total zinc, the zrt1strain had a cell-associated zinc level of 168±14 pmol/$10^6$ cells and the zrt1zrt2 level rose to 86±21 pmol/$10^6$ cells. Taken together, these results demonstrate that Zrt2p and the low affinity system contribute to the accumulation of zinc into the intracellular zinc pool that controls ZRT1 expression.

Previous studies suggested that at least two zinc uptake systems are present in *S. cerevisiae*. The high affinity system has an apparent $K_m$ of 1 μM total zinc which corresponds to a calculated free zinc concentration of ~10 nM. The low affinity system has an apparent $K_m$ of 10 μM total zinc which corresponds to ~100 nM free zinc. ZRT2 encodes the transporter of the low affinity system. Consistent with this hypothesis, the ZRT2 gene was isolated as a multicopy suppressor of the zinc-limited growth defect of a zrt1 mutant. Furthermore, the level of ZRT2 expression correlated with low affinity uptake activity. ZRT2 overexpression increased the activity of a system biochemically indistinguishable from the low affinity system. Conversely, disruption of the ZRT2 gene eliminated low affinity uptake. Thus, ZRT2 expression is both necessary and sufficient for low affinity activity. The predicted amino acid sequence of Zrt2p also shows that this protein plays a direct role in the transport of zinc. Zrt2p shares remarkable similarity with Zrt1p and Irt1p, an Fe(II) transporter from *A. thaliana* described herein. The distribution of hydrophobic amino acids demonstrates that all three gene products are integral membrane proteins with eight transmembrane domains. Zrt2p may be only one subunit of a heteromeric transporter complex, but this hypothesis is unlikely given that overexpression of ZRT2 alone increases zinc uptake activity.

ZRT2 is a member of a new and rapidly growing gene family of putative metal transporters. Closely related genes in organisms as diverse as fungi, plants, nematodes, and humans have been indentified. Given that three members of this family, IRT1, ZRT1, and, now, ZRT2 have been implicated in metal transport, it is likely that the other genes in this family play similar roles in metal metabolism. The structural similarity of these different gene products shows that they may use a similar mechanism to transport their substrates. Zinc uptake in yeast requires metabolic energy (White and Gadd (1987) *J. Gen. Micorbiol.* 133:727–737). Like the other members of this family, Zrt2p does not contain ATP-binding domains, nor does the protein bear any significant similarity to the ubiquitous β-type ATPase family of transport proteins. This observation shows that uptake may be driven by indirect coupling to energy metabolism, perhaps through the electrical potential generated across the plasma membrane by the plasma membrane ATPase. Alternatively, uptake may be driven by a transmembrane gradient of another ion. Uptake of zinc by the low affinity system was not inhibited by high extracellular K$^+$(100 mM) indicating that a zinc/K$^+$antiport mechanism, as has been previously proposed (Fuhrmann and Rothstein (1968) *Biochim. Biophys.* Acta 163:325–330; Okorokov et al. (1983) *Biochem. Int.* 6:463–472), is unlikely.

A cluster of histidines in Zrt2p is also found in Zrt1p, Irt1p, and the other members of this gene family. In Zrt2p and Zrt1p, these histidines are located in a region with a highly negative net charge due to the abundance of acidic amino acids. Imidazole ring nitrogens and carboxylate groups frequently serve as coordinating ligands for zinc (Vallee and Auld (1990) *Biochemistry* 9:5647–5659) so these amino acids may be responsible for binding the metal substrate. In all of these proteins, the histidines are found in a region between two transmembrane domains that is predicted to be exposed on the cytoplasmic face of the membrane. Given this location, these amino acids may act in a late step in the uptake process by binding the metal after it has been transported across the membrane. Alternatively, these histidines may serve as part of a feedback regulation system. High intracellular zinc levels could result in binding of zinc to Zrt2p and, by some mechanism, reduce the activity of the transporter. Whatever their role, the conservation of these histidine residues within the IRT/ZRT gene family suggests that they are critical to the function of these proteins. This conclusion is further supported by the observation that similar histidine-rich domains are found in the sequences of four transport proteins implicated in zinc detoxification, i.e. Zrc1p and Cot1p from yeast and the mammalian ZnT-1p and ZnT-2p proteins (Conklin et al. (1994) *Mol. Gen. Genet.* 244:303–311; Conklin et al. (1992) *Mol. Cell Biol.* 12:3678–3688; Kamizono et al. (1989) *Mol. Gen. Genet.* 219:161–167; Palmiter and Findley (1995) *EMBO J.* 14:639–649; Palmiter et al. (1996) *EMBO J.* 15:1784–1791). These proteins are apparently efflux transporters that transport metal ions from the cytoplasm either into an intracellular compartment or outside of the cell and, aside from the histidine-rich domain, share no significant similarity with the IRT/ZRT gene family. In each case, the histidine-rich domain is predicted to be cytoplasmically located. Furthermore, the interplay between zinc uptake transporters like Zrt1p and Zrt2p and efflux transporters like ZnT-1p and ZnT-2p likely plays an important role in cellular zinc homeostasis.

The results described herein demonstrate that the high and low affinity systems are genetically and biochemically separable uptake pathways. It has also been shown that the low affinity system is a relevant source of zinc for growing yeast cells. First, metal inhibition studies indicate that the low affinity system is very similar to the high affinity system in its specificity for zinc over other metals. Second, the low affinity system is the major pathway for zinc uptake in wild type cells grown in zinc-replete conditions (e.g. cells grown in SD glucose medium); no high affinity activity is detectable in these cells. Third, a zrt2 mutant strain that lacks the low affinity system has increased high affinity activity. This increased activity is presumably to compensate for loss of low affinity activity. In addition, the zrt1zrt2 mutant requires greater than 1000-fold more zinc in the medium to grow and to supply the regulatory pool of intracellular zinc and down-regulate the zinc-responsive ZRT1 promoter than does the zrt1single mutant. These results demonstrate that the low affinity system is a major contributor to zinc accumulation in the zrt1 strain and it also contributes to wild type zinc accumulation under the same growth conditions.

Additional evidence that the low affinity system is a relevant source of zinc is provided by the observation that this system is regulated by zinc. Low affinity activity was diminished in cells grown in a medium containing extremely high levels of zinc (2 mM). The high affinity system and ZRT1 mRNA levels are regulated by zinc and this regulation is mediated at the transcriptional level in response to an intracellular zinc pool. The analysis of the low affinity system described here does not distinguish between transcriptional and post-ranscriptional mechanisms. One possible mechanism, as discussed above, is down-regulation of the low affinity system by feedback inhibition of transporter activity. What is clear is that the regulatory systems that control high and low affinity uptake are responsive to very different levels of cell-associated zinc. A decrease in ZRT1 expression and high affinity activity was apparent when cell-associated zinc levels rose to as little as 30 pmol/10$^6$ cells. In that same analysis, it was found that cells with a cell-associated zinc level of 120 pmol/min/10$^6$ cells still had maximum low affinity activity ($V_{max}$=2 pmol/min/10$^6$ cells). Therefore, down-regulation of the low affinity system requires much higher levels of cell-associated zinc than is needed to repress the high affinity system. These observations pose an interesting regulatory question as to how these two systems respond to different levels of presumably the same signal, intracellular zinc.

It has been demonstrated herein that zrt1mutant cells are not more resistant to higher levels of extracellular zinc than are wild type cells. Neither zrt2 nor zrt1zrt2 strains are more resistant to extracellular zinc than are the wild type or zrt1strains. This observation is consistent with the low level of both high and low affinity activity observed in cells treated with extremely high levels of zinc and demonstrates that neither of these two systems plays a major role in zinc toxicity. Toxicity may result from zinc accumulation by one or more additional uptake pathways. The existence of this pathway(s) is demonstrated by the observation that a strain lacking both the high and low affinity systems, the zrt1zrt2 mutant, is still viable. Undoubtedly, these cells are obtaining zinc and this uptake may represent the activity of a third system for zinc accumulation. The identity of this third system is suggested by earlier studies in which zinc uptake in yeast was attributed to a "divalent cation uptake system" that was also capable of transporting Mg, Co, Mn, and Ni (Fuhrmann and Rothstein (1968) *Biochim. Biophys.* Acta 163:325–330). The apparent $K_m$ of zinc uptake by this system was estimated to be approximately 500 μM total zinc, i.e. 50- and 500-fold higher than the ZRT2- and ZRT1 -dependent systems, respectively. This apparent $K_m$ is consistent with the high concentration of zinc required to confer maximum growth to the zrt1zrt2 mutant. Whatever the mechanism, given the 10$^5$-fold greater zinc requirement of the zrt1zrt2 mutant strain compared to the wild type, it is unlikely that this third pathway plays a significant role in zinc accumulation under any but the most zinc-rich conditions.

Example 15

Complementation of The ZRT1 ZRT2 Strain to Identify The Zip Genes

The zrt1zrt2 strain ZHY3 (MAαade6 can1 his3 leu2 trp1 ura3 zrt1::LEU2 zrt2::HIS3) was transformed using standard procedures with a plasmid library containing Arabidopsis cDNA inserted under the control of the phosphoglycerate kinase promoter in pFL61 (Minet et al. (1992) *Plant J.* 2(3):417–22). The poly(A)+RNA used to construct this library was isolated from young whole seedlings (stage two leaves). The transformants were plated onto SD glucose medium plus adenine histidine, leucine, and tryptophan (i.e., -uridine). 300,000 Ura+transformants were screened and cells giving rise to large colonies were selected for further analysis.

Example 16
Preparation of Antibodies Against an IRT1 Peptide

A peptide was synthesized which spans amino acids 162 through 184 of IRT1: Acetyl-C-PANDVTLPIKEDDSN-amide (SEQ ID NO:21) (Quality Controlled Biochemicals, Inc.). This peptide was then used as an antigen to raise polyclonal m antibodies in rabbits (Quality Controlled Biochemicals, Inc.). A western blot of total protein prepared from Arabidopsis demonstrated that the antibodies recognize a protein of approximately 33 KDa which is only present in iron-starved plants. These antibodies have been further affinity-purified.

Example 17
Zinc Uptake by Zips

Using the standard Zn uptake assay described above, there is essentially no detectable zinc uptake (5 minute time course using 10 mM Zn) by the zrt1zrt2 double mutant strain, ZHY3. The same strain, ZHY3, containing the ZIP1 gene has a Zn uptake rate of 191 fmol/min/10e6 cells. ZIP3 containing cells have a Zn uptake rate of 134 fmol/min/10e6 cells. Cells containing ZIP2 show no Zn uptake under these conditions.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. An isolated nucleic acid molecule comprising a nucleotide sequence having a nucleotide sequence that is identical to at least about 45% of the entire nucleotide sequence shown in SEQ ID NO:1, SEQ ID NO:3, SEQ ID NO:5, SEQ ID NO:7 SEQ ID NO:13, or a full complement thereof.

2. The nucleic acid molecule of claim 1 comprising a nucleotide sequence shown in SEQ ID NO:1, or a full complement thereof.

3. The nucleic acid molecule of claim 1 comprising a nucleotide sequence shown in SEQ ID NO:3, or a full complement thereof.

4. The nucleic acid molecule of claim 1 comprising a nucleotide sequence shown in SEQ ID NO:5, or a full complement thereof.

5. The nucleic acid molecule of claim 1 comprising a nucleotide sequence shown in SEQ ID NO:7, or a full complement thereof.

6. The nucleic acid molecule of claim 1 comprising a nucleotide sequence shown in SEQ ID NO:13, or a full complement thereof.

7. The nucleic acid molecule of claim 1, which encodes a polypeptide having the ability to transport one or more of the metals selected from the group consisting of Fe(II), Cd. Co Mn Pb, Hz and Zn.

8. The nucleic acid molecule of claim 1, which encodes a polypeptide comprising an amino acid sequence shown in SEQ ID NO:2.

9. The nucleic acid molecule of claim 1, which encodes a polypeptide comprising an amino acid sequence shown in SEQ ID NO:4.

10. The nucleic acid molecule of claim 1, which encodes a polypeptide comprising an amino acid sequence shown in SEQ ID NO:6.

11. The nucleic acid molecule of claim 1, which encodes a polypeptide comprising an amino acid sequence shown in SEQ ID NO:8.

12. The nucleic acid molecule of claim 1, which encodes a polypeptide comprising an amino acid sequence shown in SEQ ID NO:14.

13. The nucleic acid molecule of claim 1, which encodes a polypeptide comprising an amino acid sequence having an amino acid sequence that is identical to at least about 45% of an amino acid sequence shown in SEQ ID NO:2, SEQ ID NO:4, SEQ ID NO:6, SEQ ID NO:8 or SEQ ID NO:14.

14. The nucleic acid molecule of claim 1, which encodes a polypeptide comprising an amino acid sequence having an amino acid sequence that is identical to at least about 55% of an amino acid sequence shown in SEQ ID NO:2, SEQ ID NO:4, SEQ ID NO:6, SEQ ID NO:8 or SEQ ID NO:14.

15. The nucleic acid molecule of claim 1, which encodes a polypeptide comprising an amino acid sequence having an amino acid sequence that is identical to at least about 70% of an amino acid sequence shown in SEQ ID NO:2, SEQ ID NO:4, SEQ ID NO:6, SEQ ID NO:8 or SEQ ID NO:14.

16. The nucleic acid molecule of claim 2, which comprises the coding region of the nucleotide sequence shown in SEQ ID NO:1.

17. The nucleic acid molecule of claim 3, which comprises the coding region of the nucleotide sequence shown in SEQ ID NO:3.

18. The nucleic acid molecule of claim 4, which comprises the coding region of the nucleotide sequence shown in SEQ ID NO:5.

19. The nucleic acid molecule of claim 5, which comprises the coding region of the nucleotide sequence shown in SEQ ID NO:7.

20. The nucleic acid molecule of claim 6, which comprises the coding region of the nucleotide sequence shown in SEQ ID NO:13.

21. An expression vector comprising the nucleic acid molecule of claims 2, 3, 4, 5, or 6.

22. A host cell transfected with the expression vector of claim 21.

23. An isolated MRT nucleic acid molecule comprising a nucleotide sequence encoding a polypeptide comprising:

(a) at least one transmembrane domain having an amino acid sequence that is identical to at least about 70% of an amino acid sequence shown in SEQ ID NO:2, SEQ ID NO:4, SEQ ID NO:6, or SEQ ID NO:14; and (b) at least one histidine rich domain.

24. The isolated nucleic acid molecule of claim 23, further having the ability to transport one or more of the metals selected from the group consisting of Fe(II), Cd, Co, Mn, Pb, Hg and Zn.

* * * * *

UNITED STATES PATENT AND TRADEMARK OFFICE
CERTIFICATE OF CORRECTION

PATENT NO.   : 5,846,821
DATED        : December 8, 1998
INVENTOR(S)  : Mary Lou Guerinot et al.

It is certified that error appears in the above-identified patent and that said Letters Patent is hereby corrected as shown below:

At column 1, line 9, please add the following:
-- GOVERNMENT SUPPORT

This invention was made with government support under NSF Grant Nos. IBN-9318093 and MCB-9405200. The government has certain rights in the invention.--

Signed and Sealed this

Fifteenth Day of June, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1329 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 18..1037

( x i ) SEQUENCE DESCRIPTION: SEQ ID NO:1:

```
CAAATTCAGC ACTTCTC ATG AAA ACA ATC TTC CTC GTA CTC ATT TTT GTC         50
                    Met Lys Thr Ile Phe Leu Val Leu Ile Phe Val
                     1               5                      10

TCT TTT GCA ATC TCT CCA GCA ACT TCA ACT GCG CCG GAA GAA TGT GGA         98
Ser Phe Ala Ile Ser Pro Ala Thr Ser Thr Ala Pro Glu Glu Cys Gly
            15                  20                  25

AGC GAG TCA GCG AAC CCG TGC GTC AAC AAA GCT AAA GCT TTG CCT CTC        146
Ser Glu Ser Ala Asn Pro Cys Val Asn Lys Ala Lys Ala Leu Pro Leu
        30                  35                  40

AAA GTC ATA GCA ATC TTC GTA ATC CTC ATT GCA AGC ATG ATT GGT GTT        194
Lys Val Ile Ala Ile Phe Val Ile Leu Ile Ala Ser Met Ile Gly Val
    45                  50                  55

GGA GCT CCT CTC TTT AGC CGT AAC GTT TCG TTC CTC CAA CCA GAC GGA        242
Gly Ala Pro Leu Phe Ser Arg Asn Val Ser Phe Leu Gln Pro Asp Gly
60                  65                  70                  75

AAC ATC TTC ACT ATC ATT AAG TGT TTC GCC TCC GGG ATC ATC CTT GGA        290
Asn Ile Phe Thr Ile Ile Lys Cys Phe Ala Ser Gly Ile Ile Leu Gly
        80                  85                  90

ACC GGT TTT ATG CAC GTT TTA CCT GAT TCT TTC GAA ATG TTG TCA TCT        338
Thr Gly Phe Met His Val Leu Pro Asp Ser Phe Glu Met Leu Ser Ser
        95                 100                 105

ATA TGT CTT GAA GAG AAC CCG TGG CAT AAA TTT CCT TTC TCC GGA TTT        386
Ile Cys Leu Glu Glu Asn Pro Trp His Lys Phe Pro Phe Ser Gly Phe
       110                 115                 120
```

| | | | | | | | | | | | | | | | | |
|---|---|---|---|---|---|---|---|---|---|---|---|---|---|---|---|---|
| CTC | GCT | ATG | TTA | TCG | GGT | CTA | ATC | ACT | CTA | GCC | ATT | GAC | TCC | ATG | GCC | 434 |
| Leu | Ala | Met | Leu | Ser | Gly | Leu | Ile | Thr | Leu | Ala | Ile | Asp | Ser | Met | Ala | |
| | 125 | | | | 130 | | | | | 135 | | | | | | |
| ACG | AGC | CTA | TAC | ACC | AGC | AAG | AAC | GCA | GTT | GGT | ATC | ATG | CCC | CAT | GGT | 482 |
| Thr | Ser | Leu | Tyr | Thr | Ser | Lys | Asn | Ala | Val | Gly | Ile | Met | Pro | His | Gly | |
| 140 | | | | | 145 | | | | | 150 | | | | | 155 | |
| CAT | GGT | CAT | GGT | CAC | GGC | CCC | GCA | AAT | GAT | GTT | ACC | TTA | CCA | ATA | AAA | 530 |
| His | Gly | His | Gly | His | Gly | Pro | Ala | Asn | Asp | Val | Thr | Leu | Pro | Ile | Lys | |
| | | | | 160 | | | | | 165 | | | | | 170 | | |
| GAA | GAT | GAT | TCG | TCA | AAT | GCA | CAG | CTC | TTG | CGA | TAC | CGA | GTC | ATT | GCC | 578 |
| Glu | Asp | Asp | Ser | Ser | Asn | Ala | Gln | Leu | Leu | Arg | Tyr | Arg | Val | Ile | Ala | |
| | | | 175 | | | | | 180 | | | | | 185 | | | |
| ATG | GTC | TTG | GAA | CTT | GGG | ATC | ATA | GTT | CAC | TCG | GTG | GTC | ATT | GGA | TTA | 626 |
| Met | Val | Leu | Glu | Leu | Gly | Ile | Ile | Val | His | Ser | Val | Val | Ile | Gly | Leu | |
| | | 190 | | | | | 195 | | | | | 200 | | | | |
| TCT | CTA | GGA | GCA | ACT | AGT | GAC | ACT | TGC | ACC | ATT | AAA | GGA | CTT | ATA | GCA | 674 |
| Ser | Leu | Gly | Ala | Thr | Ser | Asp | Thr | Cys | Thr | Ile | Lys | Gly | Leu | Ile | Ala | |
| | 205 | | | | | 210 | | | | | 215 | | | | | |
| GCT | CTT | TGC | TTC | CAT | CAA | ATG | TTC | GAA | GGC | ATG | GGT | CTT | GGC | GGT | TGT | 722 |
| Ala | Leu | Cys | Phe | His | Gln | Met | Phe | Glu | Gly | Met | Gly | Leu | Gly | Gly | Cys | |
| 220 | | | | | 225 | | | | | 230 | | | | | 235 | |
| ATC | CTC | CAG | GCT | GAG | TAT | ACA | AAT | ATG | AAG | AAA | TTT | GTT | ATG | GCG | TTC | 770 |
| Ile | Leu | Gln | Ala | Glu | Tyr | Thr | Asn | Met | Lys | Lys | Phe | Val | Met | Ala | Phe | |
| | | | | 240 | | | | | 245 | | | | | 250 | | |
| TTT | TTC | GCG | GTA | ACA | ACA | CCA | TTC | GGA | ATA | GCG | TTA | GGG | ATC | GCT | CTA | 818 |
| Phe | Phe | Ala | Val | Thr | Thr | Pro | Phe | Gly | Ile | Ala | Leu | Gly | Ile | Ala | Leu | |
| | | | 255 | | | | | 260 | | | | | 265 | | | |
| TCA | ACT | GTT | TAC | CAA | GAT | AAT | AGC | CCA | AAA | GCT | TTG | ATC | ACG | GTT | GGA | 866 |
| Ser | Thr | Val | Tyr | Gln | Asp | Asn | Ser | Pro | Lys | Ala | Leu | Ile | Thr | Val | Gly | |
| | | 270 | | | | | 275 | | | | | 280 | | | | |
| CTT | CTA | AAT | GCA | TGC | TCC | GCT | GGA | TTG | CTC | ATT | TAC | ATG | GCA | CTC | GTG | 914 |
| Leu | Leu | Asn | Ala | Cys | Ser | Ala | Gly | Leu | Leu | Ile | Tyr | Met | Ala | Leu | Val | |
| | 285 | | | | | 290 | | | | | 295 | | | | | |
| GAT | CTT | CTA | GCT | GCG | GAG | TTC | ATG | GGA | CCT | AAG | CTT | CAA | GGT | AGC | ATC | 962 |
| Asp | Leu | Leu | Ala | Ala | Glu | Phe | Met | Gly | Pro | Lys | Leu | Gln | Gly | Ser | Ile | |
| 300 | | | | | 305 | | | | | 310 | | | | | 315 | |
| AAA | ATG | CAG | TTC | AAG | TGT | TTA | ATC | GCG | GCT | CTT | CTC | GGG | TGC | GGT | GGA | 1010 |
| Lys | Met | Gln | Phe | Lys | Cys | Leu | Ile | Ala | Ala | Leu | Leu | Gly | Cys | Gly | Gly | |
| | | | | 320 | | | | | 325 | | | | | 330 | | |
| ATG | TCG | ATT | ATC | GCC | AAA | TGG | GCT | TAACTAATAC | | TCCAGATATT | | GCGGAATTGA | | | | 1064 |
| Met | Ser | Ile | Ile | Ala | Lys | Trp | Ala | | | | | | | | | |
| | | | 335 | | | | | 340 | | | | | | | | |
| AATCATGTGG | | ATTTCATTAT | | CGAACTAAAA | | CCGTTTTAGG | | TTTACGTCTC | | GATTCTCTAT | | | | | | 1124 |
| CGGTTTTTTA | | TCTTCTCTTA | | CAAAAGATTT | | GCGTGGATCT | | ATCACATTTT | | AAGGAACATG | | | | | | 1184 |
| TCTTTTGGTA | | GATATGTAAA | | TGTGATAGGC | | CCCACGATTC | | ATAGTTTTCT | | TTTGTATCTT | | | | | | 1244 |
| CCTTTATTTT | | GTCAAGGCAG | | TATAGTTCAT | | ATCGTGTAAT | | GTTTTTGCAT | | CTCATATAAA | | | | | | 1304 |
| TAAATAAAAC | | TTTTGCTGCT | | TTTTC | | | | | | | | | | | | 1329 |

( 2 ) INFORMATION FOR SEQ ID NO:2:

( i ) SEQUENCE CHARACTERISTICS:
        ( A ) LENGTH: 339 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met  Lys  Thr  Ile  Phe  Leu  Val  Leu  Ile  Phe  Val  Ser  Phe  Ala  Ile  Ser

```
              1                   5                       10                      15

Pro  Ala  Thr  Ser  Thr  Ala  Pro  Glu  Glu  Cys  Gly  Ser  Glu  Ser  Ala  Asn
                    20                   25                      30

Pro  Cys  Val  Asn  Lys  Ala  Lys  Ala  Leu  Pro  Leu  Lys  Val  Ile  Ala  Ile
               35                   40                   45

Phe  Val  Ile  Leu  Ile  Ala  Ser  Met  Ile  Gly  Val  Gly  Ala  Pro  Leu  Phe
          50                   55                   60

Ser  Arg  Asn  Val  Ser  Phe  Leu  Gln  Pro  Asp  Gly  Asn  Ile  Phe  Thr  Ile
65                       70                   75                            80

Ile  Lys  Cys  Phe  Ala  Ser  Gly  Ile  Ile  Leu  Gly  Thr  Gly  Phe  Met  His
                    85                   90                        95

Val  Leu  Pro  Asp  Ser  Phe  Glu  Met  Leu  Ser  Ser  Ile  Cys  Leu  Glu  Glu
               100                  105                      110

Asn  Pro  Trp  His  Lys  Phe  Pro  Phe  Ser  Gly  Phe  Leu  Ala  Met  Leu  Ser
               115                  120                      125

Gly  Leu  Ile  Thr  Leu  Ala  Ile  Asp  Ser  Met  Ala  Thr  Ser  Leu  Tyr  Thr
          130                  135                  140

Ser  Lys  Asn  Ala  Val  Gly  Ile  Met  Pro  His  Gly  His  Gly  His  Gly  His
145                      150                  155                           160

Gly  Pro  Ala  Asn  Asp  Val  Thr  Leu  Pro  Ile  Lys  Glu  Asp  Asp  Ser  Ser
                    165                  170                      175

Asn  Ala  Gln  Leu  Leu  Arg  Tyr  Arg  Val  Ile  Ala  Met  Val  Leu  Glu  Leu
               180                  185                      190

Gly  Ile  Ile  Val  His  Ser  Val  Val  Ile  Gly  Leu  Ser  Leu  Gly  Ala  Thr
          195                  200                  205

Ser  Asp  Thr  Cys  Thr  Ile  Lys  Gly  Leu  Ile  Ala  Ala  Leu  Cys  Phe  His
210                      215                  220

Gln  Met  Phe  Glu  Gly  Met  Gly  Leu  Gly  Gly  Cys  Ile  Leu  Gln  Ala  Glu
225                      230                  235                           240

Tyr  Thr  Asn  Met  Lys  Lys  Phe  Val  Met  Ala  Phe  Phe  Phe  Ala  Val  Thr
                    245                  250                       255

Thr  Pro  Phe  Gly  Ile  Ala  Leu  Gly  Ile  Ala  Leu  Ser  Thr  Val  Tyr  Gln
               260                  265                       270

Asp  Asn  Ser  Pro  Lys  Ala  Leu  Ile  Thr  Val  Gly  Leu  Leu  Asn  Ala  Cys
          275                  280                       285

Ser  Ala  Gly  Leu  Leu  Ile  Tyr  Met  Ala  Leu  Val  Asp  Leu  Leu  Ala  Ala
290                      295                       300

Glu  Phe  Met  Gly  Pro  Lys  Leu  Gln  Gly  Ser  Ile  Lys  Met  Gln  Phe  Lys
305                      310                       315                      320

Cys  Leu  Ile  Ala  Ala  Leu  Leu  Gly  Cys  Gly  Gly  Met  Ser  Ile  Ile  Ala
               325                   330                       335

Lys  Trp  Ala
```

( 2 ) INFORMATION FOR SEQ ID NO:3:

( i ) SEQUENCE CHARACTERISTICS:
        ( A ) LENGTH: 1215 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 42..1106

( x i ) SEQUENCE DESCRIPTION: SEQ ID NO:3:

```
CAGTGTGAGT AATTTAGCAA GAACATAAAT ATCTTAAACT C ATG TCT GAA TGT                                              53
                                               Met Ser Glu Cys
                                                1

GGA TGT TTT TCG GCA ACA ACT ATG TTG AGA ATT TGT GTA GTA TTG ATA                                           101
Gly Cys Phe Ser Ala Thr Thr Met Leu Arg Ile Cys Val Val Leu Ile
     5              10              15              20

ATA TGT TTG CAT ATG TGT TGT GCC TCG AGT GAT TGT ACA AGT CAC GAT                                           149
Ile Cys Leu His Met Cys Cys Ala Ser Ser Asp Cys Thr Ser His Asp
             25              30              35

GAT CCT GTG TCT CAA GAC GAA GCA GAG AAA GCG ACG AAG CTA AAG CTT                                           197
Asp Pro Val Ser Gln Asp Glu Ala Glu Lys Ala Thr Lys Leu Lys Leu
         40              45              50

GGT TCG ATA GCT TTA CTT CTT GTA GCC GGA GGA GTC GGC GTG AGT CTA                                           245
Gly Ser Ile Ala Leu Leu Leu Val Ala Gly Gly Val Gly Val Ser Leu
             55              60              65

CCG TTG ATC GGG AAA AGG ATT CCG GCG TTA CAA CCG GAA AAT GAT ATC                                           293
Pro Leu Ile Gly Lys Arg Ile Pro Ala Leu Gln Pro Glu Asn Asp Ile
         70              75              80

TTC TTC ATG GTG AAA GCT TTT GCT GCA GGA GTG ATC CTC TGC ACA GGT                                           341
Phe Phe Met Val Lys Ala Phe Ala Ala Gly Val Ile Leu Cys Thr Gly
 85              90              95              100

TTC GTT CAT ATC TTA CCA GAC GCG TTC GAG AGA TTG AGC TCT CCA TGT                                           389
Phe Val His Ile Leu Pro Asp Ala Phe Glu Arg Leu Ser Ser Pro Cys
             105             110             115

CTT GAG GAC ACT ACA GCT GGG AAG TTC CCG TTT GCT GGT TTT GTA GCG                                           437
Leu Glu Asp Thr Thr Ala Gly Lys Phe Pro Phe Ala Gly Phe Val Ala
         120             125             130

ATG CTG TCG GCG ATG GGG ACT CTT ATG ATC GAC ACA TTC GCG ACA GGG                                           485
Met Leu Ser Ala Met Gly Thr Leu Met Ile Asp Thr Phe Ala Thr Gly
             135             140             145

TAT TAC AAG AGG CAA CAT TTT AGC AAT AAC CAT GGG AGC AAG CAA GTG                                           533
Tyr Tyr Lys Arg Gln His Phe Ser Asn Asn His Gly Ser Lys Gln Val
     150             155             160

AAC GTA GTA GTA GAT GAA GAA GAG CAT GCG GGT CAT GTT CAC ATT CAC                                           581
Asn Val Val Val Asp Glu Glu Glu His Ala Gly His Val His Ile His
165             170             175             180

ACG CAC GCT AGT CAC GGA CAC ACA CAT GGT TCG ACC GAG TTG ATC AGA                                           629
Thr His Ala Ser His Gly His Thr His Gly Ser Thr Glu Leu Ile Arg
             185             190             195

AGA CGT ATA GTG TCG CAG GTG CTT GAG ATT GGG ATA GTT GTG CAT TCG                                           677
Arg Arg Ile Val Ser Gln Val Leu Glu Ile Gly Ile Val Val His Ser
         200             205             210

GTT ATT ATA GGG ATA TCA CTT GGA GCT TCA CAG AGC ATA GAC ACC ATA                                           725
Val Ile Ile Gly Ile Ser Leu Gly Ala Ser Gln Ser Ile Asp Thr Ile
             215             220             225

AAG CCA CTC ATG GCT GCA CTA TCT TTC CAT CAG TTC TTT GAA GGT CTT                                           773
Lys Pro Leu Met Ala Ala Leu Ser Phe His Gln Phe Phe Glu Gly Leu
         230             235             240

GGC CTC GGT GGA TGC ATC TCC CTG GCG GAT ATG AAG TCG AAA TCG ACA                                           821
Gly Leu Gly Gly Cys Ile Ser Leu Ala Asp Met Lys Ser Lys Ser Thr
245             250             255             260

GTG CTA ATG GCG ACA TTT TTC TCG GTG ACG GCG CCA CTT GGG ATA GGA                                           869
Val Leu Met Ala Thr Phe Phe Ser Val Thr Ala Pro Leu Gly Ile Gly
             265             270             275

ATA GGG TTG GGG ATG TCA AGT GGT TTA GGC TAC AGG AAA GAG AGC AAA                                           917
Ile Gly Leu Gly Met Ser Ser Gly Leu Gly Tyr Arg Lys Glu Ser Lys
         280             285             290

GAG GCA ATA ATG GTG GAA GGA ATG TTG AAT GCT GCA TCT GCT GGG ATA                                           965
Glu Ala Ile Met Val Glu Gly Met Leu Asn Ala Ala Ser Ala Gly Ile
     295             300             305
```

```
CTC ATA TAC ATG TCA CTT GTT GAT CTT CTT GCT ACT GAT TTT ATG AAT      1013
Leu Ile Tyr Met Ser Leu Val Asp Leu Leu Ala Thr Asp Phe Met Asn
310                 315                 320

CCA AGA TTG CAA TCC AAT CTC TGG CTT CAC TTG GCT GCT TAT CTC TCT      1061
Pro Arg Leu Gln Ser Asn Leu Trp Leu His Leu Ala Ala Tyr Leu Ser
325                 330                 335                 340

CTC GTC CTA GGC GCA GGT TCC ATG TCT CTC CTC GCC ATC TGG GCC          1106
Leu Val Leu Gly Ala Gly Ser Met Ser Leu Leu Ala Ile Trp Ala
                345                 350                 355

TGATTCTTGA TCTGAAACTA ACAAACAAAC AAACCAAATG CCGCTCTTTT TTCTCAAATC    1166

TGTAATGGTG TTTCTAATCT CAGAATCAAT ACTATTCTAT CTTGAACAC                1215
```

(2) INFORMATION FOR SEQ ID NO:4:

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Glu Cys Gly Cys Phe Ser Ala Thr Thr Met Leu Arg Ile Cys
 1               5                  10                  15

Val Val Leu Ile Ile Cys Leu His Met Cys Cys Ala Ser Ser Asp Cys
                20                  25                  30

Thr Ser His Asp Asp Pro Val Ser Gln Asp Glu Ala Glu Lys Ala Thr
            35                  40                  45

Lys Leu Lys Leu Gly Ser Ile Ala Leu Leu Leu Val Ala Gly Gly Val
        50                  55                  60

Gly Val Ser Leu Pro Leu Ile Gly Lys Arg Ile Pro Ala Leu Gln Pro
65                  70                  75                  80

Glu Asn Asp Ile Phe Phe Met Val Lys Ala Phe Ala Ala Gly Val Ile
                85                  90                  95

Leu Cys Thr Gly Phe Val His Ile Leu Pro Asp Ala Phe Glu Arg Leu
                100                 105                 110

Ser Ser Pro Cys Leu Glu Asp Thr Thr Ala Gly Lys Phe Pro Phe Ala
            115                 120                 125

Gly Phe Val Ala Met Leu Ser Ala Met Gly Thr Leu Met Ile Asp Thr
130                 135                 140

Phe Ala Thr Gly Tyr Tyr Lys Arg Gln His Phe Ser Asn Asn His Gly
145                 150                 155                 160

Ser Lys Gln Val Asn Val Val Val Asp Glu Glu His Ala Gly His
            165                 170                 175

Val His Ile His Thr His Ala Ser His Gly His Thr His Gly Ser Thr
                180                 185                 190

Glu Leu Ile Arg Arg Arg Ile Val Ser Gln Val Leu Glu Ile Gly Ile
            195                 200                 205

Val Val His Ser Val Ile Ile Gly Ile Ser Leu Gly Ala Ser Gln Ser
            210                 215                 220

Ile Asp Thr Ile Lys Pro Leu Met Ala Ala Leu Ser Phe His Gln Phe
225                 230                 235                 240

Phe Glu Gly Leu Gly Leu Gly Gly Cys Ile Ser Leu Ala Asp Met Lys
                245                 250                 255

Ser Lys Ser Thr Val Leu Met Ala Thr Phe Phe Ser Val Thr Ala Pro
            260                 265                 270
```

| | | | | | | | | | | | | | | |
|---|---|---|---|---|---|---|---|---|---|---|---|---|---|---|
| Leu | Gly | Ile | Gly | Ile | Gly | Leu | Gly | Met | Ser | Ser | Gly | Leu | Gly | Tyr | Arg |
| | | 275 | | | | | 280 | | | | | 285 | | | |
| Lys | Glu | Ser | Lys | Glu | Ala | Ile | Met | Val | Glu | Gly | Met | Leu | Asn | Ala | Ala |
| | | 290 | | | | | 295 | | | | | 300 | | | |
| Ser | Ala | Gly | Ile | Leu | Ile | Tyr | Met | Ser | Leu | Val | Asp | Leu | Leu | Ala | Thr |
| 305 | | | | | 310 | | | | | 315 | | | | | 320 |
| Asp | Phe | Met | Asn | Pro | Arg | Leu | Gln | Ser | Asn | Leu | Trp | Leu | His | Leu | Ala |
| | | | | 325 | | | | | 330 | | | | | 335 | |
| Ala | Tyr | Leu | Ser | Leu | Val | Leu | Gly | Ala | Gly | Ser | Met | Ser | Leu | Leu | Ala |
| | | | 340 | | | | | 345 | | | | | 350 | | |
| Ile | Trp | Ala | | | | | | | | | | | | | |
| | | 355 | | | | | | | | | | | | | |

( 2 ) INFORMATION FOR SEQ ID NO:5:

( i ) SEQUENCE CHARACTERISTICS:
        ( A ) LENGTH: 1061 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1059

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GCT | TTG | TCT | TCC | AAA | ACC | CTA | AAG | TCA | ACT | CTC | GTC | TTC | CTC | TCT | 48 |
| Met | Ala | Leu | Ser | Ser | Lys | Thr | Leu | Lys | Ser | Thr | Leu | Val | Phe | Leu | Ser | |
| 1 | | | | 5 | | | | | 10 | | | | | 15 | | |
| ATT | ATT | TTC | CTC | TGT | TTC | TCC | TTG | ATC | CTA | GCT | CAC | GGC | GGC | ATA | GAC | 96 |
| Ile | Ile | Phe | Leu | Cys | Phe | Ser | Leu | Ile | Leu | Ala | His | Gly | Gly | Ile | Asp | |
| | | | 20 | | | | | 25 | | | | | 30 | | | |
| GAC | GGC | GAC | GAA | GAA | GAG | GAG | ACC | AAC | CAG | CCA | CCT | CCG | GCC | ACC | GGA | 144 |
| Asp | Gly | Asp | Glu | Glu | Glu | Glu | Thr | Asn | Gln | Pro | Pro | Pro | Ala | Thr | Gly | |
| | 35 | | | | | 40 | | | | | 45 | | | | | |
| ACA | ACC | ACC | GTC | GTG | AAT | CTC | CGA | TCC | AAA | GGC | TTG | GTG | CTT | GTG | AAG | 192 |
| Thr | Thr | Thr | Val | Val | Asn | Leu | Arg | Ser | Lys | Gly | Leu | Val | Leu | Val | Lys | |
| | 50 | | | | | 55 | | | | | 60 | | | | | |
| ATC | TAC | TGT | ATT | ATA | ATA | CTC | TTC | TTT | AGC | ACA | TTC | TTA | GCC | GGA | ATT | 240 |
| Ile | Tyr | Cys | Ile | Ile | Ile | Leu | Phe | Phe | Ser | Thr | Phe | Leu | Ala | Gly | Ile | |
| 65 | | | | | 70 | | | | | 75 | | | | | 80 | |
| TCA | CCT | TAC | TTT | TAC | CGA | TGG | AAC | GAG | TCG | TTT | CTC | CTC | CTA | GGA | ACT | 288 |
| Ser | Pro | Tyr | Phe | Tyr | Arg | Trp | Asn | Glu | Ser | Phe | Leu | Leu | Leu | Gly | Thr | |
| | | | | 85 | | | | | 90 | | | | | 95 | | |
| CAA | TTC | TCC | GGT | GGT | ATA | TTC | CTC | GCG | ACC | GCT | CTA | ATC | CAT | TTC | CTC | 336 |
| Gln | Phe | Ser | Gly | Gly | Ile | Phe | Leu | Ala | Thr | Ala | Leu | Ile | His | Phe | Leu | |
| | | | 100 | | | | | 105 | | | | | 110 | | | |
| AGC | GAC | GCT | AAC | GAG | ACT | TTC | CGA | GGG | TTA | AAA | CAC | AAA | GAG | TAT | CCT | 384 |
| Ser | Asp | Ala | Asn | Glu | Thr | Phe | Arg | Gly | Leu | Lys | His | Lys | Glu | Tyr | Pro | |
| | | 115 | | | | | 120 | | | | | 125 | | | | |
| TAC | GCT | TTC | ATG | TTA | GCA | GCC | GCT | GGA | TAT | TGC | CTT | ACA | ATG | CTG | GCA | 432 |
| Tyr | Ala | Phe | Met | Leu | Ala | Ala | Ala | Gly | Tyr | Cys | Leu | Thr | Met | Leu | Ala | |
| | | 130 | | | | | 135 | | | | | 140 | | | | |
| GAT | GTG | GCG | GTT | GCG | TTT | GTA | GCG | GCT | GGG | AGT | AAT | AAC | AAC | CAC | GTC | 480 |
| Asp | Val | Ala | Val | Ala | Phe | Val | Ala | Ala | Gly | Ser | Asn | Asn | Asn | His | Val | |
| 145 | | | | | 150 | | | | | 155 | | | | | 160 | |
| GGA | GCT | AGC | GTC | GGA | GAG | TCG | AGG | GAG | GAT | GAT | GAC | GTG | GCA | GTG | AAA | 528 |
| Gly | Ala | Ser | Val | Gly | Glu | Ser | Arg | Glu | Asp | Asp | Asp | Val | Ala | Val | Lys | |
| | | | | 165 | | | | | 170 | | | | | 175 | | |
| GAG | GAA | GGA | CGT | CGT | GAG | ATA | AAG | AGT | GGT | GTT | GAT | GTG | AGT | CAA | GCG | 576 |

```
Glu  Glu  Gly  Arg  Arg  Glu  Ile  Lys  Ser  Gly  Val  Asp  Val  Ser  Gln  Ala
              180                      185                      190

CTT  ATA  CGA  ACT  AGT  GGA  TTT  GGA  GAC  ACA  GCT  TTG  CTG  ATT  TTT  GCT        624
Leu  Ile  Arg  Thr  Ser  Gly  Phe  Gly  Asp  Thr  Ala  Leu  Leu  Ile  Phe  Ala
          195                      200                      205

CTT  TGT  TTT  CAC  TCC  ATC  TTT  GAG  GGA  ATC  GCC  ATT  GGT  CTC  TCA  GAC        672
Leu  Cys  Phe  His  Ser  Ile  Phe  Glu  Gly  Ile  Ala  Ile  Gly  Leu  Ser  Asp
     210                      215                      220

ACT  AAA  AGC  GAC  GCT  TGG  AGA  AAC  CTA  TGG  ACA  ATA  TCG  TTG  CAC  AAG        720
Thr  Lys  Ser  Asp  Ala  Trp  Arg  Asn  Leu  Trp  Thr  Ile  Ser  Leu  His  Lys
225                      230                      235                      240

GTC  TTT  GCG  GCC  GTA  GCA  ATG  GGA  ATA  GCT  CTT  CTC  AAG  CTA  ATC  CCT        768
Val  Phe  Ala  Ala  Val  Ala  Met  Gly  Ile  Ala  Leu  Leu  Lys  Leu  Ile  Pro
               245                      250                      255

AAA  CGT  CCA  TTC  TTC  CTC  ACT  GTC  GTC  TAC  TCC  TTC  GCC  TTT  GGG  ATA        816
Lys  Arg  Pro  Phe  Phe  Leu  Thr  Val  Val  Tyr  Ser  Phe  Ala  Phe  Gly  Ile
               260                      265                      270

TCG  AGT  CCC  ATA  GGT  GTC  GGG  ATT  GGC  ATT  GGA  ATC  AAT  GCC  ACT  AGC        864
Ser  Ser  Pro  Ile  Gly  Val  Gly  Ile  Gly  Ile  Gly  Ile  Asn  Ala  Thr  Ser
          275                      280                      285

CAA  GGA  GCT  GGT  GGT  GAC  TGG  ACC  TAC  GCG  ATC  TCT  ATG  GGG  CTT  GCG        912
Gln  Gly  Ala  Gly  Gly  Asp  Trp  Thr  Tyr  Ala  Ile  Ser  Met  Gly  Leu  Ala
     290                      295                      300

TGT  GGA  GTT  TTT  GTG  TAC  GTT  GCG  GTT  AAC  CAT  CTC  ATC  TCA  AAA  GGG        960
Cys  Gly  Val  Phe  Val  Tyr  Val  Ala  Val  Asn  His  Leu  Ile  Ser  Lys  Gly
305                      310                      315                      320

TAT  AAG  CCT  CTT  GAG  GAA  TGT  TAC  TTC  GAC  AAG  CCA  ATC  TAC  AAG  TTT       1008
Tyr  Lys  Pro  Leu  Glu  Glu  Cys  Tyr  Phe  Asp  Lys  Pro  Ile  Tyr  Lys  Phe
               325                      330                      335

ATT  GCC  GTC  TTC  CTC  GGT  GTT  GCT  TTG  CTC  TCT  GTT  GTA  ATG  ATT  TGG       1056
Ile  Ala  Val  Phe  Leu  Gly  Val  Ala  Leu  Leu  Ser  Val  Val  Met  Ile  Trp
               340                      345                      350

GAT  TG                                                                              1061
Asp
```

( 2 ) INFORMATION FOR SEQ ID NO:6:

( i ) SEQUENCE CHARACTERISTICS:
    ( A ) LENGTH: 353 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met  Ala  Leu  Ser  Ser  Lys  Thr  Leu  Lys  Ser  Thr  Leu  Val  Phe  Leu  Ser
 1                  5                       10                       15

Ile  Ile  Phe  Leu  Cys  Phe  Ser  Leu  Ile  Leu  Ala  His  Gly  Gly  Ile  Asp
               20                       25                       30

Asp  Gly  Asp  Glu  Glu  Glu  Glu  Thr  Asn  Gln  Pro  Pro  Ala  Thr  Gly
          35                       40                       45

Thr  Thr  Thr  Val  Val  Asn  Leu  Arg  Ser  Lys  Gly  Leu  Val  Leu  Val  Lys
     50                       55                       60

Ile  Tyr  Cys  Ile  Ile  Ile  Leu  Phe  Phe  Ser  Thr  Phe  Leu  Ala  Gly  Ile
65             70                       75                       80

Ser  Pro  Tyr  Phe  Tyr  Arg  Trp  Asn  Glu  Ser  Phe  Leu  Leu  Leu  Gly  Thr
               85                       90                       95

Gln  Phe  Ser  Gly  Gly  Ile  Phe  Leu  Ala  Thr  Ala  Leu  Ile  His  Phe  Leu
               100                      105                      110

Ser  Asp  Ala  Asn  Glu  Thr  Phe  Arg  Gly  Leu  Lys  His  Lys  Glu  Tyr  Pro
```

```
                               115                         120                          125
Tyr  Ala  Phe  Met  Leu  Ala  Ala  Ala  Gly  Tyr  Cys  Leu  Thr  Met  Leu  Ala
     130                      135                      140

Asp  Val  Ala  Val  Ala  Phe  Val  Ala  Ala  Gly  Ser  Asn  Asn  Asn  His  Val
145                      150                      155                      160

Gly  Ala  Ser  Val  Gly  Glu  Ser  Arg  Glu  Asp  Asp  Val  Ala  Val  Lys
                    165                      170                      175

Glu  Glu  Gly  Arg  Arg  Glu  Ile  Lys  Ser  Gly  Val  Asp  Val  Ser  Gln  Ala
               180                      185                      190

Leu  Ile  Arg  Thr  Ser  Gly  Phe  Gly  Asp  Thr  Ala  Leu  Leu  Ile  Phe  Ala
          195                      200                      205

Leu  Cys  Phe  His  Ser  Ile  Phe  Glu  Gly  Ile  Ala  Ile  Gly  Leu  Ser  Asp
     210                      215                      220

Thr  Lys  Ser  Asp  Ala  Trp  Arg  Asn  Leu  Trp  Thr  Ile  Ser  Leu  His  Lys
225                      230                      235                      240

Val  Phe  Ala  Ala  Val  Ala  Met  Gly  Ile  Ala  Leu  Leu  Lys  Leu  Ile  Pro
                    245                      250                      255

Lys  Arg  Pro  Phe  Phe  Leu  Thr  Val  Val  Tyr  Ser  Phe  Ala  Phe  Gly  Ile
               260                      265                      270

Ser  Ser  Pro  Ile  Gly  Val  Gly  Ile  Gly  Ile  Gly  Ile  Asn  Ala  Thr  Ser
          275                      280                      285

Gln  Gly  Ala  Gly  Gly  Asp  Trp  Thr  Tyr  Ala  Ile  Ser  Met  Gly  Leu  Ala
     290                      295                      300

Cys  Gly  Val  Phe  Val  Tyr  Val  Ala  Val  Asn  His  Leu  Ile  Ser  Lys  Gly
305                      310                      315                      320

Tyr  Lys  Pro  Leu  Glu  Glu  Cys  Tyr  Phe  Asp  Lys  Pro  Ile  Tyr  Lys  Phe
                    325                      330                      335

Ile  Ala  Val  Phe  Leu  Gly  Val  Ala  Leu  Leu  Ser  Val  Val  Met  Ile  Trp
               340                      345                      350

Asp
```

( 2 ) INFORMATION FOR SEQ ID NO:7:

( i ) SEQUENCE CHARACTERISTICS:
    ( A ) LENGTH: 1374 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 48..1064

( x i ) SEQUENCE DESCRIPTION: SEQ ID NO:7:

```
GTGTGAGTAA  TTTAGAAAAG  CCCTAATTTT  AAAATAAGAT  AGAGATT  ATG  AAG  ACT        56
                                                         Met  Lys  Thr
                                                          1

AAG  AGC  GTG  AAA  CTC  TTA  TTC  TTC  TTC  TTC  TCC  GTC  TCC  CTC  CTT  CTC    104
Lys  Ser  Val  Lys  Leu  Leu  Phe  Phe  Phe  Phe  Ser  Val  Ser  Leu  Leu  Leu
      5                        10                      15

ATC  GCC  GTC  GTC  AAC  GCC  GCC  GAA  GGC  CAT  TCA  CAT  GGT  GGA  CCA  AAA    152
Ile  Ala  Val  Val  Asn  Ala  Ala  Glu  Gly  His  Ser  His  Gly  Gly  Pro  Lys
 20                       25                      30                       35

TGT  GAA  TGC  TCA  CAC  GAA  GAC  GAC  CAT  GAA  AAC  AAA  GCC  GGA  GCT  CGG    200
Cys  Glu  Cys  Ser  His  Glu  Asp  Asp  His  Glu  Asn  Lys  Ala  Gly  Ala  Arg
                    40                      45                      50

AAA  TAC  AAG  ATC  GCC  GCA  ATT  CCT  ACA  GTT  CTA  ATA  GCC  GGC  ATA  ATC    248
```

```
Lys Tyr Lys Ile Ala Ala Ile Pro Thr Val Leu Ile Ala Gly Ile Ile
             55                  60                  65

GGA GTT CTT TTC CCT TTG TTA GGC AAA GTC TTC CCT TCT TTG CGT CCA        296
Gly Val Leu Phe Pro Leu Leu Gly Lys Val Phe Pro Ser Leu Arg Pro
             70                  75                  80

GAA ACA TGT TTC TTC TTC GTC ACG AAA GCT TTC GCA GCC GGA GTT ATC        344
Glu Thr Cys Phe Phe Phe Val Thr Lys Ala Phe Ala Ala Gly Val Ile
             85                  90                  95

TTG GCT ACC GGA TTT ATG CAT GTC TTG CCT GAG GCT TAC GAG ATG CTT        392
Leu Ala Thr Gly Phe Met His Val Leu Pro Glu Ala Tyr Glu Met Leu
100                 105                 110                 115

AAC TCT CCA TGT TTG ATA TCT GAA GCA TGG GAA TTT CCG TTC ACC GGA        440
Asn Ser Pro Cys Leu Ile Ser Glu Ala Trp Glu Phe Pro Phe Thr Gly
             120                 125                 130

TTT ATT GCG ATG ATT GCT GCG ATC TTG ACG TTA TCC GTT GAT ACA TTT        488
Phe Ile Ala Met Ile Ala Ala Ile Leu Thr Leu Ser Val Asp Thr Phe
             135                 140                 145

GCC ACT TCG AGT TTC TAT AAA TCG CAT TGC AAA GCG TCT AAG AGG GTC        536
Ala Thr Ser Ser Phe Tyr Lys Ser His Cys Lys Ala Ser Lys Arg Val
             150                 155                 160

AGT GAT GGA GAA ACC GGC GAG TCC TCC GTT GAC TCC GAG AAG GTC CAA        584
Ser Asp Gly Glu Thr Gly Glu Ser Ser Val Asp Ser Glu Lys Val Gln
    165                 170                 175

ATT CTC CGG ACT AGA GTT ATT GCA CAG GTA TTG GAG TTG GGA ATA ATA        632
Ile Leu Arg Thr Arg Val Ile Ala Gln Val Leu Glu Leu Gly Ile Ile
180                 185                 190                 195

GTA CAC TCA GTG GTA ATA GGA ATA TCA CTA GGA GCT TCA CAG AGC CCA        680
Val His Ser Val Val Ile Gly Ile Ser Leu Gly Ala Ser Gln Ser Pro
             200                 205                 210

GAT GCT GCA AAA GCT CTG TTT ATT GCC TTA ATG TTT CAT CAA TGC TTC        728
Asp Ala Ala Lys Ala Leu Phe Ile Ala Leu Met Phe His Gln Cys Phe
             215                 220                 225

GAA GGT CTA GGC CTT GGT GGT TGT ATT GCT CAG GGA AAA TTC AAG TGT        776
Glu Gly Leu Gly Leu Gly Gly Cys Ile Ala Gln Gly Lys Phe Lys Cys
             230                 235                 240

TTG TCA GTA ACA ATC ATG TCG ACG TTC TTC GCA ATA ACG ACA CCG ATA        824
Leu Ser Val Thr Ile Met Ser Thr Phe Phe Ala Ile Thr Thr Pro Ile
             245                 250                 255

GGA ATC GTT GTG GGA ATG GGA ATA GCA AAT TCT TAC GAT GAG TCT TCA        872
Gly Ile Val Val Gly Met Gly Ile Ala Asn Ser Tyr Asp Glu Ser Ser
260                 265                 270                 275

CCA ACG GCT CTG ATC GTT CAA GGA GTT TTG AAC GCT GCA TCC GCA GGC        920
Pro Thr Ala Leu Ile Val Gln Gly Val Leu Asn Ala Ala Ser Ala Gly
             280                 285                 290

ATT CTC ATC TAC ATG TCT TTG GTT GAC CTT CTC GCA GCA GAT TTC ACG        968
Ile Leu Ile Tyr Met Ser Leu Val Asp Leu Leu Ala Ala Asp Phe Thr
             295                 300                 305

CAC CCT AAA ATG CAA TCC AAT ACT GGG CTT CAA ATT ATG GCC CAT ATT        1016
His Pro Lys Met Gln Ser Asn Thr Gly Leu Gln Ile Met Ala His Ile
             310                 315                 320

GCT CTC CTT CTT GGT GCT GGC CTC ATG TCT CTA TTG GCT AAA TGG GCT        1064
Ala Leu Leu Leu Gly Ala Gly Leu Met Ser Leu Leu Ala Lys Trp Ala
             325                 330                 335

TGATAGCTCC TTAATTCAAC TCTTCTAGTT TTTGCTCATG GCCTTTATG GCCACCTTGA      1124

ATTCGAATTA TTTGTTCTTA TTTTCCCCCT TTTCAATGAT ATTTTTGAGA TCTCTATTTT     1184

CTGAAACACT TCATGTACTC ATGTTTAACA TTATTACAAT TGTGTATATT GATCAGTGTC     1244

CAAGGAAAAA AAAAAAAAAA AAAAAAAAAA AAAAAAACT AAATTACTCA CACTGGCGGC      1304

CGCCACCGCG GTGGAGCTCC AGCTTTTGTT CCCTTTAGTG AGGGTTAATT TCGAGCTTGG     1364
```

CGTAATCATA 1374

( 2 ) INFORMATION FOR SEQ ID NO:8:

( i ) SEQUENCE CHARACTERISTICS:
        ( A ) LENGTH: 339 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Lys Thr Lys Ser Val Lys Leu Leu Phe Phe Phe Ser Val Ser
 1               5                  10                 15

Leu Leu Leu Ile Ala Val Val Asn Ala Ala Glu Gly His Ser His Gly
            20                  25                  30

Gly Pro Lys Cys Glu Cys Ser His Glu Asp Asp His Glu Asn Lys Ala
            35                  40                  45

Gly Ala Arg Lys Tyr Lys Ile Ala Ala Ile Pro Thr Val Leu Ile Ala
        50                  55                  60

Gly Ile Ile Gly Val Leu Phe Pro Leu Leu Gly Lys Val Phe Pro Ser
65                      70                  75                  80

Leu Arg Pro Glu Thr Cys Phe Phe Val Thr Lys Ala Phe Ala Ala
                    85                  90                  95

Gly Val Ile Leu Ala Thr Gly Phe Met His Val Leu Pro Glu Ala Tyr
                100                 105                 110

Glu Met Leu Asn Ser Pro Cys Leu Ile Ser Glu Ala Trp Glu Phe Pro
            115                 120                 125

Phe Thr Gly Phe Ile Ala Met Ile Ala Ala Ile Leu Thr Leu Ser Val
        130                 135                 140

Asp Thr Phe Ala Thr Ser Ser Phe Tyr Lys Ser His Cys Lys Ala Ser
145                 150                 155                 160

Lys Arg Val Ser Asp Gly Glu Thr Gly Glu Ser Ser Val Asp Ser Glu
                165                 170                 175

Lys Val Gln Ile Leu Arg Thr Arg Val Ile Ala Gln Val Leu Glu Leu
            180                 185                 190

Gly Ile Ile Val His Ser Val Val Ile Gly Ile Ser Leu Gly Ala Ser
        195                 200                 205

Gln Ser Pro Asp Ala Ala Lys Ala Leu Phe Ile Ala Leu Met Phe His
    210                 215                 220

Gln Cys Phe Glu Gly Leu Gly Leu Gly Gly Cys Ile Ala Gln Gly Lys
225                 230                 235                 240

Phe Lys Cys Leu Ser Val Thr Ile Met Ser Thr Phe Phe Ala Ile Thr
                245                 250                 255

Thr Pro Ile Gly Ile Val Val Gly Met Gly Ile Ala Asn Ser Tyr Asp
            260                 265                 270

Glu Ser Ser Pro Thr Ala Leu Ile Val Gln Gly Val Leu Asn Ala Ala
        275                 280                 285

Ser Ala Gly Ile Leu Ile Tyr Met Ser Leu Val Asp Leu Leu Ala Ala
    290                 295                 300

Asp Phe Thr His Pro Lys Met Gln Ser Asn Thr Gly Leu Gln Ile Met
305                 310                 315                 320

Ala His Ile Ala Leu Leu Leu Gly Ala Gly Leu Met Ser Leu Leu Ala
                325                 330                 335

Lys Trp Ala
```

( 2 ) INFORMATION FOR SEQ ID NO:9:

( i ) SEQUENCE CHARACTERISTICS:
        ( A ) LENGTH: 1131 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1129

( x i ) SEQUENCE DESCRIPTION: SEQ ID NO:9:

```
ATG  AGC  AAC  GTT  ACT  ACG  CCG  TGG  TGG  AAA  CAA  TGG  GAC  CCT  TCT  GAA        48
Met  Ser  Asn  Val  Thr  Thr  Pro  Trp  Trp  Lys  Gln  Trp  Asp  Pro  Ser  Glu
 1              5                   10                  15

GTT  ACA  CTT  GCC  GAT  AAA  ACC  CCT  GAT  GAT  GTG  TGG  AAG  ACC  TGT  GTT        96
Val  Thr  Leu  Ala  Asp  Lys  Thr  Pro  Asp  Asp  Val  Trp  Lys  Thr  Cys  Val
             20                   25                   30

TTG  CAA  GGT  GTT  TAC  TTT  GGT  GGA  AAC  GAG  TAC  AAT  GGT  AAC  TTA  GGT       144
Leu  Gln  Gly  Val  Tyr  Phe  Gly  Gly  Asn  Glu  Tyr  Asn  Gly  Asn  Leu  Gly
         35                   40                   45

GCC  AGA  ATA  TCT  TCC  GTC  TTT  GTT  ATT  CTT  TTC  GTG  AGT  ACT  TTT  TTC       192
Ala  Arg  Ile  Ser  Ser  Val  Phe  Val  Ile  Leu  Phe  Val  Ser  Thr  Phe  Phe
     50                   55                   60

ACC  ATG  TTC  CCA  TTA  ATC  TCA  ACA  AAA  GTG  AAA  AGA  TTG  AGA  ATT  CCT       240
Thr  Met  Phe  Pro  Leu  Ile  Ser  Thr  Lys  Val  Lys  Arg  Leu  Arg  Ile  Pro
 65                   70                   75                   80

CTA  TAT  GTT  TAC  CTT  TTC  GCA  AAG  TAT  TTT  GGT  TCC  GGT  GTT  ATT  GTT       288
Leu  Tyr  Val  Tyr  Leu  Phe  Ala  Lys  Tyr  Phe  Gly  Ser  Gly  Val  Ile  Val
             85                   90                   95

GCA  ACC  GCA  TTT  ATC  CAC  TTA  ATG  GAC  CCT  GCT  TAT  GGT  GCG  ATT  GGT       336
Ala  Thr  Ala  Phe  Ile  His  Leu  Met  Asp  Pro  Ala  Tyr  Gly  Ala  Ile  Gly
                 100                  105                  110

GGT  ACC  ACT  TGT  GTA  GGA  CAA  ACC  GGT  AAC  TGG  GGT  CTT  TAT  TCA  TGG       384
Gly  Thr  Thr  Cys  Val  Gly  Gln  Thr  Gly  Asn  Trp  Gly  Leu  Tyr  Ser  Trp
         115                  120                  125

TGT  CCT  GCC  ATT  ATG  CTA  ACG  AGT  TTG  ACC  TTC  ACT  TTC  CTT  ACT  GAT       432
Cys  Pro  Ala  Ile  Met  Leu  Thr  Ser  Leu  Thr  Phe  Thr  Phe  Leu  Thr  Asp
     130                  135                  140

CTA  TTC  AGT  AGC  GTC  TGG  GTT  GAA  AGA  AAG  TAT  GGT  CTT  TCC  CAT  GAC       480
Leu  Phe  Ser  Ser  Val  Trp  Val  Glu  Arg  Lys  Tyr  Gly  Leu  Ser  His  Asp
145                  150                  155                  160

CAT  ACC  CAC  GAT  GAA  ATT  AAA  GAC  ACT  GTT  GTG  AGA  AAC  ACT  GCA  GCT       528
His  Thr  His  Asp  Glu  Ile  Lys  Asp  Thr  Val  Val  Arg  Asn  Thr  Ala  Ala
                 165                  170                  175

GTT  TCA  AGT  GAG  AAT  GAC  AAT  GAG  AAT  GGT  ACT  GCA  AAT  GGA  TCT  CAT       576
Val  Ser  Ser  Glu  Asn  Asp  Asn  Glu  Asn  Gly  Thr  Ala  Asn  Gly  Ser  His
             180                  185                  190

GAC  ACC  AAG  AAC  GGA  GTA  GAG  TAT  TAT  GAA  GAT  TCA  GAC  GCT  ACA  TCC       624
Asp  Thr  Lys  Asn  Gly  Val  Glu  Tyr  Tyr  Glu  Asp  Ser  Asp  Ala  Thr  Ser
         195                  200                  205

ATG  GAT  GTT  GTT  CAA  TCA  TTT  CAA  GCA  CAA  TTT  TAT  GCC  TTT  TTA  ATT       672
Met  Asp  Val  Val  Gln  Ser  Phe  Gln  Ala  Gln  Phe  Tyr  Ala  Phe  Leu  Ile
     210                  215                  220

TTA  GAA  TTC  GGT  GTG  ATT  TTC  CAC  TCC  GTT  ATG  ATC  GGT  CTA  AAC  CTG       720
Leu  Glu  Phe  Gly  Val  Ile  Phe  His  Ser  Val  Met  Ile  Gly  Leu  Asn  Leu
225                  230                  235                  240

GGA  AGT  GTT  GGT  GAT  GAG  TTC  TCC  TCC  CTA  TAC  CCT  GTC  TTA  GTG  TTC       768
Gly  Ser  Val  Gly  Asp  Glu  Phe  Ser  Ser  Leu  Tyr  Pro  Val  Leu  Val  Phe
                 245                  250                  255
```

| | | | | | | | | | | | | | | | | |
|---|---|---|---|---|---|---|---|---|---|---|---|---|---|---|---|---|
| CAT | CAA | TCA | TTT | GAA | GGT | TTA | GGT | ATT | GGT | GCA | AGA | TTG | TCA | GCC | ATT | 816 |
| His | Gln | Ser | Phe | Glu | Gly | Leu | Gly | Ile | Gly | Ala | Arg | Leu | Ser | Ala | Ile | |
| | | 260 | | | | | | 265 | | | | | 270 | | | |
| GAA | TTC | CCT | AGA | TCA | AAG | AGA | TGG | TGG | CCA | TGG | GCC | CTA | TGT | GTT | GCG | 864 |
| Glu | Phe | Pro | Arg | Ser | Lys | Arg | Trp | Trp | Pro | Trp | Ala | Leu | Cys | Val | Ala | |
| | | 275 | | | | | 280 | | | | | 285 | | | | |
| TAT | GGG | TTA | ACC | ACA | CCA | ATC | TGT | GTG | GCC | ATC | GGT | TTG | GGT | GTT | CGT | 912 |
| Tyr | Gly | Leu | Thr | Thr | Pro | Ile | Cys | Val | Ala | Ile | Gly | Leu | Gly | Val | Arg | |
| | 290 | | | | | 295 | | | | | 300 | | | | | |
| ACC | AGA | TAC | GTC | AGC | GGT | TCT | TAC | ACT | GCG | CTT | GTT | ATC | TCT | GGT | GTT | 960 |
| Thr | Arg | Tyr | Val | Ser | Gly | Ser | Tyr | Thr | Ala | Leu | Val | Ile | Ser | Gly | Val | |
| 305 | | | | | 310 | | | | | 315 | | | | | 320 | |
| TTG | GAT | GCC | ATT | TCT | GCT | GGT | ATC | TTA | TTG | TAC | ACT | GGT | TTG | GTT | GAA | 1008 |
| Leu | Asp | Ala | Ile | Ser | Ala | Gly | Ile | Leu | Leu | Tyr | Thr | Gly | Leu | Val | Glu | |
| | | | | 325 | | | | | 330 | | | | | 335 | | |
| CTA | CTA | GCA | AGA | GAC | TTT | ATA | TTC | AAT | CCT | CAA | AGA | ACA | AAG | GAT | CTA | 1056 |
| Leu | Leu | Ala | Arg | Asp | Phe | Ile | Phe | Asn | Pro | Gln | Arg | Thr | Lys | Asp | Leu | |
| | | | 340 | | | | | 345 | | | | | 350 | | | |
| AGA | GAA | TTG | TCC | TTC | AAC | GTT | ATA | TGC | ACT | CTT | TTC | GGT | GCT | GGT | ATC | 1104 |
| Arg | Glu | Leu | Ser | Phe | Asn | Val | Ile | Cys | Thr | Leu | Phe | Gly | Ala | Gly | Ile | |
| | | 355 | | | | | 360 | | | | | 365 | | | | |
| ATG | GCT | TTG | ATC | GGT | AAG | TGG | GCT | T AA | | | | | | | | 1131 |
| Met | Ala | Leu | Ile | Gly | Lys | Trp | Ala | | | | | | | | | |
| | | 370 | | | | | 375 | | | | | | | | | |

(2) INFORMATION FOR SEQ ID NO:10:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:10:

| | | | | | | | | | | | | | | |
|---|---|---|---|---|---|---|---|---|---|---|---|---|---|---|
| Met | Ser | Asn | Val | Thr | Thr | Pro | Trp | Trp | Lys | Gln | Trp | Asp | Pro | Ser | Glu |
| 1 | | | | 5 | | | | | 10 | | | | | 15 | |
| Val | Thr | Leu | Ala | Asp | Lys | Thr | Pro | Asp | Val | Trp | Lys | Thr | Cys | Val | |
| | | | 20 | | | | | 25 | | | | | 30 | | |
| Leu | Gln | Gly | Val | Tyr | Phe | Gly | Gly | Asn | Glu | Tyr | Asn | Gly | Asn | Leu | Gly |
| | | 35 | | | | | 40 | | | | | 45 | | | |
| Ala | Arg | Ile | Ser | Ser | Val | Phe | Val | Ile | Leu | Phe | Val | Ser | Thr | Phe | Phe |
| | 50 | | | | | 55 | | | | | 60 | | | | |
| Thr | Met | Phe | Pro | Leu | Ile | Ser | Thr | Lys | Val | Lys | Arg | Leu | Arg | Ile | Pro |
| 65 | | | | | 70 | | | | | 75 | | | | | 80 |
| Leu | Tyr | Val | Tyr | Leu | Phe | Ala | Lys | Tyr | Phe | Gly | Ser | Gly | Val | Ile | Val |
| | | | | 85 | | | | | 90 | | | | | 95 | |
| Ala | Thr | Ala | Phe | Ile | His | Leu | Met | Asp | Pro | Ala | Tyr | Gly | Ala | Ile | Gly |
| | | | 100 | | | | | 105 | | | | | 110 | | |
| Gly | Thr | Thr | Cys | Val | Gly | Gln | Thr | Gly | Asn | Trp | Gly | Leu | Tyr | Ser | Trp |
| | | 115 | | | | | 120 | | | | | 125 | | | |
| Cys | Pro | Ala | Ile | Met | Leu | Thr | Ser | Leu | Thr | Phe | Thr | Phe | Leu | Thr | Asp |
| | 130 | | | | | 135 | | | | | 140 | | | | |
| Leu | Phe | Ser | Ser | Val | Trp | Val | Glu | Arg | Lys | Tyr | Gly | Leu | Ser | His | Asp |
| 145 | | | | | 150 | | | | | 155 | | | | | 160 |
| His | Thr | His | Asp | Glu | Ile | Lys | Asp | Thr | Val | Val | Arg | Asn | Thr | Ala | Ala |
| | | | | 165 | | | | | 170 | | | | | 175 | |
| Val | Ser | Ser | Glu | Asn | Asp | Asn | Glu | Asn | Gly | Thr | Ala | Asn | Gly | Ser | His |
| | | | 180 | | | | | 185 | | | | | 190 | | |

| | | | | | | | | | | | | | | |
|---|---|---|---|---|---|---|---|---|---|---|---|---|---|---|
| Asp | Thr | Lys | Asn | Gly | Val | Glu | Tyr | Tyr | Glu | Asp | Ser | Asp | Ala | Thr | Ser |
| | | 195 | | | | | 200 | | | | | 205 | | | |
| Met | Asp | Val | Val | Gln | Ser | Phe | Gln | Ala | Gln | Phe | Tyr | Ala | Phe | Leu | Ile |
| | | 210 | | | | 215 | | | | | 220 | | | | |
| Leu | Glu | Phe | Gly | Val | Ile | Phe | His | Ser | Val | Met | Ile | Gly | Leu | Asn | Leu |
| 225 | | | | | 230 | | | | | 235 | | | | | 240 |
| Gly | Ser | Val | Gly | Asp | Glu | Phe | Ser | Ser | Leu | Tyr | Pro | Val | Leu | Val | Phe |
| | | | | 245 | | | | | 250 | | | | | 255 | |
| His | Gln | Ser | Phe | Glu | Gly | Leu | Gly | Ile | Gly | Ala | Arg | Leu | Ser | Ala | Ile |
| | | | 260 | | | | | 265 | | | | | 270 | | |
| Glu | Phe | Pro | Arg | Ser | Lys | Arg | Trp | Trp | Pro | Trp | Ala | Leu | Cys | Val | Ala |
| | | 275 | | | | | 280 | | | | | 285 | | | |
| Tyr | Gly | Leu | Thr | Thr | Pro | Ile | Cys | Val | Ala | Ile | Gly | Leu | Gly | Val | Arg |
| | 290 | | | | | 295 | | | | | 300 | | | | |
| Thr | Arg | Tyr | Val | Ser | Gly | Ser | Tyr | Thr | Ala | Leu | Val | Ile | Ser | Gly | Val |
| 305 | | | | | 310 | | | | | 315 | | | | | 320 |
| Leu | Asp | Ala | Ile | Ser | Ala | Gly | Ile | Leu | Leu | Tyr | Thr | Gly | Leu | Val | Glu |
| | | | | 325 | | | | | 330 | | | | | 335 | |
| Leu | Leu | Ala | Arg | Asp | Phe | Ile | Phe | Asn | Pro | Gln | Arg | Thr | Lys | Asp | Leu |
| | | | 340 | | | | | 345 | | | | | 350 | | |
| Arg | Glu | Leu | Ser | Phe | Asn | Val | Ile | Cys | Thr | Leu | Phe | Gly | Ala | Gly | Ile |
| | | 355 | | | | | 360 | | | | | 365 | | | |
| Met | Ala | Leu | Ile | Gly | Lys | Trp | Ala | | | | | | | | |
| | 370 | | | | | 375 | | | | | | | | | |

( 2 ) INFORMATION FOR SEQ ID NO:11:

( i ) SEQUENCE CHARACTERISTICS:
        ( A ) LENGTH: 1269 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1267

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| ATG | GTT | GAT | CTT | ATA | GCG | AGG | GAT | GAC | TCC | GTA | GAT | ACT | TGC | CAA | GCT | 48 |
| Met | Val | Asp | Leu | Ile | Ala | Arg | Asp | Asp | Ser | Val | Asp | Thr | Cys | Gln | Ala | |
| 1 | | | | 5 | | | | | 10 | | | | | 15 | | |
| TCT | AAC | GGC | TAC | AAT | GGG | CAC | GCA | GGT | CTT | AGA | ATT | CTG | GCA | GTA | TTC | 96 |
| Ser | Asn | Gly | Tyr | Asn | Gly | His | Ala | Gly | Leu | Arg | Ile | Leu | Ala | Val | Phe | |
| | | | 20 | | | | | 25 | | | | | 30 | | | |
| ATT | ATA | CTG | ATA | TCG | TCA | GGA | TTG | GGA | GTT | TAT | TTC | CCA | ATT | TTG | TCA | 144 |
| Ile | Ile | Leu | Ile | Ser | Ser | Gly | Leu | Gly | Val | Tyr | Phe | Pro | Ile | Leu | Ser | |
| | | 35 | | | | | 40 | | | | | 45 | | | | |
| TCA | CGG | TAT | TCG | TTT | ATA | AGG | CTA | CCA | AAT | TGG | TGC | TTT | TTC | ATA | GCG | 192 |
| Ser | Arg | Tyr | Ser | Phe | Ile | Arg | Leu | Pro | Asn | Trp | Cys | Phe | Phe | Ile | Ala | |
| | 50 | | | | | 55 | | | | | 60 | | | | | |
| AAG | TTC | TTC | GGT | TCT | GGT | GTC | ATT | GTT | GCC | ACA | GCG | TTC | GTT | CAT | CTT | 240 |
| Lys | Phe | Phe | Gly | Ser | Gly | Val | Ile | Val | Ala | Thr | Ala | Phe | Val | His | Leu | |
| 65 | | | | | 70 | | | | | 75 | | | | | 80 | |
| CTA | CAG | CCC | GCA | GCC | GAA | GCT | CTG | GGA | GAT | GAA | TGT | CTT | GGT | GGC | ACA | 288 |
| Leu | Gln | Pro | Ala | Ala | Glu | Ala | Leu | Gly | Asp | Glu | Cys | Leu | Gly | Gly | Thr | |
| | | | | 85 | | | | | 90 | | | | | 95 | | |
| TTT | GCC | GAA | TAT | CCA | TGG | GCT | TTT | GGG | ATC | TGT | TTA | ATG | TCG | CTT | TTC | 336 |
| Phe | Ala | Glu | Tyr | Pro | Trp | Ala | Phe | Gly | Ile | Cys | Leu | Met | Ser | Leu | Phe | |

-continued

```
                        100                              105                              110
TTA  CTT  TTC  TTC  ACT  GAA  ATC  ATC  ACG  CAT  TAT  TTT  GTA  GCG  AAA  ACG          384
Leu  Leu  Phe  Phe  Thr  Glu  Ile  Ile  Thr  His  Tyr  Phe  Val  Ala  Lys  Thr
          115                 120                           125

CTG  GGA  CAC  GAT  CAT  GGG  GAC  CAT  GGG  GAA  GTT  ACC  AGT  ATT  GAT  GTT          432
Leu  Gly  His  Asp  His  Gly  Asp  His  Gly  Glu  Val  Thr  Ser  Ile  Asp  Val
     130                 135                           140

GAT  GCT  CCC  AGT  TCG  GGA  TTT  GTC  ATC  AGA  AAT  ATG  GAC  TCG  GAT  CCT          480
Asp  Ala  Pro  Ser  Ser  Gly  Phe  Val  Ile  Arg  Asn  Met  Asp  Ser  Asp  Pro
145                      150                      155                           160

GTA  TCT  TTC  AAT  AAC  GAA  GCT  GCC  TAC  TCC  ATC  CAT  AAT  GAC  AAA  ACT          528
Val  Ser  Phe  Asn  Asn  Glu  Ala  Ala  Tyr  Ser  Ile  His  Asn  Asp  Lys  Thr
                    165                      170                      175

CCG  TAC  ACT  ACT  AGA  AAT  GAA  GAG  ATT  GTC  GCT  ACT  CCT  ATA  AAG  GAA          576
Pro  Tyr  Thr  Thr  Arg  Asn  Glu  Glu  Ile  Val  Ala  Thr  Pro  Ile  Lys  Glu
               180                      185                      190

AAA  GAA  CCC  GGC  TCA  AAT  GTT  ACT  AAT  TAT  GAT  CTG  GAA  CCG  GGA  AAA          624
Lys  Glu  Pro  Gly  Ser  Asn  Val  Thr  Asn  Tyr  Asp  Leu  Glu  Pro  Gly  Lys
          195                      200                      205

ACA  GAG  TCA  CTA  GCT  AAT  GAA  CTA  GTT  CCA  ACC  AGT  TCC  CAT  GCG  ACA          672
Thr  Glu  Ser  Leu  Ala  Asn  Glu  Leu  Val  Pro  Thr  Ser  Ser  His  Ala  Thr
     210                      215                      220

AAT  CTC  GCT  TCT  GTA  CCT  GGA  AAA  GAT  CAT  TAT  TCT  CAC  GAA  AAT  GAC          720
Asn  Leu  Ala  Ser  Val  Pro  Gly  Lys  Asp  His  Tyr  Ser  His  Glu  Asn  Asp
225                      230                      235                           240

CAT  CAA  GAT  GTC  TCC  CAG  TTG  GCC  ACA  CGT  ATC  GAG  GAG  GAA  GAT  AAA          768
His  Gln  Asp  Val  Ser  Gln  Leu  Ala  Thr  Arg  Ile  Glu  Glu  Glu  Asp  Lys
                    245                      250                      255

GAG  CAG  TAT  CTC  AAT  CAG  ATA  CTA  GCT  GTT  TTT  ATT  CTA  GAA  TTT  GGC          816
Glu  Gln  Tyr  Leu  Asn  Gln  Ile  Leu  Ala  Val  Phe  Ile  Leu  Glu  Phe  Gly
               260                      265                      270

ATC  ATC  TTT  CAC  TCT  GTA  TTT  GTG  GGT  CTT  TCG  CTA  TCT  GTC  GCG  GGT          864
Ile  Ile  Phe  His  Ser  Val  Phe  Val  Gly  Leu  Ser  Leu  Ser  Val  Ala  Gly
          275                      280                      285

GAA  GAA  TTC  GAA  ACC  TTA  TTT  ATC  GTT  TTA  ACT  TTC  CAC  CAA  ATG  TTC          912
Glu  Glu  Phe  Glu  Thr  Leu  Phe  Ile  Val  Leu  Thr  Phe  His  Gln  Met  Phe
290                      295                      300

GAA  GGT  TTG  GGT  CTA  GGC  ACA  AGA  GTT  GCC  GAA  ACG  AAT  TGG  CCA  GAA          960
Glu  Gly  Leu  Gly  Leu  Gly  Thr  Arg  Val  Ala  Glu  Thr  Asn  Trp  Pro  Glu
305                      310                      315                           320

AGT  AAG  AAG  TAC  ATG  CCT  TGG  TTA  ATG  GGA  TTA  GCC  TTC  ACT  TTA  ACG         1008
Ser  Lys  Lys  Tyr  Met  Pro  Trp  Leu  Met  Gly  Leu  Ala  Phe  Thr  Leu  Thr
                    325                      330                      335

TCA  CCC  ATA  GCA  GTC  GCG  GTA  GGT  ATT  GGT  GTC  AGA  CAC  TCT  TGG  ATA         1056
Ser  Pro  Ile  Ala  Val  Ala  Val  Gly  Ile  Gly  Val  Arg  His  Ser  Trp  Ile
               340                      345                      350

CCT  GGC  TCT  AGA  AGA  GCA  TTA  ATT  GCT  AAT  GGT  GTT  TTT  GAC  TCG  ATA         1104
Pro  Gly  Ser  Arg  Arg  Ala  Leu  Ile  Ala  Asn  Gly  Val  Phe  Asp  Ser  Ile
          355                      360                      365

TCA  TCA  GGA  ATT  CTT  ATT  TAT  ACT  GGA  CTA  GTC  GAA  TTA  ATG  GCT  CAT         1152
Ser  Ser  Gly  Ile  Leu  Ile  Tyr  Thr  Gly  Leu  Val  Glu  Leu  Met  Ala  His
     370                      375                      380

GAA  TTC  TTA  TAC  TCT  AAT  CAA  TTC  AAA  GGA  CCT  GAT  GGC  CTC  AAA  AAA         1200
Glu  Phe  Leu  Tyr  Ser  Asn  Gln  Phe  Lys  Gly  Pro  Asp  Gly  Leu  Lys  Lys
385                      390                      395                           400

ATG  CTT  AGT  GCA  TAT  CTC  ATC  ATG  TGT  TGT  GGA  GCT  GCT  TTA  ATG  GCT         1248
Met  Leu  Ser  Ala  Tyr  Leu  Ile  Met  Cys  Cys  Gly  Ala  Ala  Leu  Met  Ala
                    405                      410                      415

CTT  CTA  GGG  AAA  TGG  GCA  T AG                                                     1269
Leu  Leu  Gly  Lys  Trp  Ala
```

420

(2) INFORMATION FOR SEQ ID NO:12:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:12:

| Met | Val | Asp | Leu | Ile | Ala | Arg | Asp | Asp | Ser | Val | Asp | Thr | Cys | Gln | Ala |
|---|---|---|---|---|---|---|---|---|---|---|---|---|---|---|---|
| 1 | | | | 5 | | | | | 10 | | | | | 15 | |
| Ser | Asn | Gly | Tyr | Asn | Gly | His | Ala | Gly | Leu | Arg | Ile | Leu | Ala | Val | Phe |
| | | | 20 | | | | 25 | | | | | 30 | | | |
| Ile | Ile | Leu | Ile | Ser | Ser | Gly | Leu | Gly | Val | Tyr | Phe | Pro | Ile | Leu | Ser |
| | | | 35 | | | | 40 | | | | | 45 | | | |
| Ser | Arg | Tyr | Ser | Phe | Ile | Arg | Leu | Pro | Asn | Trp | Cys | Phe | Phe | Ile | Ala |
| | 50 | | | | | 55 | | | | | 60 | | | | |
| Lys | Phe | Phe | Gly | Ser | Gly | Val | Ile | Val | Ala | Thr | Ala | Phe | Val | His | Leu |
| 65 | | | | | 70 | | | | | 75 | | | | | 80 |
| Leu | Gln | Pro | Ala | Ala | Glu | Ala | Leu | Gly | Asp | Glu | Cys | Leu | Gly | Gly | Thr |
| | | | | 85 | | | | | 90 | | | | | 95 | |
| Phe | Ala | Glu | Tyr | Pro | Trp | Ala | Phe | Gly | Ile | Cys | Leu | Met | Ser | Leu | Phe |
| | | | | 100 | | | | | 105 | | | | | 110 | |
| Leu | Leu | Phe | Phe | Thr | Glu | Ile | Ile | Thr | His | Tyr | Phe | Val | Ala | Lys | Thr |
| | | | 115 | | | | 120 | | | | | 125 | | | |
| Leu | Gly | His | Asp | His | Gly | Asp | His | Gly | Glu | Val | Thr | Ser | Ile | Asp | Val |
| | 130 | | | | | 135 | | | | | 140 | | | | |
| Asp | Ala | Pro | Ser | Ser | Gly | Phe | Val | Ile | Arg | Asn | Met | Asp | Ser | Asp | Pro |
| 145 | | | | | 150 | | | | | 155 | | | | | 160 |
| Val | Ser | Phe | Asn | Asn | Glu | Ala | Ala | Tyr | Ser | Ile | His | Asn | Asp | Lys | Thr |
| | | | | 165 | | | | | 170 | | | | | 175 | |
| Pro | Tyr | Thr | Thr | Arg | Asn | Glu | Glu | Ile | Val | Ala | Thr | Pro | Ile | Lys | Glu |
| | | | | 180 | | | | | 185 | | | | | 190 | |
| Lys | Glu | Pro | Gly | Ser | Asn | Val | Thr | Asn | Tyr | Asp | Leu | Glu | Pro | Gly | Lys |
| | | | 195 | | | | 200 | | | | | 205 | | | |
| Thr | Glu | Ser | Leu | Ala | Asn | Glu | Leu | Val | Pro | Thr | Ser | Ser | His | Ala | Thr |
| | 210 | | | | | 215 | | | | | 220 | | | | |
| Asn | Leu | Ala | Ser | Val | Pro | Gly | Lys | Asp | His | Tyr | Ser | His | Glu | Asn | Asp |
| 225 | | | | | 230 | | | | | 235 | | | | | 240 |
| His | Gln | Asp | Val | Ser | Gln | Leu | Ala | Thr | Arg | Ile | Glu | Glu | Glu | Asp | Lys |
| | | | | 245 | | | | | 250 | | | | | 255 | |
| Glu | Gln | Tyr | Leu | Asn | Gln | Ile | Leu | Ala | Val | Phe | Ile | Leu | Glu | Phe | Gly |
| | | | | 260 | | | | | 265 | | | | | 270 | |
| Ile | Ile | Phe | His | Ser | Val | Phe | Val | Gly | Leu | Ser | Leu | Ser | Val | Ala | Gly |
| | | | 275 | | | | 280 | | | | | 285 | | | |
| Glu | Glu | Phe | Glu | Thr | Leu | Phe | Ile | Val | Leu | Thr | Phe | His | Gln | Met | Phe |
| | | 290 | | | | | 295 | | | | | 300 | | | |
| Glu | Gly | Leu | Gly | Leu | Gly | Thr | Arg | Val | Ala | Glu | Thr | Asn | Trp | Pro | Glu |
| 305 | | | | | 310 | | | | | 315 | | | | | 320 |
| Ser | Lys | Lys | Tyr | Met | Pro | Trp | Leu | Met | Gly | Leu | Ala | Phe | Thr | Leu | Thr |
| | | | | 325 | | | | | 330 | | | | | 335 | |
| Ser | Pro | Ile | Ala | Val | Ala | Val | Gly | Ile | Gly | Val | Arg | His | Ser | Trp | Ile |
| | | | 340 | | | | 345 | | | | | 350 | | | |

```
          Pro  Gly  Ser  Arg  Arg  Ala  Leu  Ile  Ala  Asn  Gly  Val  Phe  Asp  Ser  Ile
               355                      360                      365

Ser  Ser  Gly  Ile  Leu  Ile  Tyr  Thr  Gly  Leu  Val  Glu  Leu  Met  Ala  His
               370                      375                      380

Glu  Phe  Leu  Tyr  Ser  Asn  Gln  Phe  Lys  Gly  Pro  Asp  Gly  Leu  Lys  Lys
          385                      390                      395                      400

Met  Leu  Ser  Ala  Tyr  Leu  Ile  Met  Cys  Cys  Gly  Ala  Ala  Leu  Met  Ala
                              405                      410                      415

Leu  Leu  Gly  Lys  Trp  Ala
                         420
```

( 2 ) INFORMATION FOR SEQ ID NO:13:

( i ) SEQUENCE CHARACTERISTICS:
        ( A ) LENGTH: 1264 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..1037

( x i ) SEQUENCE DESCRIPTION: SEQ ID NO:13:

```
TC  GAC  CCA  CGC  GTC  CGC  CTC  ATC  CTA  TTC  ACC  TTC  ACC  GTA  TCT  CCG         47
    Asp  Pro  Arg  Val  Arg  Leu  Ile  Leu  Phe  Thr  Phe  Thr  Val  Ser  Pro
    1              5                        10                       15

GCG  ATC  TCA  ACG  GCC  CCG  GAA  CAT  TGT  GAT  AGC  GGC  TTT  GAT  AAC  CCG         95
Ala  Ile  Ser  Thr  Ala  Pro  Glu  His  Cys  Asp  Ser  Gly  Phe  Asp  Asn  Pro
                    20                       25                       30

TGC  ATC  AAC  AAA  GCT  AAG  GCT  TTA  CCA  CTC  AAA  ATC  GTA  GCC  ATT  GTT        143
Cys  Ile  Asn  Lys  Ala  Lys  Ala  Leu  Pro  Leu  Lys  Ile  Val  Ala  Ile  Val
              35                       40                       45

GCC  ATA  CTT  ACA  ACA  AGC  TTG  ATA  GGC  GTG  ACC  TCT  CCT  CTT  TTC  AGC        191
Ala  Ile  Leu  Thr  Thr  Ser  Leu  Ile  Gly  Val  Thr  Ser  Pro  Leu  Phe  Ser
         50                       55                       60

CGT  TAC  ATT  TCG  TTC  CTC  CGT  CCC  GAT  GGC  AAT  GGT  TTC  ATG  ATC  GTC        239
Arg  Tyr  Ile  Ser  Phe  Leu  Arg  Pro  Asp  Gly  Asn  Gly  Phe  Met  Ile  Val
    65                       70                       75

AAA  TGT  TTT  TCT  TCT  GGA  ATC  ATC  CTT  GGA  ACC  GGT  TTC  ATG  CAC  GTC        287
Lys  Cys  Phe  Ser  Ser  Gly  Ile  Ile  Leu  Gly  Thr  Gly  Phe  Met  His  Val
80                       85                       90                       95

TTG  CCT  GAC  TCT  TTC  GAG  ATG  TTG  TCA  TCG  AAA  TGT  CTT  AGT  GAT  AAT        335
Leu  Pro  Asp  Ser  Phe  Glu  Met  Leu  Ser  Ser  Lys  Cys  Leu  Ser  Asp  Asn
                    100                      105                      110

CCG  CGG  CAT  AAG  TTC  CCT  TCT  GGG  GGT  TTA  GTC  GCT  ATG  ATG  TCC  GGT        383
Pro  Arg  His  Lys  Phe  Pro  Ser  Gly  Gly  Leu  Val  Ala  Met  Met  Ser  Gly
              115                      120                      125

CTA  GTC  ACT  CTA  GCC  ATT  GAC  TCC  ATT  ACC  ACC  AGC  TTA  TAT  ACC  GGT        431
Leu  Val  Thr  Leu  Ala  Ile  Asp  Ser  Ile  Thr  Thr  Ser  Leu  Tyr  Thr  Gly
         130                      135                      140

AAG  AAC  TCA  GTC  GGA  CCA  GTG  CCT  GAT  GAA  GAG  TAT  GGC  ATT  GAT  CAA        479
Lys  Asn  Ser  Val  Gly  Pro  Val  Pro  Asp  Glu  Glu  Tyr  Gly  Ile  Asp  Gln
    145                      150                      155

GAG  AAA  GCG  ATT  CAC  ATG  GTA  GGC  CAC  AAT  CAT  AGT  CAC  GGT  CAT  GGT        527
Glu  Lys  Ala  Ile  His  Met  Val  Gly  His  Asn  His  Ser  His  Gly  His  Gly
160                      165                      170                      175

GTA  GTG  CTA  GCA  ACT  AAA  GAT  GAT  GGA  CAG  CTT  TTG  CGC  TAC  CAA  GTC        575
Val  Val  Leu  Ala  Thr  Lys  Asp  Asp  Gly  Gln  Leu  Leu  Arg  Tyr  Gln  Val
                    180                      185                      190
```

```
ATT  GCC  ATG  GTA  TTG  GAG  GTT  GGG  ATT  TTA  TTT  CAT  TCT  GTG  GTC  ATT           623
Ile  Ala  Met  Val  Leu  Glu  Val  Gly  Ile  Leu  Phe  His  Ser  Val  Val  Ile
               195                      200                      205

GGA  CTA  TCT  CTA  GGA  GCA  ACT  AAT  GAT  TCA  TGT  ACC  ATT  AAA  GGA  CTC           671
Gly  Leu  Ser  Leu  Gly  Ala  Thr  Asn  Asp  Ser  Cys  Thr  Ile  Lys  Gly  Leu
          210                      215                      220

ATC  ATA  GCT  CTT  TGC  TTC  CAT  CAC  TTG  TTC  GAA  GGC  ATA  GGT  CTT  GGT           719
Ile  Ile  Ala  Leu  Cys  Phe  His  His  Leu  Phe  Glu  Gly  Ile  Gly  Leu  Gly
     225                      230                      235

GGC  TGC  ATC  CTC  CAG  GCA  GAT  TTT  ACA  AAT  GTG  AAG  AAG  TTC  TTG  ATG           767
Gly  Cys  Ile  Leu  Gln  Ala  Asp  Phe  Thr  Asn  Val  Lys  Lys  Phe  Leu  Met
240                 245                      250                      255

GCA  TTC  TTT  TTC  ACT  GGA  ACA  ACA  CCT  TGT  GGT  ATC  TTT  CTT  GGA  ATC           815
Ala  Phe  Phe  Phe  Thr  Gly  Thr  Thr  Pro  Cys  Gly  Ile  Phe  Leu  Gly  Ile
                    260                      265                      270

GCA  TTG  TCG  AGT  ATC  TAT  AGA  GAT  AAC  AGT  CCA  ACC  GCG  TTG  ATT  ACG           863
Ala  Leu  Ser  Ser  Ile  Tyr  Arg  Asp  Asn  Ser  Pro  Thr  Ala  Leu  Ile  Thr
               275                      280                      285

ATT  GGA  CTG  TTA  AAT  GCT  TGC  TCG  GCC  GGA  ATG  CTC  ATC  TAC  ATG  GCC           911
Ile  Gly  Leu  Leu  Asn  Ala  Cys  Ser  Ala  Gly  Met  Leu  Ile  Tyr  Met  Ala
          290                      295                      300

CTC  GTC  GAC  CTT  CTA  GCT  ACC  GAG  TTC  ATG  GGG  TCA  ATG  CTC  CAA  GGT           959
Leu  Val  Asp  Leu  Leu  Ala  Thr  Glu  Phe  Met  Gly  Ser  Met  Leu  Gln  Gly
     305                      310                      315

AGC  ATC  AAA  CTT  CAG  ATC  AAG  TGC  TTC  ACG  GCG  GCT  TTG  CTT  GGC  TGC          1007
Ser  Ile  Lys  Leu  Gln  Ile  Lys  Cys  Phe  Thr  Ala  Ala  Leu  Leu  Gly  Cys
320                 325                      330                      335

GCC  GTA  ATG  TCG  GTC  GTC  GCC  GTG  TGG  GCT  TAAACACTCT  TTCAACATAA                 1057
Ala  Val  Met  Ser  Val  Val  Ala  Val  Trp  Ala
               340                      345

TCAATAAATT  ATTTGATTTA  TTAATCCAGG  CGACCAATAC  TTTCGCCTTT  GGAAAATTGA                   1117

GTTTTGTTT  TTAAGTTTGA  ATCATTTATT  AGTTTGTATA  GTGCATGTAA  GCGTTTGAAA                    1177

GAAATTTCTT  TTTATGACAT  TGTAAATTTA  TTTTTATGGA  TGCGATGTTT  ACTTTCTTAA                   1237

AAAAAAAAAA  AAAAAAAAAA  AAAAAA                                                           1264
```

( 2 ) INFORMATION FOR SEQ ID NO:14:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Asp  Pro  Arg  Val  Arg  Leu  Ile  Leu  Phe  Thr  Phe  Thr  Val  Ser  Pro  Ala
  1                  5                     10                      15

Ile  Ser  Thr  Ala  Pro  Glu  His  Cys  Asp  Ser  Gly  Phe  Asp  Asn  Pro  Cys
               20                      25                      30

Ile  Asn  Lys  Ala  Lys  Ala  Leu  Pro  Leu  Lys  Ile  Val  Ala  Ile  Val  Ala
          35                      40                      45

Ile  Leu  Thr  Thr  Ser  Leu  Ile  Gly  Val  Thr  Ser  Pro  Leu  Phe  Ser  Arg
     50                      55                      60

Tyr  Ile  Ser  Phe  Leu  Arg  Pro  Asp  Gly  Asn  Gly  Phe  Met  Ile  Val  Lys
 65                      70                      75                       80

Cys  Phe  Ser  Ser  Gly  Ile  Ile  Leu  Gly  Thr  Gly  Phe  Met  His  Val  Leu
               85                      90                      95

Pro  Asp  Ser  Phe  Glu  Met  Leu  Ser  Ser  Lys  Cys  Leu  Ser  Asp  Asn  Pro
               100                     105                     110
```

```
Arg  His  Lys  Phe  Pro  Ser  Gly  Gly  Leu  Val  Ala  Met  Met  Ser  Gly  Leu
          115                      120                     125

Val  Thr  Leu  Ala  Ile  Asp  Ser  Ile  Thr  Thr  Ser  Leu  Tyr  Thr  Gly  Lys
     130                      135                     140

Asn  Ser  Val  Gly  Pro  Val  Pro  Asp  Glu  Glu  Tyr  Gly  Ile  Asp  Gln  Glu
145                      150                     155                          160

Lys  Ala  Ile  His  Met  Val  Gly  His  Asn  His  Ser  His  Gly  His  Gly  Val
               165                      170                     175

Val  Leu  Ala  Thr  Lys  Asp  Asp  Gly  Gln  Leu  Leu  Arg  Tyr  Gln  Val  Ile
               180                      185                     190

Ala  Met  Val  Leu  Glu  Val  Gly  Ile  Leu  Phe  His  Ser  Val  Val  Ile  Gly
          195                      200                     205

Leu  Ser  Leu  Gly  Ala  Thr  Asn  Asp  Ser  Cys  Thr  Ile  Lys  Gly  Leu  Ile
     210                      215                     220

Ile  Ala  Leu  Cys  Phe  His  His  Leu  Phe  Glu  Gly  Ile  Gly  Leu  Gly  Gly
225                      230                     235                          240

Cys  Ile  Leu  Gln  Ala  Asp  Phe  Thr  Asn  Val  Lys  Lys  Phe  Leu  Met  Ala
                    245                      250                     255

Phe  Phe  Phe  Thr  Gly  Thr  Thr  Pro  Cys  Gly  Ile  Phe  Leu  Gly  Ile  Ala
               260                      265                     270

Leu  Ser  Ser  Ile  Tyr  Arg  Asp  Asn  Ser  Pro  Thr  Ala  Leu  Ile  Thr  Ile
          275                      280                     285

Gly  Leu  Leu  Asn  Ala  Cys  Ser  Ala  Gly  Met  Leu  Ile  Tyr  Met  Ala  Leu
     290                      295                     300

Val  Asp  Leu  Leu  Ala  Thr  Glu  Phe  Met  Gly  Ser  Met  Leu  Gln  Gly  Ser
305                      310                     315                          320

Ile  Lys  Leu  Gln  Ile  Lys  Cys  Phe  Thr  Ala  Ala  Leu  Leu  Gly  Cys  Ala
                    325                      330                     335

Val  Met  Ser  Val  Val  Ala  Val  Trp  Ala
               340                      345
```

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CGGATCCATG AGCAACGTTA CTACG                                        25

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

TACGCGTCGA CTTAAGCCCA CTTACCGAT                                29

( 2 ) INFORMATION FOR SEQ ID NO:17:

( i ) SEQUENCE CHARACTERISTICS:

(A) LENGTH: 28 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

GGAATTCGAA GGCAAGAGTA TTTCAGAC 28

(2) INFORMATION FOR SEQ ID NO:18:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:18:

CGGGATCCAT AATTCCTTTT TTGATATTTG 30

(2) INFORMATION FOR SEQ ID NO:19:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

ACGCGTCGAC ATGGTTGATC TTATAGCGAG 30

(2) INFORMATION FOR SEQ ID NO:20:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

CCCGAGCTCC TATGCCCATT TCCCTAG 27

(2) INFORMATION FOR SEQ ID NO:21:

(i) SEQUENCE CHARACTERISTICS:
(A) LENGTH: 16 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:21:

Pro Ala Asn Asp Val Thr Leu Pro Ile Lys Glu Asp Asp Ser Ser Asn
1               5                   10                  15